United States Patent [19]

Andersson et al.

[11] Patent Number: 5,679,521

[45] Date of Patent: Oct. 21, 1997

[54] STEROID 5A-REDUCTASES

[75] Inventors: Stefan Andersson, New York, N.Y.; David W. Russell, Dallas, Tex.

[73] Assignee: Board of Regents, The University of Texas System, Austin, Tex.

[21] Appl. No.: 457,616

[22] Filed: Jun. 1, 1995

Related U.S. Application Data

[60] Division of Ser. No. 795,859, Nov. 18, 1991, Pat. No. 5,422,262, which is a continuation-in-part of Ser. No. 517,661, Apr. 30, 1990, abandoned.

[51] Int. Cl.$^6$ .............................. C12Q 1/68; C12P 21/02; C12N 15/00; C12N 9/02
[52] U.S. Cl. .................... 435/6; 435/69.1; 435/172.3; 435/189; 536/23.2; 536/23.5
[58] Field of Search ................... 435/69.1, 6, 7.6, 435/7.71, 71.1, 172.1, 172.3, 189; 536/23.2, 23.5

[56] References Cited

U.S. PATENT DOCUMENTS 5,422,262  6/1995  Andersson et al. .................... 435/365

OTHER PUBLICATIONS

Montell and Goodman, "Drosophila Substrate Adhesion Molecule: Sequence of Laminin B1 Chain Reveals Domains of Homology with Mouse", *Cell*, 53:463–473, 1988.

Thigpen, et al., "Characterization of Chinese Hamster Ovary Cell Lines Expressing Human Steroid 5α–Reductase Isozymes", *Journal of Biological Chemistry*, 268:17404–17412, 1993.

*Primary Examiner*—James Ketter
*Assistant Examiner*—John S. Brusca
*Attorney, Agent, or Firm*—Arnold, White, & Durkee

[57] ABSTRACT

Disclosed are methods and compositions for the preparation of steroid 5α-reductases by recombinant means, as well as for the use of these enzymes in screening assays for the identification of compounds which have the ability to inhibit or otherwise alter the enzymatic function of these enzymes. Biochemical and pharmacological evidence is presented to demonstrate the existence of more than one human steroid 5α-reductase. The DNA sequence encoding steroid 5α-reductase 2, the major active isozyme of human genital tissue, is disclosed herein, in addition to methods and compositions for its preparation and pharmacological analysis. The sequences disclosed herein may be used directly in the preparation of genetic constructs, or may be employed in the preparation of hybridization probes for the selection of enzyme-encoding sequences from other sources. These sequences may prove useful in an analysis of normal and abnormal sexual differentiation, benign prostatic hyperplasia, male pattern baldness, acne, hirsutism, endometriosis, and cancer of the prostate.

13 Claims, 31 Drawing Sheets

Sucrose gradient fractionation of ♀ rat liver RNA

Construction of oriented, size-fractionated cDNA library

In vitro transcription of plasmid pools with T7 RNA polymerase

Injection of Xenopus oocytes and assay of 5α-reductase activity by TLC

Subdivision of positive pools to yield unique 5α-reductase cDNA

FIG. 4A

```
  1
  MetGluLeuAspGluLeuLeuCysLeuLeuValTyrLeuLeuGlyPhe
  ACCTCAGCTATGGAGTTGGATGAGCTGCTGTGCCTGCTCGACATGGTCTACTTGGAAGGTTTC
                          10

SerProGlnTrpProGlyIleArgValProAlaTrpProAlaArgProAlaTrpPheIleGlnGluLeuPro
  TCGCCGCAGTGGCCCGGCATCCGAGTGCCCGCGCCGGCGACCTGCCTGGTTCATACAGGAGCTGCCC
                          40                                    50

LeuProAsnArgValLeuLeuLeuAlaMetPheLeuIleHisTyrValGlnArgThrLeuValPhe
  CTGCCTAACCGCGTCCTGCTGCTGGCTATGTTTCTGATCCACTACGTGCAAAGGACGCTGGTTTTC
                          80                                    90

LeuPheCysThrPheAsnGlyTyrTyrValGlnSerArgTyrLeuSerGlnPheAlaValTyrAla
  CTGTTCTGCACCTTCAACGGCTATTACGTACAGAGCAGATACTTGAGCCAGTTTGCGGTTTATGCT
                          120                                   130

MetValIleAsnIleHisSerAspHisIleLeuArgAsnLeuArgLysProGlyGluThrGly
  ATGGTGATAAATATCCACTCAGACCACATCCTGAGGAATCTGAGAAAACCAGGGGAAACTGGA
                          160                                   170

GluLeuValGluTrpCysGlyPheAlaLeuAlaSerTrpSerLeuGlnGlyValValPheAla
  GAGCTCGTGGAGTGGTGTGGCTTTGCACTGGCCAGCTGGTCCCTCGAGGGTAGTGTTTGCA
                          200                                   210

GluLysPheGluAspTyrProLysSerArgLysIleLeuLeuIleProPheValLeu***
  GAGAAGTTTGAAGATTACCCCAAGTCAAGAAAAATACTGATTCCATTTGTGCTTTAGTGTCTCT
                          240                                   250
```

FIG.4B

```
         20                    30
MetAlaPheValSerIleValGlyLeuArgSerValGlySerProTyrGlyArgTyr
ATGGCCTTCGTGTCGTCATTGTGGGGCTCCGGTTGGCTCCGGTTACGGGCCGCTAC        120

60                    70
SerMetAlaTrpProLeuTyrGluTyrIleArgProAlaAlaAlaArgLeuGlyAsn
TCGATGGCCTGGCCTGTACGAGTACATTCGTCCTGCAGCCGCGCGGACTGGGCAAC        240

100                   110
ProValLeuIleArgGlyLysLysProThrLeuValThrPheValLeuAlaPhe
CCGGTTCTGATCAGGGGGAAGAAGCCCACCCTCCTGGTCACCTTTGTCTTGGCCTTC       360

140                   150
GluAspTrpValThrHisProCysPheLeuThrGlyPheAlaLeuTrpLeuValGly
GAAGACTGGGTGACCCATCCCTGTTTCCTGACAGGCTTTGCCCTGTGGTTAGTGGGC       480

180                   190
TyrLysIleProArgGlyGlyLeuPheGluTyrValSerAlaAlaAsnTyrPheGly
TACAAGATACCCAGGGGAGGCCTGTTTGAATACGTATCTGCAGCCAACTATTTGGG       600

220                   230
LeuPheThrLeuSerThrLeuThrArgAlaAlaLysGlnHisHisGlnTrpTyrHis
CTGTTCACACTCAGCACACTGACCAGAGCAGCCAAGCAGCACCATCAGTGGTACCAT      720

GTTAGCGCTGTTGCTGCTCCCATGAGCTGAGTCTGTCTGTCTCCCTGGTGACTTTGCTC    840
```

FIG.4C

```
TGAGCACTTACGAATGAATTGTTTTCCTTAATTCTCCTGCAGCCCCTTTCTCAGGAAAGGCTG
CACATGCAGTTAGGGGTACACTGCCTGCTGGATCCGAAGCAGGTAGCCCTGAGTCATTATGG
CAGCAGCAGTCACGGGCCTCCTTCACTGATGTGTTCTGCCTGCTCAGCCCTGCCACAGAG
CTTGGACCCCACCCCACTCCCTCCAGACACTGGTAAGAGAAGCCTTCCTGCAACATGTCCTGT
TTCCTTTGGGCTAGAATTCATTAAGGTCCTTAAAAACAAAACAAAACTTTTCTTAATAGTAC
TCACACAAAGAAAGCTCAGGGCTAGCCTGGTGTAGGGAGACCCTGTTTGGGAAAAAAA
CGCCCACACAGGCACCAGCTTGGGAGAAAGATGTGCCCTGGGATTGTAAACCCACTGTTGCT
CCTCGGGGCAGGTGTCACTCAGCCCTGCCACCACAGCTAAAGAACAGAACGGA
TGATGGCGTGCACGGTGCCCCACCACTGCCTGACTCGGACCATCTCTGTGCCCGCTGCCAC
TCAGACAGAAACTATTCTCGTTCCTCTGGTTCGCAGAATGTCTAGATTGACCCAGAAAACT
CAATCCTTTACCCTGCCAAGTAACTGCTTGAAAACCTAAAGCACTAAACATT
AAGGAGATATTCAGCTGAGACCCTGGGAATGTTTGCTGTGAACTTGACCTCCCTGGAGGGCA
CTAAGCCACATCACACATTAGCTCTGTGATGCCTCTTTCTTTATGAAGGACCAAGCTGCCCAC
CTACAACTCAACTTACTTGTATGAACCATGATTGTTAAGGAAATTAATAACTACATTTATAA
```

FIG. 4-D

```
GGGTGGGGGTGTCGTCCCTGGTAAAGGACAAAGCCAATGATAAACTAATCCAC      960
CGCTCTCTGACTTCAGCAATCAGCAGCCCTTACAATCCTGCAAGATTCCACCAAGT  1080
GCCTGGAGGTGTGGGAGTGTGGCCTAAGCACAGTCTGCCATCCTTGACCGCAGACCT 1200
CCTCAGGAGGTGAGACAGCAGAGTGCTTCCATTCACTCGATGACCCCATTTTGCTC  1320
AAAACAAAATATCAAAACAAAATTTGTTATTTGAATGCACCCAAGGACCAATCATG  1440
AATGAAGATAACAACCAGCTAACTGTCCAAAGAAGTGACCGCAGTAATAAAAGACGC  1560
CTGGGCAGGCTGAGGCCCACTGGTGAAGAGCCATTCCCACGGACCCATGCACACTG  1680
TAGAACTGTGTGCTCTGAACCCAGTGCTGGCTTTCCATCAGGGCTTCCTCAGCTCTTGCTC 1800
CTCTGTGTGCCCTTTCCAGCTACTTCATTTTTAACAAAGAGCAGTGTTAATGGGAACTACCCCTT 1920
TCATGACACAGCTACTTCATTTTTAACAAAGAGCAGTGTTAATGGGAACTACCCCTT 2040
GTAGGTCTCCTCTCAAAACCTCAGGCCTGTCGGGTGTGTTCTGAAACGTTTGTGTGG    2160
TGGTGCTAGATAAAGTTGGAACCTAGGACTCCAGGTTGCTAGGCGGATGCCCTGACA    2280
ATACTAAGTGAGATTAATTTAAGAGGAATCCTGTCCTAACACTGTATACTTCATTCC    2400
GTAAAAA....   2470
```

FIG. 7A

```
                                                      1
                                                      MetAlaThrAlaThrGlyValAlaGluGluArg                    10
GGGCATGGAGCACGCTGCCCAGCCCCTGGCGATGGCAACGGGCGACGGGGTGGCGGAGGAGCGC
 31                                         40                                           50
AsnArgGlnThrAsnSerValTyrGlyTyrArgHisAlaLeuProSerHisArgLeuArgValPro
AATCGTCAGACGAACTCAGTGTACGGCTACCGGCACGCCCTGCCCAGCCACAGGCTCCGACTGCCG
 71                                         80                                           90
TyrAlaSerGluSerAlaProArgLeuArgSerAlaProAsnCysIleLeuLeuAlaMetPhe
TACGCCAGCGAGAGTGCCCCGCGGCTCCGCAGCGCCCCCAACTGCATCCTCCTGGCCATGTTC
111                                        120                                         130
ProMetProLeuLeuAlaCysThrMetAlaIleMetPheCysThrCysAsnGlyTyrLeuGln
CCTATGCCACTGTTGGCATGTACAATGGCGATTATGTTCTGTACCTGTAACGGGCTATTTGCAA
151                                        160                                         170
PheLeuIleGlyPheGlyLeuThrGlyMetLeuIleAsnIleHisSerAspHisIle
TTTCTAATAGGTTTTGGCTTGTGGTTAACAGGCATGTTGATAAACATTCAGATCATATC
```

FIG. 7B

```
         20                          30
LeuLeuAlaAlaLeuAlaTyrLeuGlnCysAlaValGlyCysAlaValPheAlaArg
CTGCTGGCCGCGCTCGCCTACCTGCAGTGCGCCGTGGGCTGCGCGGTCTTCGCGCGG    120
         60                          70
AlaArgAlaAlaTrpValValGlnGluLeuProSerLeuAlaLeuProLeuTyrGln
GCGCGGGCCGCCTGGGTGGTGCAGGAGCTGCCCTCGCTGGCCCTGCCGCTCTACCAG    240
         100                         110
LeuValHisTyrGlyHisArgCysLeuIleTyrProPheLeuMetArgGlyGlyLys
CTCGTCCACTACGGGCATCGGTGCTTAATTTACCCGTTTCTGATGCGAGGAGGAAAG    360
         140                         150
SerArgTyrLeuSerHisCysAlaValTyrAlaAspAspTrpValThrAspProArg
AGCAGATACCTTGAGCCATTGTGCAGTGTATGCTGATGACTGGGTAACAGATCCCCGT    480
         180                         190
LeuArgAsnLeuArgLysProGlyAspThrGlyTyrTyrLysIleProArgGlyGlyLeu
CTAAGGAATCTCAGAAAACCAGGAGATACTGGATACAAAATACCAAGGGAGGCTTA    600
```

FIG. 7E

```
191 PheGluTyrValThrAlaAlaAsnTyrPheGlyGluIleMetGluTrpCysGlyTyrAlaLeu
    TTTGAATACGTAACTGCAGCCAACTATTTGGAGAAATCATGGAGTGGTGTGGCTATGCCCTG
                          200                    210
231 GlyArgAlaLysGluHisHisGluTrpTyrLeuArgLysPheGluGluTyrProLysPheArg
    GGTAGAGCAAAAGAGCATCATGAGTGGTACCTCCGGAAATTTGAAGAGTATCCAAAGTTCAGA
                          240                    250
    GAAGCTTTCCAATGGCGCTTCTCTATGGACTTTGTAAATAAGTTATATCTTTGTAATTTTCCT
    TCTACCTAATAAGTACCTAAATACGCTGAAATGGAGGTTGAATATCCTACAACTGTCTTTGATGGCATT
    CTTTGGCTATGTCTTGCCAAGTGTGTCCCCTATGAGACTAGAGGGCTGAATCTGTCTAGGAGCCCTCTCG
    GTCAACTGCAGGTGTTGCTTCCCTGTGTGTAAGTGGAGAACTTGGGAGTCTGTGGGATAGAGGAGGAAGCTCCCGT
    AACCTTCGTGTCAGGTGCTCTGGTCTGACATGGTTTCTCTCTGTCTCTAGTTGCTCTGCCTGTG
    GACATCACCGGGCAGGGGGGTGCTCTGGTCTGACATGGTTTGTAGTGTAAAGAATGATCACTTCTGTAACAATAACAAGACC
    CCATCAATGTGCTCTGGTCTGAGTTTCCCTTGTAGTGTAAAGAATGATCACTTCTGTAACAATAACAAGACC
    GTAGATTTGAGTTTCCCTTGTAGTGTAAAGAATGATCACTTCTGTAACAATAGTTTTGTTCTGT
    ATTCTACAGCCTTCTTTTTCTTCCATAGCTAATCTCCTTCTACTTGAATTCTACTTTGATAAAAACATTGCCATA
    AAAATAATCTTCCTGTGAATGCTTCATGACTTGAATTCTACTTTGATAAAAACATTGCCATA
    AGTTTTAAATGCCATTTGTTTCAGTTGTCTTTAACAACATAATAAATAGACTTTGCCATTTA
```

FIG. 7D

```
                    220                                     230
AlaSerTrpSerValGlnGlyAlaAlaPheAlaPheThrPheCysPheLeuSer
GCCAGCTGGTCTGTGTCCAAGGCGCGGGCTTTGCTTTCTTCACGTTTTGTTTTTATCT       720
         259
LysIleIleIleProPheLeuPheEnd
AAAATTATAATTCCATTTTGTTTTTCAAGATGTCCTCTAGGAATTTTTTCTAGTAATTTTGCAA       840
GCTACTTTATCATTTTCAAGATGTCCTCTAGGAATTTTTTCTAGTAATTTTGCAA       960
AGAATTCAAGCTCTGGGTAATAACTGCTGATATTTTCTAATTTCAAATTACCT       1080
TTCAGAACAATAAAATGTCACAATCCCTCTATAGCCCCTACAGTGATCTCTTCAAG       1200
GAGGCCACAGAGGCTGGGGGTAGCCAAAGGCATGTGCAGTCAGTCATGGGCCCGGGGGAAACTGCC       1320
GGCCCTTCCAAGGTGAGGCAAAGGCACCTTTAGGCCACCTTTAGAGAGATTGTGTCTGTGAAATTTCTTTT       1440
TGAGTGGCTCCTGGGCCCTAAACAGGCATGGATATAGTAGAGATTGTGTCTGTGAAATTTCTTTT       1560
GTTCTGTGTCCCCACGTATGGGATATAGTAGAGATTGTGTCTGTGAAATTTCTTTT       1680
ACTTTTAAGATTATCCTGTTTGTTGTTCTTGTTGATTGAAACATAATAATTGTTAAA       1800
TTTGCTGTGTGTTGCTTTGCAAAGCTTTCCCCTCATAGCCTGTACCTGTTATCAATAT       1920
CTGCTTTTATCTGATGAATTCATCTGCCTTATCATCTCATCTGG       2040
AAAA...2107
```

FIG. 10A

```
GATCTCGGGGTAGCCTCCTTCCCAGCCCTGAGGAAGGAAAGAGAGCGTCTACCCCGAGGCCCAA
GCCCCTGGCCGCCGCCCGGGTCCCGGCTCCTACGCTCTGCGCGCTTTCCACCACCCTCG
CGGCGGCCCATAGCCCACGGCCGCGCACGCAGCACGCAGAAACCGGCCCGCACGGCCAGA
GGCCTGGTCCTTTCGGGGACCTTTGGGGACCGTCCAGGAATAAGCCAAAGCGCACAACCCGT
GCTCCAGGAAGCAGCCACAAAGGCGTCTCCCGGCGAAGGCCCAGGTTCCCACGCGGGCTCA
GGCCCCGGCGTGGGGTGGGGCGCTTGCAGGTCCCCCGGCAAGTGCTCGCCCCGCCCCCCGG
AGAGTCCCCGGCAGTGCGGGGACTCCGGTAGCCGCCCCCCTCCGCCCCCTCCTGCCCCCGC
         1
         MetAlaThrGlyValAlaGluGluArgLeuArgLeuAlaAlaLeuAlaTyrL
         CCCTGGGCAACGGCGACGGCGAGGAGCGCCTGCGGCTGGCCGCGCTGGCCTACC
yrGlyArgHisAlaLeuProSerHisArgLeuArgValProAlaArgAlaAlaTrpValValG
ACGGGCCACGCGCTGCCCAGCCACAGGCTCCGAGTGCCGGCGCGGGCCGCCTGGGTGGTGC
         98
rgLeuArgSerAlaProAsnCysIleLeuLeuAlaMetPheLeuValHisTyrGlyHisAr
GTCCGCAGCGCCCCCAACTGCATCCTCCTGGCCATGTTCCTCGTCCACTACGGGCATCG------>14 kb
                                                  gCysLeu
CCGACCCTCCCCTCACTGCCCGGTGCCCTCTCCCCGAAGCCTCCCCCACC---------GTGCTTA
TTATCTTTAATTTTTAAAAAATTGTGCCTGTTTCTGTTTCCTAAG---------
```

FIG. 10B

```
GGAACCGCCCCCTCGCCGCCGCCTCGCAGGCCTCGGTGTCCGGGAAGCCCAGGAGGA         -729
GCGCCATCCTCCGGTCCTCCGGCCGTGTGTTGCTGTGGAGCCGCGACCCCGCGAC           -609
ACTCTAGCCCTACACCTCCGGGACTTCCGGCCGGAAACCAAGGCCCCACGTCCG            -489
CTTTCAGAAAAGCGGGCGTGACAGGGAAAAACAGGAACAGTCTAAGGGGAAAAAAAT         -369
AGGAGCTCCGCGGACAGCCTGAAGCCGCGTGCGCAGAGCGGGCGGGGTTACTGC            -249
GGCCGCACCCACAGCCCCCGGCTACCCCGGAGAAGCCTGACTGAGAACCCTTTCTGC         -129
GCCGCCGCCCTATATGTTGCCCGCCGCCTCGGGCATGGAGCACGCTGCCCAG              -9
```

```
        euGlnCysAlaValGlyCysAlaValValPheAlaArgAsnArgGlnThrAsnSerValT
        TGCAGTGCGCCGTGGGCTGCGCGGTCTTCGCGGCGAATCGTCAGAGGAACTCAGTGT
```

```
lnGluLeuProSerLeuAlaLeuProLeuTyrGlnTyrAlaSerGluSerAlaProA
TGCAGTTGCCCTCGCTGGCCCTGCCGCTCTACCAGTACGCCAGCGAGTCCGCCCCGC
```

```
AGGAGCTGCCCTCGCTGGCCCTGCCGCTCTACCAGTACGCCAGCGAGTCCGCCCCGC
```

```
--------GTAACGTCCCCCGGGCCCCCGCCCCTACCCTACTCCCCGGCCCCGGGCGTCCTCT
```

```
----CAAGAAAGTAAGATTTAAACCCAAATCATTTAAGATAGGATTACAGAAATGA
```

```
IleTyrProPheLeuMetArgGlyGlyLysProMetProLeuLeuAlaCysThrMet
ATTTACCCGTTTCTGATGCGAGGAGGAAAGCCTATGCCACTGTTGG(A)TGTACAATG
```

FIG.10C

```
AlaIleMetPheCysThrCysAsnGlyTyrLeuGlnSerArgTyrLeuSerHisCysAlaVal
GCGATTATGTTCTGTACCTGTAACGGCTATTGCAAAGCAGATACTTGAGCCATTGTGCAGTG
TCCACAGCAGTGAACTCCGCCTTGTTCACATCATTGCTTTTATATTGATGTCCCAGTGGTT-----
                                                             188

GCTCGTAGTGAAATTTACGGTTATTAGCCATAATCATCTTGCAATTTTTTCCTTTAG-----
eLeuArgAsnLeuArgLysProGlyAspThrGlyTyrLysIleProArgG
CCTAAGGAATCTCAGAAACCAGGAGATACTGGATACAAAATACCAAGGG------GTACG lyGlyLeuPheGluTyrV
GTTGCCAGCTCTAAGAAGTAGTAGCGTAGTAGTTATTA------ 6.6 kb ------TCTTGA
AGTAAATGCACTACTTTGGTCTCTGTGTTTTCTCTAG--------------------GAGGCTTATTGAATACG erTrpSerValGlnGlyAlaAlaPhePheThrPheCysPheLeuSerGlyArgAlaL
GCTGGTCTGTCCAAGGCGGGGCTTTGCTTTCTCACGTTTGTTTTTATCTGGTAGAGCAA
TTCTTTGACTATATTATTACCATTTTCAGGCTAGATTTTTGAAGTGTTAATTAAATCGCTG

TGTTAGCATTGGTTAAATGTCTAAGCGACAGAATTATTCCTTTTTAATTTTTTTCTTAG-----
                     259
leIleProPheLeuPhe***
TAATTCCATTTTTGTTTTAAGTGGCGTTTTTCATGAAATTATCTTCAACTTGAAGCTTT-----
```

FIG. 10D

```
                                          154
TyrAlaAspAspTrpValThrAspProArgPheLeuIleG
TATGCTGATGACTGGGTAACAGATCCCCGTTTTCTAATAG-------GTGAGTG

---- 3.9 kb ----AATCTGAAGGGTTGCAATAATACTAGTTCAGTCAGGCTGGG lyPheGlyLeuTrpLeuThrGlyMetLeuIleAsnIleHisSerAspHisIl
-------GTTTTGGCTGTGGGTTAACAGGCATGTTGATAAACATCCATTCAGATCATAT

TACAGAAAGTGAAGAATTTCTGTGAAAGTTGCTTGCCATGGTTCCTGGCTATTTGT

ATTTATGTCTCCAGGTAAGTATTCACTAGCATCTCTGAAGTCCGTATTCATTTGT aThrAlaAlaAsnTyrPheGlyGluIleMetGluTrpCysGlyTyrAlaLeuAlaS
TAACTGCAGCCAACTATTTTGGAGAAATCATGGAGTGGTGTGGCTATGCCCTGGCCA
                        238
ysGluHisHisGl
AAGAGCATCATGA-------GTAAGTTTTAAAACACTTTTACCATTGTAATTG

AA------ >7.0 kb ----ACTGAGTACTCTTTTGTAATGAAAAATATGTCATTT uTrpTyrLeuArgLysPheGluGluTyrProLysPheArgLysIleI
-------GTGGTACCTCCGGAAATTGAAGAGTATCCAAAGTTCAGAGAAAATTA

Exon 5 (1.3kb).
```

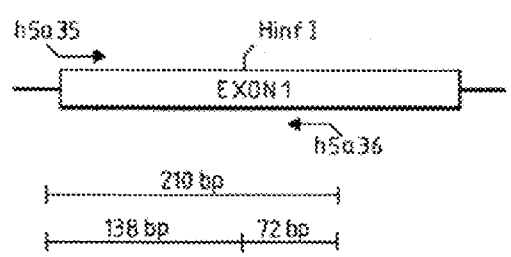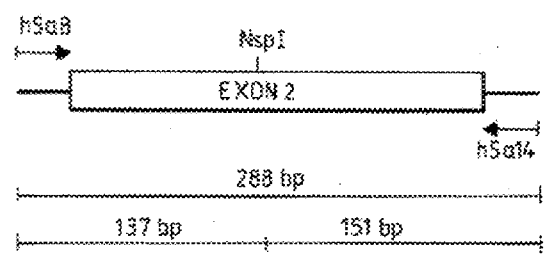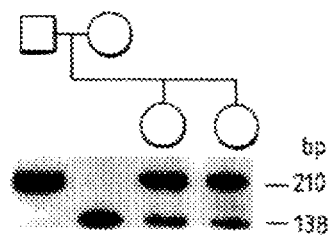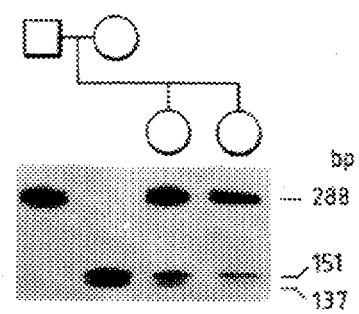
FIG.12A                    FIG.12B

FIG.13A

```
          MetGlnValGlnCysGlnSerProValLeuAla
GCGGCCACCGGGCGGAGGAACACGGGCGCGATGCAGGTTCAGTGCCAGAGCCCAGTGCTGGCA
                                    10

GlyTyrGlyLysHisThrGluSerLeuLysProAlaAlaThrArgLeuProAlaArgAlaAla
GGCTACGGGAAGCACACGGAGAGCCTGAAGCCGGCTGCCACCCGCCTGCCAGCCCGCGCCGCC
            40                                  50

ProLeuSerLeuPheGlyProProGlyThrValLeuLeuGlyLeuPheCysValHisTyrPhe
CCCCTCTCCCTCTTCGGGCCACCTGGGACCGTCCTCCTGGGCCTCTTCTGCGTACATTACTTC
                        80                                  90

IleLeuArgGlyThrAlaPheCysThrGlyAsnGlyValLeuGluGlnGlyTyrTyrLeuIleTyr
ATTCTCAGAGGCACTGCCTTCTGCACTGGAAATGGAGTCCTTCAAGGCTACTATCTGATTTAC
            120                                 130

LeuPheIleLeuGlyMetGlyIleLeuAsnIleHisSerAspTyrIleLeuArgGlnLeuArgLys
TTATTTATTTTGGGAATGGGAATAAACATTCATAGTGACTATATTGCGCAGCTCAGGAAG
                        160                             170

AlaAsnPheLeuGlyGluIleIleGluTrpIleGlyTyrAlaLeuAlaThrTrpSerLeuPro
GCCAATTTCCTCGGTGAGATCATTGAATGGATCGGCTATGCCCTGGCCACTTGGTCCCCA
            200                                 210

HisArgPheTyrLeuLysMetPheGluAspTyrProLysSerArgLysAlaLeuIleProPhe
CATAGGTTCTACCTCAAGATGTTTGAGGACTACCCCAAATCTCGGAAAGCCCTTATTCCATTC
                        240                             250
```

FIG.13B

```
        GlySerAlaThrLeuValAlaLeuGlyAlaAlaLeuTyrValAlaLysProSer
        GGCAGGCCACTTTGGGTCGCCCTTGGCACTGGCCTTGTACGTCGCGAAGCCCTCC        120

TrpPheLeuGlnGluLeuProSerPheAlaValProAlaGlyIleLeuLeuAlaArgGln
        TGGTTCCTGCAGGAGCTGCCTTCCTTCGCGGTGCCCGCGGGGATCCTCCTCGCCCGGCAG    240

HisArgThrPheValTyrSerLeuLeuAsnArgGlyArgProTyrProAlaIleLeu
        CACAGGACATTTGTGTACTCACTGCTCAATCGAGGGAGGCCTTATCCAGCTATACTC      360

CysAlaGluTyrProAspGlyTrpTyrThrAspIleArgPheSerLeuGlyValPhe
        TGTGCTGAATACCCTGATGGGTGGTACACAGACATACGGTTTAGCTTGGGTGTCTTC      480

ProGlyGluIleSerTyrArgIleProGlnGlyGlyLeuPheThrTyrValSerGly
        CCTGGAGAAATCAGCTACAGGATTCCACAAGGTGGCCTTGTTTACGTATGTTTCTGGA    600

AlaAlaAlaPheAlaPheSerLeuCysPheLeuLeuGlyLeuArgAlaPheHisHis
        GCACTTGCATTTGCATTTTCACTTTGTTTCCTTGGGCTGCGAGCTTTTCACCAC          720

IlePhe***
        ATCTTTTAAAGGAACCAAATTAAAAAGGAGCAGAGCTCCCACAATGCTGATGAAAAC       840
```

FIG.13C

TGTCAAGCTGCTGAAACTGTAATTTCATGATATAATAGTCATATATATATATATATATAT

GCCTGGGATTCTGAGTGGTGTCTGCTTAGAGTTTACTCCTACCCTTCCAGGACCCTATCC

AGCTATTGCTCTGAGAAAGTACAAACTTCTCCTATGTCTTTCACCGGGCAATCCAAGTACATG

ACTTGAAGGCAGTACTTATAGACCTTATTAAAGGTATGCATTTTATACATGTAACAGAGTAGC

CCCCAGTCATGGCTTCCTTTTCTTGGTTAAATTAGGAAAGATGAGAAATTATTAGGTAGACCT

TTCAAATTGTGCAGTGTCTTAGTGTGATGAGTGCCTCTGTTTCCAGAAGATTTCACAATCCC

GCATGAACCTGGGTGGCTTATGAGAGAGTAGAGAACAACATGACCCTGGATGGCTACTAAGAG

GCAATATCCAAATAATGAGTAGTGTAAAACAAGAGAATTAATGATGAGGTTACATGCTGCTT

CTTTCCTGGAGCTTCTTCCTGTAGTTCTCAGGACCTGTTCAAGAAGGTGTCTCCTAGGGCA

GGCACGTCTGGGCAGAAAACCTGTTTGTTGGCTCAGACATATAGTTTTTTTTTTTTACAA

CATTAAAAAGTTGGAGGATCTGAACATAGAGCCCCACATTTCCACACCAGAACTGGAACTA

GTGCTGAGATATGGACTCTCTAAGGAAGGGGCCGAACGCTTGTAATTGGAATACATGAAATA

TGACAAATGAGCACCAGTGGTACTAAGCACAGAAACTCACTATATAAGTCACATAGGAAACTT

AGTGTTTTGTTGTTCATTAAATACCTTTAAATCATG(A)$_N$  2437

FIG. 13D

```
ATATATATATATATGTATATATGTAATAGTAGGTCTCCTGGCGTTCTGCCAGCTG       960
TGATCCCCAACTGAAGCTTCAAAAGCCACTTTTCCAAATGGCGACAGTTGCTTCTT     1080
TGGCTTCATACCCACTCCCTGTCAATGCAGGACAACTCTGTAATCAAGAATTTTTG     1200
AGAAATTTAAACTCTGAAGCCACAAAGACCCAGAGCAAACCCACTCCCAAATGAAAA    1320
TGAATACAGGAGCCCTCTCCTCATAGTGCTGAAAAGATACTGATGCATTGACCTCAT    1440
CGGAAAACTGGTATGGCTATTCTTGAAGGCCAGGTTTAATAACCACAAACAAAAAG    1560
GATAGAGAACAGTTTACAATAGACATTGCAAACTCTCATGTTTTGGAAACTGGTG     1680
GCCTCCACCAGATGTCCACAACAATATGAAGTACAGCAGAAGCCCCAAGCAACTTTC    1800
GCCTGAATGCCCTCCCTCAAAGGACCTGCAGGCAGAGACTGAAAATTGCAGACAGAGG   1920
AGTTTCAAAAACTTAAAAATCAGGAGATTCCTTCATAAAACTCTAGCATTCTAGTTT    2040
CGTAGCTAGTAAGCATTTGAGTTTGCAAACTCTTGTGAAGGGTCACCCCAGCATGA     2160
TTGTCTTCTCAGGCCTATGTTTGCGGAATGCATTGTCAATATTTAGCAAACTGTTT     2280
GAAAGGTCTGAGGATGATGTAGATTACTGAAAAATACAAATTGCAATCATATAAATA    2400
```

FIG. 14

```
                                                                          63
m 5α-red 2  MQVQCQQSPVLAGSATLVALGAIALYVAKPSGYGKHTESLKPAATRLPARAAWFLQELPSFAV
m 5α-red 1  MATATGVAEERLLAALAYLQCAVGCAVFARNRQTNSVVYGRH--ALPSHRLRVPARAAWVVQELPSLAL
t 5α-red 1         MELDELCLLDMLVVLEGFMAFVSIVGLRSVGSPYGRYSPQWP--GIRVPARPAWFIQELPSMAW 129
m 5α-red 2  PAGILARQPL-SIFGPPGTVLLIGLFCVHYFHIRTLFVYSILLNRG-RPYPAILILRGTAFCTGNGVLQGYY
m 5α-red 1  PLYQQASESAPRLIRSAPNCILLAMFLVHYGHRQLIYPFLMRGGKPMPLLLACTMAIMFCTQNGYLQSRY
t 5α-red 1  PLYEYIRPAAARLGNLPNRVLLAMFLIHYVQRTLVFPVLIRGGKPTLLVTFVLAFLFCIFNGYVQSRY 197
m 5α-red 2  LLIYCAEYPDQWYTDIRFSLGVFLFIILGMGININIHSDYILRQLRKPGELSYRIPQGGLFIYVSGANFLGE
m 5α-red 1  LSHCAVYADDWVTDPRFLIGFGLWLTGMLININIHSDHILRNLRKPGDTGYKIPRGGLFEYVTAANYFGE
t 5α-red 1  LSQFAVYAEDWVIHPCFLIGFALWLVGMVININIHSDHILRNLRKPGETGYKIPRGGLFEYVSAANYFGE 254
m 5α-red 2  IIEWLGYALALWSLPALAFAFFSICFLGLRAFHHHRFYLKMFEDYPKSRKALIPFIIF
m 5α-red 1  IMEWCGYALASWSVQGAAFAFFTECFLSGRAKEHHEWYLRKFEEYPKFRKIDIPFLF
t 5α-red 1  LVEWCGFALASWSLQGVVEALFTLSTLLTRAKQHHQWYHEKFEDYPKSRKILIPFVL
```

FIG. 17A

```
                                                                                              .
TCTAGAACTGGAAATACCATTTGACCCAGCCATCCCATTACTG
                                                                                              .
TTTATTGTGCACTATTCACAATAGCAAAGACTTGGAAACAACCAAATGTCCAACAATGATA
                                                                                              .
AATGATGAGTTCATGTCCTTTGTAGGACATGGATGAAATTGGAAATCATTCTCAGCAAA
                                                                                              .
AACAATGAGAACACAGGACACAGGAAGGGAACATCACACTCTGGGGACTGTTGTGGGGTGG
                                                                                              .
GGGTGCAGCACCAGCATGGCACACATGTATACATATATAACTAACCTGCACATTGTGCACATG
                                                                                              .
TATCTCTACATACTGCCAAAAAAAAAAAAAAGATTCAGATCACTCCCCGCCCCCGC
                     LINE SEQUENCE
                 ←――――――――――――→
                                              .                      .
                                             10                      20
   MetAlaThrAlaThrAlaValValGluGluArgLeuLeuAlaAlaPheAlaAlaTyrLeu
 1 ATGGCGACGGCGACGGCGGTGGTGGAGGAGCGCCTGCTGGCTGCGTTCGCCTACCTT
                                              .                      .
                                             50                      60
   SerArgHisAlaProProSerArgArgArgAlaArgValProAlaArgAlaThrArgValValGln
41 AGCCGGCACGCGCCACCGAGCCGCAGGCTCCGAGTGCCGGCGGGGCCACCCGGGTGGTGCAG
```

FIG. 17B

```
GGTATATACCCAAAGGACTATAAATCATGCTGCTATAAAGACACATGCACACGTATG          100
GACTGGATTAAGAAAATGTGGCACATATACACCATGGAATACTATGCAGTCATAAAA          220
CTATCACAAGGACAAAAAACCAAACACCGCATGTTCTCACTCATAGATGGGAACTG           340
GGGGAGGGGGAGGGTTAGCATTAGGAGATATACCTAAATGCTAAATGACGAGTTAAT          460
TACCCTAAAACTTAAAGTATAATAATTAAAAAGAAAAAAGAATAAAGAA                  580
CCTATATGTTGCCTGCCTCGGCCCTCGGCCTCGGGGCATGGAGCACGCGGCCCTGGCG         700
                                         30              40
                            GlnCysAlaValGlyCysAlaValPheAlaArgAsnArgGlnThrAsnSerValTyr
                            CAGTGCGCCGTGGGCTGCGCGGTCTTCGCTCGGAATCGTCAGAGAACTCAGTGTAC        820
                                                         70              80
                            LysLeuProSerLeuAlaLeuProLeuTyrGlnTyrThrSerGluSerThrProArg
                            AAGCTGCCCTCACTGGCCCTGCCCCTCTACCAGTACACCAGTGAGTCCACCCCGCGC       940
```

FIG. 17C

```
 81                          90                          100
LeuArgSerAlaProSerCysIleLeuLeuAlaMetPheLeuAlaHisValHisTyrTrpHisArgCys
CTCCGCAGCGGCGCCCAGCTGCATCCTCCTGGCCATGTTCCTCGTCCACTACTGGCATGGGTGC 121                         130                         140
MetAlaIleMetPheCysThrCysAsnGlyTyrLeuGlnSerArgTyrLeuSerHisCysAla
ATGGCGATTATGTTCTGTACCTGTAATGGCTATTTGCAAAGCAGATACTTGAGCCATTGTGCA 161                         170                         180
LeuThrGlyMetLeuIleIleAsnIleSerAspHisIleLeuArgAsnLeuArgLysAlaGly
TTAACGGGCATGTTGATAAACATCAGATCATATCCTAAGGAATCTCAGAAAAGCAGGA 201                         210                         220
TyrPheGlyGluIleMetGluTrpArgGlyTyrAlaLeuAlaSerTrpSerValGlnGlyAla
TATTTTGGAGAAATCATGGAGTGGCGTGGCTATGCCCTGGCCAGCTGGTCTGTCCAAGGCGCG 241                         250                         260
ArgTyrLeuArgLysPheGluGluTyrProLysPheArgLysIleIleIleProPheLeuPhe
CGGTACCTCCGGAAATTTGAAGAGTATCCAAAGTTCAGAAAAATTATAATTCCATTTTTGTTT

TGCTTTAAAAAAAGATTCAGATCACAGCTTCTTCTTCATTGGGAGAACGGGCACTCAGTCT
                       —————————————————————→
```

FIG. 17D

```
                    110                           120
LeuIleTyrProPheLeuMetArgGlyGlyLysProValProLeuLeuAlaCysThr
TTAATTTACCCATTTCTGATGGCGAGGAGGAAAGCCTGTGCCACTGTTGGCGTGCACA
                                         .                      .                      .
                    150                           160
ValTyrAlaAspAsp***ValLysAspAspProArgPheLeuIleAsnPheGlyLeuTrp
GTGTATGCTGATGAC TGAGTAAAAGATCCCCGTTTTCTAATAAATTTTGGCTTGTGG
                                         .                      .                      .
                    190                           200
AspThrGlyTyrLysIleProArgGlyGlyLeuPheGluTyrIleThrAlaGlyAsn
GATACTGGATACAAAATACCAAGGGGAGGCTTATTTGAATACATAACTGCAGGCAAC
                                         .                      .                      .
                    230                           240
ThrPheAlaPhePheThrPheCysPheLeuSerGlyArgArgAlaLysGluHisHisGlu
ACTTTTGCTTTCTTCACATTTTGTTTTTTATCTGGTAGAGCAAAAGAGCATCATGAG
                                         .                      .                      .
*** 
TAA GTGCATTTTTCACGAAATTACCTTCAACTTGAAGCTT......-1.14kb......

GCTCTGCATGGAAACCAACGTCTTTGCTCATTCACATGTGCATTCTTGGGCATCTTT
```

1060

1180

1300

1420

1523

STEROID 5A-REDUCTASES

This is a divisional of application Ser. No. 07/795,859, filed Nov. 18, 1991 U.S. Pat No. 5,422,262, which is a continuation-in-part of application U.S. Ser. No. 07/517,661, filed 30 Apr., 1990, now abandoned.

The U.S. government may own certain rights in the present invention pursuant to NIH grants GM-43753, GM08014, and DK-07307.

BACKGROUND OF THE INVENTION

1. Field of the Invention

The present invention relates generally to enzymes, termed steroid 5α-reductases, which function biologically to catalyse the conversion of testosterone to dihydroxytestosterone. Accordingly, the invention relates to the preparation of this enzyme from various sources by recombinant techniques, to nucleic acid segments which encode the enzyme or which can be used as probes for the selection of related sequences, as well as to assay methods for the identification of candidate substances which will affect the activity of the enzyme. The present invention is particularly directed to nucleic acid segments which encode the major steroid 5α-reductase isozyme in human genital tissue, to its preparation by recombinant techniques, and to assay methods for the identification of substances affecting the activity of this isozyme.

2. Description of the Related Art

The enzyme steroid 5α-reductase is a microsomal protein that plays a central role in human sexual differentiation and androgen physiology. Interest in this protein arises from several distinguishing characteristics. Firstly, steroid 5α-reductase catalyzes the conversion of testosterone into the more potent androgen dihydrotestosterone (Wilson, 1975). This latter steroid induces a program of differentiation during embyrogenesis that leads to the development of the male external genitalia (Wilson, 1978). Secondly, mutations in the gene for steroid 5α-reductase give rise to a rare form of male pseudohermaphroditism in which affected males develop normal internal urogenital tracts but fail to develop external male structures (Griffin et al., 1989). Thirdly, the expression of the gene is regulated by androgens in tissues such as the prostate and liver (Anderson et al., 1989a). A fourth distinguishing feature of steroid 5α-reductase is its role in several endocrine abnormalities including benign prostate hyperplasia, male pattern baldness, acne, and hirsutism (Wilson, 1980; Mooradian et al., 1987; Cunha et al., 1987).

It is this fourth role which has led researchers towards the development of agents that will serve to inhibit the enzyme, with the hope that such agents will prove useful in the treatment of one or more of these conditions. Since the product of steroid 5α-reductase activity, dihydrotestosterone, is involved in inducing these and perhaps other conditions, it is believed that by inhibiting steroid 5α-reductase action, one can ameliorate one or more aspects of the particular condition. The drugs which have been used a therapeutic agents include principally 4-azasteroid derivatives such as MK-906 (Finasteride) and 4-MA (Brooks et al., 1981; Vermeulen et al., 1989) that function as competitive inhibitors of the enzyme (Liang et al., 1985). The exact mechanism by which these compounds act in vivo has yet to be elucidated.

While these competitive inhibitors of steroid 5α-reductase have shown some promise, e.g., in the treatment of benign prostatic hyperplasia, in general, these agents appear to suffer from a variety of problems and potential drawbacks, including limited efficacy and even hepatotoxicity. Furthermore, the development of additional inhibitors has been greatly hampered due to the previous lack of a useful, relatively simple test system which can be used to screen for new inhibitors.

The previous lack of knowledge in the art concerning steroid 5α-reductases has hampered the development of new therapeutic agents. For example, prior to the present invention, it was not known whether a single steroid 5α-reductase enzyme was present in different tissues, such as liver and prostate. Furthermore, knowledge concerning the structure and properties of steroid 5α-reductase was very limited. Efforts to further characterise the enzyme have been hampered by the very low levels of reductase expression in most tissues, even in tissues which are responsive to androgens and by the poor solubility of the protein (Liang et al., 1985; Fisher et al., 1978; Moore et al., 1975).

Accordingly, if medical science is to succeed in the development of novel and more efficacious steroid 5α-reductase inhibitors, there is a great need to expand our knowledge of this enzyme. There is a considerable need to provide means for preparing improved compositions of biologically active human steroid 5α-reductase, particularly the form active in genital tissues, which can be employed in studies to further our understanding of the enzyme. Moreover, this would facilitate the development of improved highly sensitive and rapid screening protocols to identify those compounds, from a large panel of candidate substances, which affect the function of the enzyme. The availability of a genital tissue-specific steroid 5α-reductase would allow a more detailed analysis of the effective concentrations and kinetic parameters of active compounds identified in a preliminary screening protocol. Furthermore, the availability of genes encoding steroid 5α-reductases would greatly facilitate the development of diagostic assays for alterations in the genes that affect dihydro testosterone formation.

SUMMARY OF THE INVENTION

The present invention concerns, in a general sense, compositions and methods for the synthetic preparation of steroid 5α-reductase, including different human isozymes and the enzyme from the rat and even other mammals such as the cow, pig and the like, as well as their biological functional equivalents, and to methods employing these species in the identification of candidate substances capable of inhibiting or otherwise modifying their enzymatic function.

In certain general and overall embodiments, therefore, the invention concerns recombinant vectors and isolated DNA segments encoding a steroid 5α-reductase. DNA segments of the invention may also encode biologically functional equivalent proteins or peptide which have variant amino acids sequences, such as species which incorporate changes based on considerations such as the relative hydropathic score of the amino acids being exchanged.

As used herein, the term "DNA segment" in intended to refer to a DNA molecule which has been isolated free of total genomic DNA of a particular species. Therefore, a DNA segment encoding a steroid 5α-reductase is intended to refer to a DNA segment which contains such coding sequences yet is isolated away from total genomic DNA of the species from which the DNA is obtained. Included within the term "DNA segment", are DNA segments which may be employed in the preparation of vectors, as well as the vectors themselves, including, for example, plasmids, cosmids, phages, viruses and the like.

In the context of the present invention, the term "steroid 5α-reductase" is intended to refer to any protein or peptide having the biological or immunological identity, or both, of a steroid 5α-reductase enzyme as exemplified, e.g., by naturally occurring steroid 5α-reductase enzymes from species such as human, rat or other mammalian species, or functional equivalents.

In particular embodiments, the invention concerns recombinant vectors and isolated DNA segments incorporating DNA sequences which encode a steroid 5α-reductase that includes within its amino acid sequence the amino acid sequence of either FIG. 4, or FIGS. 7 or 13, (SEQ ID NOS: 2, 4, and respectively) corresponding to rat type 1 and human types 1 and 2 steroid 5α-reductases, respectively. Important aspects of the present invention concern recombinant vectors and isolated DNA segments that encode a steroid 5α-reductase type 2 that includes, or is functionally equivalent to, the amino acid sequence of FIG. 13, (SEQ ID NO: 6) which represents a major functional steroid 5α-reductase active in human genital tissue.

The recombinant vectors and isolated DNA segments of the present invention may variously include the human or rat steroid 5α-reductase coding regions themselves, coding regions bearing selected alterations or modifications in the basic coding region or may encode larger proteins which nevertheless include sequences which will confer steroid 5α-reductase activity. Furthermore, and in any event, it should be appreciated that due to codon redundancy and functional equivalency this aspect of the invention is not limited to the particular DNA sequences shown in FIGS. 4, 7 or 13 (SEQ ID NOS: 1, 3 and 5 respectively).

Recombinant vectors such as the foregoing are useful both as a means for preparing quantities of the enzyme, and as a means for preparing shorter peptides. It is contemplated that where steroid 5α-reductase proteins of the invention are made by recombinant means, one may employ either prokaryotic or eukaryotic expression systems.

Where expression of a steroid 5α-reductase enzyme in a host is contemplated, it may be desirable to employ a vector, such as a plasmid, that incorporates an origin of replication, as exemplified by the eukaryotic vectors of the pCMV series, like pCMV4. Additionally, for the purposes of expression in host systems, one will desire to position the coding sequences adjacent to and under the control of an effective eukaryotic promoter, such as an SV40 or CMV promoter in eukaryotic systems. To bring a coding sequence under the control of such a promoter, whether it be a eukaryotic or prokaryotic promoter, all that is generally needed is to position the 5' end of the transcription initiation site of the transcriptional reading frame of the protein between about 1 and about 50 nucleotides "downstream" of (i.e., 3' of) with respect to the promoter chosen.

Furthermore, where host expression is contemplated, one will typically desire to incorporate into the transcriptional unit which includes the enzyme, an appropriate polyadenylation site (e.g., 5'-AATAAA-3') in eukaryotes, or a transcriptional terminator in the case of prokaryotes. Typically, the poly A addition site is placed about 30 to 2000 nucleotides "downstream" of the termination site of the protein at a position prior to transcription termination. A similar positioning of the prokaryotic terminator is also typical.

Useful eukaryotic vectors which include all of the foregoing, and into which the gene of the present invention can be inserted with little difficulty, will be known to those of skill in the art in light of the present disclosure. For example, suitable eukaryotic vectors include pCD and pCMV, with the most preferred system being pCMV. In addition to pCD and pCMV vectors, other preferred eukaryotic expression vectors include pMSG and pSVL from Pharmacia LKB Technology, Piscataway, N.J. These utilize the MMTV and SV40 late promoters, respectively. A DNA, such as shown in FIGS. 4, 7 or 13, (SEQ ID NOS: 1,3 and 5 respectively) can readily be inserted into one of the foregoing vectors via the EcoRI restriction site "upstream" of (i.e. 5' of) the initiation codon (ATG) that begins translation of the encoded enzyme.

It is contemplated that virtually any of the commonly employed eukaryotic host cells can be used in connection with steroid 5α-reductase expression in accordance herewith. Examples include cell lines typically employed for eukaryotic expression such as AtT-20, HepG2, VERO, HeLa, CHO, WI 38, BHK, COS-7, RIN and MDCK cell lines. Preferred lines for use in eukaryotic expression embodiments of the present invention are COS cells such as COSM6 and COS-7 and human embryonal kidney 293 cells. Of course, where eukaryotic hosts are employed, it is known that recombinant sequences may be either maintained extrachromosomally, or may be actually incorporated or integrated into the genome of the host cell. For long term expression, it will generally be preferred to employ systems wherein genomic integration is achieved, such as CHO or HepG2. However, where mere transient expression is desired, such as for recombinant screening purposes, extrachromosomal transformation may be sufficient, such as exemplified by COS-7 or HeLa cells.

Prokaryotic expression is an alternative which can be employed where desired. Typically, prokaryotic promoters which may be employed include $P_L$, T7 and lac promoter, with T7 being generally preferred. Other preferred bacterial expression vectors include plasmid pKK233-2 and pKK233-3, available from Pharmacia LKB Technology. These utilize the tac and trc promoters, respectively.

Of course, even where a eukaryotic hook-up and expression is used, one will nevertheless usually desire to include a prokaryotic origin of expression, as well as selective markers operable in prokaryotic systems, to allow "shuttling" of sequences from construction in prokaryotic to expression in eukaryotic.

In certain embodiments of the invention it is contemplated that DNA fragments both shorter and longer which incorporate sequences from FIGS. 4, 7 or 13 (SEQ ID NOS: 1, 3 and 5, respectively) will find additional utilities, including uses in the preparation of short enzymatically active peptides or even as short DNA fragment hybridization probes for use, e.g., in screening clone banks. It is further contemplated that DNA fragments incorporating sequences from FIGS. 10 and 17, (SEQ ID NOS: 7, 9–11, 13–15, 17–19, 21–23, 25, and 27, respectively) which represent a steroid 5α-reductase gene and pseudogene may be also find utility as DNA hybridization probes. In any event, fragments corresponding to the FIGS. 4, 7, 10, 13 or 17 (SEQ ID NOS: 1, 3, 7, 9–11, 13–15, 17–19, 21–23, 5, 25, and 27, respectively) sequences for stretches of as short as 10 or so nucleotides, will find utility in accordance with these or other embodiments. By having stretches of at least about 10 to 20 nucleotides in common with the disclosed DNA sequence of FIG. 4, 7, 10, 13 or 17, (SEQ ID NOS: 1, 3, 7, 9–11, 13–15, 17–19, 21–23, 5, 25, and 27, respectively) or its complement, a DNA segment will have the ability to form a preferential hybrid with steroid 5α-reductase DNA, particularly under more stringent conditions such as 0.15M NaCl and 0.02M sodium citrate pH 7.4 at 50° C. While a complementary or common stretch of about 10 or so nucleotides will ensure the ability to form a stable hybrid, longer stretches of complementarity may prove more desirable for certain uses. Thus, one may desire to use certain DNA segments incorporating longer stretches of complementarily, for example, on the order of 18, 22 or even 25 or so bases.

An important aspect of the invention concerns a method for the production of steroid 5α-reductase by recombinant means, as well as use of the recombinantly produced enzyme in screening assays. Screening assays of the present invention will generally involve determining the ability of a candidate substance to affect the enzymatic activity of the enzyme, such as the screening of candidate substances to identify those that will inhibit or otherwise modify its enzymatic function. Typically, this method will include recombinantly preparing steroid 5α-reductase, followed by testing the recombinant steroid 5α-reductase with a candidate substance to determine the ability of the substance to affect its enzymatic function.

In preferred embodiments, the invention relates to the screening of candidate substances to identify those that affect the enzymatic activity of the human enzyme, and thus may be suitable for use in humans. Accordingly, in such embodiments, the use of human steroid 5α-reductase, and more preferrably, the genital isozyme steroid 5α-reductase 2, is contemplated.

In a typical screening assay for identifying candidate substances, one may desire to employ the same recombinant expression host as the starting source for obtaining the enzyme, generally prepared in the form of a crude homogenate. Recombinant cells expressing the enzyme may be washed and homogenized to prepare a crude protein homogenate in a desirable buffer such as disclosed herein. In a typical assay, an amount of protein from the cell homogenate, such as 10 to 50 μg of cell homogenate protein, is placed into a small volume, e.g., 0.5 ml, of an appropriate assay buffer, such as 0.1M potassium phosphate, or 0.1M Tris-Cl, or 0.1M Tris citrate, at an appropriate pH (e.g. pH 6.6, rat enzyme; pH 7.0, human Steroid 5α-reductase 1; pH 5.0 to 5.5 human steroid 5α-reductase 2). Steroid substrates, such as testosterone, progesterone or androstenedione, are added to the admixture in convenient concentrations, such as, e.g., 0.1 to 20 μM, and the reaction allowed to initiate by the addition of the cofactor NADPH.

Where one uses an appropriate known substrate for the enzyme, one can, in the foregoing manner, obtain a baseline activity for the recombinantly produced enzyme. Then, to test for inhibitors or modifiers of the enzyme function, one can incorporate into the admixture a candidate substance whose effect on the enzyme is to be tested. By comparing reactions which are carried out in the presence or absence of the candidate substance, one can then obtain information regarding the effect of the candidate substance on the normal enzymatic function of the enzyme.

In preferred assays, the enzymatic function is measured by simply measuring the amount of product produced, or substrate used up, in the experimental reaction versus the control over a period of time. One may find it of benefit, therefore, to measure the rate at which a particular substrate is used, or product appears. In any event, the inventors have found that a convenient method for measuring the disappearance of substrate or appearance of product is through the use of a labeled substrate, such as a radioactively labeled substrate. In this manner, reaction products may be separated by chromatographic means, such as thin layer chromatography, HPLC or the like, and the relative amounts of the materials determined by scintillation counting.

While the foregoing approach has been found to work well by the inventors, there is no reason why other approaches might be employed, so long as one is able to determine whether a candidate substance has the ability to modify, alter or inhibit the enzyme being tested. Possible examples include spectrophotometric, gas chromatographic/mass spectrophotometric or even using NMR analyses.

Accordingly, it is proposed that this aspect of the present invention will provide those of skill in the art with methodology that will allow for the identification of candidate substances having the ability to modify the action of steroid 5α-reductases in one or more manners.

BRIEF DESCRIPTION OF THE DRAWINGS

FIGS. 7A–7D. cDNA sequence and predicted amino acid (SEQ ID NOS: 3 and 4 respectively) sequence of human steroid 5α-reductase 1. Nucleotides are numbered on the right with dots placed below the sequence every tenth nucleotide. Amino acid residues are numbered above the protein sequence. A potential polyadenylation signal (AATAAA) is overlined.

FIG. 10A–10D. Structure of human steroid 5α-reductase 1 gene (SRD5A1). The DNA sequence of the 5'-flanking region, the exons, and the intron regions immediately adjacent to the exons (SEQ ID NOS: 7, 9–11, 13–15, 17–19, and 21–23, respectively) are shown. Only a portion of the DNA sequence of exon 5 corresponding to the 3'-untranslated region of the mRNA is shown. The remainder of this sequence is detailed in FIG. 7(SEQ ID NO: 3). Two polymorphic nucleotides in exon 1 and exon 2 are circled. A TATA sequence in the 5'-flanking region of the gene is overlined. Amino acids in the coding region (SEQ ID NOS: 8, 12, 16, 20, and 24, and respectively) are indicated and numbered above the DNA sequence. Nucleotides in the 5' -flanking region are assigned negative numbers beginning with the base immediately upstream of the A of the ATG initiation codon.

FIG. 12A–12B. Restriction fragment length polymorphisms in human steroid 5α-reductase 1 gene (SRD5A1). Left: HinfI polymorphism in exon 1. Genomic DNAs derived from members of a small family were amplified with the oligonucleotides h5a35 and h5a36 to produce a 210 bp fragment corresponding to a region of exon 1. A portion (10%) of the amplification reaction was digested with HinfI, electrophoresed on a neutral polyacrylamide gel, transferred to a nylon filter by electroblotting, and probed with [$^{32}P$] labeled h5a35. If the HinfI site is present, then the 210 bp fragment is cleaved into 138 bp and 72 bp fragments. Only the 138 bp fragment hybridizes with the h5a35 probe and is thus visualized in the autoradiogram shown at the bottom. Right: NspI polymorphism in exon 2. Genomic DNAs from the same family members were amplified with the oligonucleotides h5a8 and h5a14 to produce a 288 bp fragment corresponding to exon 2 of the gene. Detection of the polymorphic NspI site was carried out as described in A above, except that two [$^{32}p$]-labeled oligonucleotides (h5a8, h5a14) were hybridized to the filter. The presence of the NspI site results in the cleavage of the amplified DNA into 151 bp and 137 bp fragments.

FIGS. 13A–13D. cDNA and amino acid (SEQ ID NOS: 5 and 6 respectively ) sequence of human 5α-reductase 2. Nucleotides are numbered at right. Amino acids are numbered above the protein sequence. The GenBank accession number for this sequence is M74047.

FIG. 14. Alignment of 5α-reductase proteins. The amino acid sequences in single letter code of the human 5α-reductase 2, 5α-reductase 1 and rat 5α-reductase proteins (SEQ ID NOS: 1, 3, 7, 9–11, 13–15, 17–19, 21–23, 5, 25, and 27, respectively) are aligned. Identities between two or more enzymes are boxed in black. Numbers above the sequences refer to the human 5α-reductase 2 protein.

FIGS. 17A–17D. Structure of human steroid 5α-reductase pseudogene. The DNA sequence of a second genomic DNA hybridizing with the steroid 5α-reductase cDNA is shown. Nucleotides (SEQ ID NOS: 25, 27) are numbered on the right beginning with the most 5' base sequenced and amino acids (SEQ ID NOS: 26 and 28, respectively) are numbered above the protein sequence. The sequence similarity between the functional type 1 gene (FIG. 10) (SEQ ID NOS: 7, 9–11, 13–15, 17–19 and 21–23 respectively) and pseudogene begins at a 5'-boundary demarked by the 3'-end of a LINE sequence (arrow above sequence) and includes the TATA sequence (overline). The 12 bp sequences that are directly repeated at the 5'- and 3'-ends of the pseudogene are indicated by arrows above the sequence. A translation termination codon at amino acid residue 147 is boxed as is the termination codon at the end of the coding region. An oligo-adenylate tract at the 3'-end of the gene is underlined.

DETAILED DESCRIPTION OF THE PREFERRED EMBODIMENTS

1. Introduction

Figure 1A:
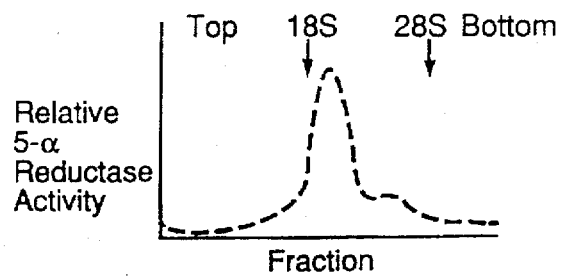
FIGS. 1A–1E. Expression cloning of rat steroid 5α-reductase. Female rat liver RNA was size fractionated on 10–25% sucrose gradients and aliquots of RNA were assayed for steroid 5α-reductase activity in Xenopus oocytes. Peak activity fractions were used to construct an oriented cDNA library in a plasmid RNA expression vector. E. coli transformants from this library were pooled in groups of 150–200 clones and assayed for enzyme expression. A thin layer chromatography assay was employed in which the substrate testosterone (T) could be separated from androstenedione (A) and the 5α-reduced forms of these two steroids (DHT and 5αA, respectively). Sibling selection of a positive pool of clones was carried out as described in Example 1.
Figure 1B:
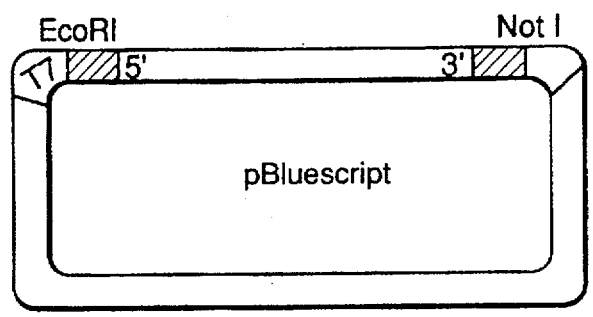
Figure 1C:
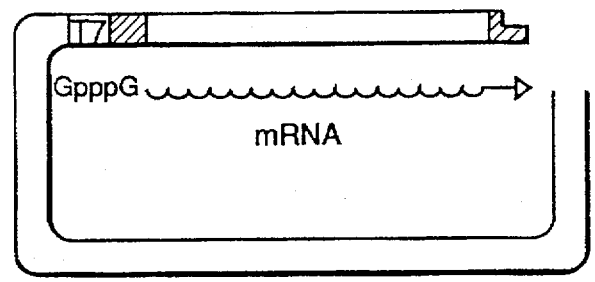
Figure 1D:
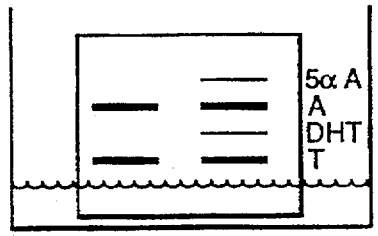
Figure 1E:
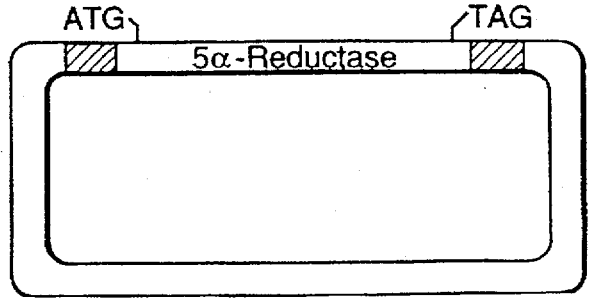

The 5α-reduction of testosterone is catalyzed in rat and man by a membrane-bound, NADPH-dependent enzyme termed steroid 5α-reductase (Wilson, 1975; Moore & Wilson, 1972). The conversion of testosterone into dihydrotestosterone by steroid 5α-reductase is a key reaction in androgen action, and is essential both for the formation of the male phenotype during embryogenesis and for androgen-mediated growth of tissues such as the prostate (Wilson, 1975;1985). Single gene defects that impair this conversion lead to pseudohermaphroditism, originally termed pseudo-vaginal perineoscrotal hypospadias, in which 46, XY individuals have male internal urogenital tracts, but external genitalia which have differentiated into female structures (Griffin & Wilson, 1989).

Until recently, the number of enzymes that could effect this transformation was unknown. After the initial description of this enzyme (Schneider, 1952), it was originally assumed that several steroid 5α-reductase isozymes must exist, each of which preferentially utilized a different steroid substrate (McGuire & Tomkins, 1960). In agreement with this notion, steroid 5α-reductase activities with different kinetic properties and pH optima have been demonstrated in human tissues (Moore & Wilson, 1976; Bruchovsky et al., 1988; Itami et al., 1991). One of these activities appeared to be absent in patients with steroid 5α-reductase deficiency (Moore et al., 1975). However, the fact that the 5α-reduction of all steroid hormones was impaired in these patients (Imperato-McGinley & Gautier, 1986), suggested that one enzyme was responsible for this activity.

Further insight into the existence and function of steroid 5α-reductase isozymes has been hampered by the low levels of enzyme activity expressed in tissues and by the profound insolubility of the protein (Wilson, 1975; Moore & Wilson, 1972). However, the present inventors recently isolated cDNAs encoding both rat and human steroid 5α-reductases (Co-pending U.S. patent application, Ser. No. 07/517,661; Andersson et al., 1989a; Andersson & Russell, 1990). The rat and human steroid 5α-reductase proteins thus identified represent a class of NADPH-dependent, membrane bound steroid metabolizing enzymes. They are small hydrophobic proteins that lack a cleavable signal sequence and have the capacity to traverse the endoplasmic reticulum or nuclear membrane multiple times (Andersson et al., 1989a). The locations of functional domains in these enzymes, such as those that bind the steroid substrate or NADPH cofactor are presently unknown. Computer-assisted comparisons of their sequences to other proteins in multiple data bases, including several steroid dehydrogenases (Agarwal et al., 1989), have so far not revealed any overt homologies (Andersson and Russell, 1990).

In the rat, nucleic acid hybridization experiments provided evidence that the same steroid 5α-reductase mRNA and gene were expressed in both the prostate and the liver (Andersson et al., 1989a). Expression of this gene in the regenerating prostate was shown to be regulated by androgens (Andersson et al., 1989a), and transfection of the cDNA into simian COS cells was shown to result in the synthesis of a steroid 5α-reductase enzyme that was active against a wide variety of substrates and that was inhibited by 4-aza steroid compounds such as 17β-N-t-butyl-carbamoyl-4-aza-5α-androst-1-en-3-one (finasteride, MK-906) (Andersson & Russell, 1990). On balance, this data suggested that steroid 5α-reduction in the rat could be mediated by the action of a single enzyme.

A cDNA encoding human steroid 5α-reductase was isolated from a prostate cDNA library by cross-hybridization using a nucleotide probe based on the sequence of the rat steroid 5α-reductase (Andersson and Russell, 1990). The protein encoded by this cDNA, designated steroid 5α-reductase 1, was shown to be 259 amino acids in length and to share approximately 60% sequence identity with the rat enzyme. Expression of a full-length cDNA in mammalian cells produced asteroid 5α-reductase enzyme that actively reduced a spectrum of substrates and that was inhibited by some, but not all, 4-aza steroids (Andersson and Russell, 1990). Prior to the current invention, there remained many outstanding questions concerning the number of human steroid 5α-reductase enzymes, the chromosomal location of their genes, their protein biochemical and pharmacological properties and the molecular events underlying such diseases as male pattern baldness, pseudohermaphroditism, endometriosis, acne, hirsutism, cancer of the prostate, or even other poorly described endocrine disorders of androgen metabolism.

The present disclosure specifically describes the cloning and sequence of DNA segments encoding steroid 5α-reductase genes and a related pseudogene, and in particular, a novel gene encoding the major steroid 5α-reductase isozyme active in genital tissue. Also disclosed is the discovery that deletions in this latter gene underlie male pseudohermaphroditism. With these disclosures in light of the teachings herein, it is submitted that those of skill in the art will be able, without an undue amount of experimentation, to prepare DNA segments encoding steroid 5α-reductases. They will be further able to employ such DNA segments as probes for the identification of individuals who might carry certain allelic variants of, or defective, steroid 5α-reductase genes, such as might predispose an individual to the disorders discussed above. Additionally disclosed are methods for employing these DNA segments to produce functional and assayable steroid 5α-reductases, which may be employed in a variety of manners. For example, in the development of screening assays to identify and characterise specific inhibitors of the prostate enzyme, or in a detailed analysis of the properties of normal and mutant steroid 5-reductases, or in the rational design of inhibitors following ther determination of the three dimensional structure of the enzyme.

2. Screening Assays

An important aspect of the invention is the use of recombinantly produced steroid 5α-reductase in screening assays for the identification of substances which may inhibit or otherwise modify or alter the enzymatic function of the enzyme. The use of recombinantly produced enzyme is of particular benefit because the naturally occurring enzyme is present in only small quantities and has proven difficult to purify. Moreover, this allows one a ready source of human enzyme, and particularly, the human genital tissue isozyme, which have heretofore been lacking. The inventors discovered that the human enzymes are different from the steroid 5α-reductase obtained from species such as rat in terms of their sensitivity to various candidate substances. The importance of this is quite significant in that it indicates that where one seeks to identify a compound, e.g., that may function to inhibit the enzyme in man, that one should employ human species of steroid 5α-reductase for the screening assay, in particular, one may wish to employ the human genital tissue isozyme, termed steroid 5α-reductase 2. The results disclosed herein further suggest that previous studies using enzymes from species other than humans may not be accurate with respect to man.

The screening assays of the invention, in preferred embodiments, conveniently employ the enzyme directly from the recombinant host in which it is produced. This is achieved most preferrably by simply expressing the selected enzyme within the recombinant host, here a eukaryotic host, followed by preparing a crude homogenate which includes the enzyme. A portion of the crude homogenate is then admixed with an appropriate substrate of the enzyme, e.g., testosterone, progesterone, or androstenedione, along with the candidate substance to be tested. By comparing the action of the enzyme on the selected substrate in the presence or absence of the candidate substance, one can obtain information regarding the ability of the candidate substance to affect the activity of the enzyme.

In that most such screening assays in accordance with the invention will be designed to identify agents useful in inhibiting the conversion of testosterone, preferred assays will employ testosterone as the normal substrate.

There are believed to be a wide variety of embodiments which can be employed to determine the effect of the candidate substance on the enzymes of the invention, and invention is not intended to be limited to any one such method. However, it will generally be desireable to employ a system wherein one can measure the ability of the enzyme to convert the subtrate employed to a particular product. One method employed by the inventors uses a labeled subtrate, which has been labeled in a manner such that the label is quantitatively retained in the resultant product. A convenient approach is the use of a radioactive label, such as $^{14}C$ or $^{3}H$, which may be directly quantitated in both the substrate and the resultant product.

In preferred assays, the admixture containing the enzyme, substrate and candidate substance is allowed to incubate for a selected amount of time, and the resultant incubated mixture subjected to a separation means in order to separate the substrate remaining in the admixture from any product produced. Then, one simply measures the amount of each, e.g., versus a control to which no candidate substance has been added. This measurement can be made at various time points where velocity data is desired. From this, one may determine the ability of the candidate substance to alter or modify the function of the enzyme.

Numerous techniques are known which could be employed for the separation of the substrate from product, and all such methods are intended to fall within the scope of the invention. The inventors prefer to use thin layer chromatographic methods (TLC), as TLC-based methods are quick, accurate, inexpensive and quite sensitive. However, other useful techniques might include, e.g., or other techniques such as HPLC, spectrophotometric, gas chromatographic/mass spectrophotometric or even using NMR analyses. It is contemplated that any such technique may be employed so long as it is capable of differentiating between the enzyme substrate and product, and can be used determine enzymatic function such as by identifying or quantifying the substrate and product.

3. Nucleic Acid Hybridisation Embodiments

As mentioned, in certain aspects, the DNA sequence information provided by the invention allows for the preparation of relatively short DNA (or RNA) sequences having the ability to specifically hybridize to gene sequences of the selected steroid 5α-reductase gene. In these aspects, nucleic acid proms of an appropriate length are prepared based on a consideration of the selected steroid 5α-reductase gene sequence, e.g., a sequence such as that shown in FIGS. 4, 7, 10 or 13, or even such as that shown in FIG. 17 (SEQ ID NOS: 1, 3, 7, 9–11, 13–15, 17–19, 21–23, 5, 25, and 27, respectively). The ability of such nucleic acid probes to specifically hybridize to the steroid 5α-reductase gene sequences lend them particular utility in a variety of embodiments. Most importantly, the probes can be used in a variety of assays for detecting the presence of complementary sequences in a given sample. However, either uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 10 to 30 or so long nucleotide stretch of the steroid 5α-reductase sequence, such as that shown in FIGS. 4, 7, 10 or 13, or even 17 (SEQ ID NOS: 1, 3, 7, 9–11, 13–15, 17–19, 21–23, 5, 25, and 27, respectively). A size of at least 10 nucleotides in length helps to ensure that the fragment will be of sufficient length to form a duplex molecule that is both stable and selective. Molecules having complementary sequences over stretches greater than 10 bases in length ore generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, the nucleotide sequences of the intention may be used for their ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and\or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate steroid 5α-reductase coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such a urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

4. Biological Functional Equivalent Amino acids

As noted above, it is believed that, where desired, modification and changes may be made in the structure of the steroid 5α-reductase and still obtain a molecule having like or otherwise desirable characteristics.

For example, certain amino acids may be substituted for other amino acids in a protein structure without appreciable loss of interactive binding capacity with structures such as antigen-binding regions of antibodies (or, e.g., binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even counterveiling properties (e.g., antagonistic v. agonistic). It is thus contemplated by the inventors that various changes may be made in the sequence of the peptides (or underlying DNA) without appreciable loss of their biological utility or activity.

The importance of the hydropathic index of amino acids in conferring interactive biologic function on a protein has been discussed generally by Kyte et al. (1982), or U.S. Pat. No. 4,554,101 to Hopp, both incorporated herein, wherein it is found that certain amino acids may be substituted for other amino acids having a similar hydropathic index or score and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE I

| AMINO ACID | HYDROPATHIC INDEX |
| --- | --- |
| Isoleucine | 4.5 |
| Valine | 4.2 |

TABLE I-continued

| AMINO ACID | HYDROPATHIC INDEX |
| --- | --- |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

It is proposed that where an amino acid has a hydropathic index of within ±2 that of the best amino acid, and more preferably within ±1, such a change should nevertheless provide a protein having a similar, and perhaps even improved, functional activity. Thus, for example, it is proposed the isoleucine, which has a hydrophatic index of +4.5, can be substituted for valine (+4.2) or leucine (+3.8), and still obtain a protein having similar biologic activity. Alternatively, at the other end of the scale, it is proposed that lysine (−3.9) can be substituted for arginine (−4.5), and so on.

Accordingly, these amino acid substitutions are generally based on the relative similarity of R-group substituents, for example, in terms of size, electrophilic character, charge, and the like. In general, exemplary substitutions which take various of the foregoing characteristics into consideration include the following:

TABLE II

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg |
| Met | met; leu; tyr |
| Ser | thr |
| Thr | ser |
| Trp | tyr |
| Tyr | trp; phe |
| Val | ile; leu |

5. Site-Specific Mutagenesis

Site-specific mutagenesis is a technique useful in the preparation of second generation proteins, or biologically functional equivalent proteins or peptides, derived from the sequences thereof, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman et al., (1983). As will be appreciated, the technique typically employs a phage vector which exist in both a single stranded and double stranded form. Typical vectors useful in site-directed mutagenesis include vectors such as the M13 phage (Messing et al., 1981). These phage are readily commercially available and their use is generally known to those of skill in the art.

In general, site-directed mutagenesis in accordance herewith is performed by first obtaining a single-stranded vector which includes within its sequence a DNA sequence which encodes all or a portion of the steroid 5α-reductase sequence. An oligonucleotide primer bearing the desired mutated sequence is prepared, generally synthetically, for example, by the method of Crea et al., (1978). This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutated sequence arrangement.

6. Host Cell Cultures and Vectors

In general, of course, prokaryotes are preferred for the initial cloning of DNA sequences and constructing the vectors useful in the invention. For example, E. coli K12 strains may be particularly useful. Other microbial strains which may be used include E. coli B, and E. coli X 1776 (ATCC No. 31537). These examples are, of course, intended to be illustrative rather than limiting.

Prokaryotes may also be used for expression. The aforementioned strains, as well as E. coli W3110 (F-, lambda-, prototrophic, aTCC No. 273325), bacilli such as Bacillus subtilus, or other enterobacteriacea such as Salmonella typhimurium or Serratus marcesans, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR 322, a plasmid derived from an E. coli species (Bolivar et al., 1977). pBR 322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the β-lactamase (penicillinase) and lactose promoter systems (65–67) and a tryptophan (TRP) promoter system (68–69). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in Saccharomyces, the plasmid YRp7, for example, is commonly used (Stinchcomb et al., 1979, Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequences desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propogation of vertebrate cells in culture (tissue culture) has become a routine procedure in recent years (Kruse and Peterson, 1973). Examples of such useful host bell lines are AtT-20 VERO and HeLa cells, Chinese hamster ovary (CHO) cell lines, and W138, BHK, COSM6, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Cytomegalovirus and most frequently simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin or replication. Further, it is also possible, and often desirable, to utilize promoter or control sequences normally associated with the desired gene sequence, provided such control sequences are compatible with the host cell systems.

An origin of replication may be provided with by construction of the vector to include an exogenous origin, such as may be derived from SV40 or other viral (e.g., Polyoma, Adeno, VSV, BPV, CMV source, or may be provided by the host cell chromosomal replication mechanism. If the vector is integrated into the host cell chromosome, the latter is often sufficient.

7. pCMV Eukaryotic Expression Vectors

The pCMV plasmids are a series of mammalian expression vectors. The vectors are designed for use in essentially all cultured cells and work extremely well in SV40 - transformed simian COS cell lines. The pCMV1, 2, 3, and 5 vectors differ from each other in certain unique restriction sites shown in the polylinker region above each plasmid. The pCMV4 vector differs from these 4 plasmids in containing a translation enhancer in the sequence prior to the polylinker.

The universal components of the pCMV plasmids are as follows. The vector backbone is pTZ18R (Pharmacia), and contains a bacteriophage f1 origin or replication for production of single stranded DNA and an ampicillin-resistance gene. The CMV region consists of nucleotides −760 to +3 of the powerful promote-regulatory region of the human cytomegalovirus (Towne stain) major immediate early gene (Thomsen et al., 1984); Boshart et al., 1985). The polylinker region may be synthesized on an Applied Biosystem's machine. The human growth hormone fragment (hGH) contains transcription termination and polyadenylation signals representing sequences 1533 to 2157 of this gene (Seeburg, 1982). There is an Alu middle repetitive DNA sequence in this fragment. Finally, the SV40 origin of replication and early region promoter-enhancer (white box) was derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguished from each other which restriction enzyme sites are unique in the polylinker and by the presence or absence of the translation enhancer. The starting pCMV1 plasmid has been progressively modified to render unique an increasing number of sites in the polylinker. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter. The sequence acts as a transnational enhancer by decreasing the requirements for initiation factors in protein synthesis (Jobling et al., 1987); Browning et al., 1988). To create pCMV5, a segment of DNA (HpaI to EcoRI) was deleted from the SV40 origin region of pCMV1 to render unique all sites in the starting polylinker.

The pCMV vectors have been employed in simian COS cells, mouse L cells, CHO cells, and HeLa cells. In several side by side comparisons they have yielded 5- to 10-fold higher expression levels in COS cells than SV40 -based vectors. The pCMV vectors have been used to express the LDL receptor, nuclear factor 1, $G_s$ alpha protein, protein phosphatase, synaptophysin, synapsin, insulin receptor, flu hemmagglutin in, antrogen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites that may cause spurious translation initiation. Avoid this codon if possible in your expression plasmids. A paper describing the construction and use of the parenteral pCMV1 and pCMV4 vectors has been published (Andersson et al., 1989b).

EXAMPLES

Examples have been included in order to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example 1

Expression Cloning of Rat Steroid 5α-Reductase

Prior to the present invention, there was no known sequence information available for any steroid 5α-reductase enzyme on which the construction of oligonucleotide probes for cloning could be based. Therefore, a novel approach was developed, based in part on a strategy employing Xenopus oocyte expression cloning employed in the isolation of lymphokines (Noma, et al., 1986), neurotransmitter receptors (Masu et al., 1987; Lubbert et al., 1987; Julius et al., 1988) and membrane transporters (Hediger et al., 1987).

1A: Protocols Employed

Steroid 5α-Reductase Enzyme Assay. Stage 5 and 6 oocytes were surgically removed from female Xenopus laevis (NASCO, Fort Atkinson, Wis.) and collagenase-treated as described by Julius et al., (1988). Oocytes were injected with 50–100 nl of RNA (1 μg/μl) as described by Peacock et al. (Peacock et al., 1988). After injection the oocytes were incubated at 19° C. for 24 hours in modified Barth's saline solution (Peacock et al., 1988) containing 1 mg/ml bovine serum albumin (BSA) to allow expression of the injected RNA. Five to ten viable oocytes were then transferred to 1 ml of modified Barth's saline solution containing 5 μM $^{14}$C-labeled steroid (50 mCi/mmol, Du Pont-New England Nuclear), and incubated at 37° C. for 2–24 h. This temperature-jump protocol is based on the observation that expression of mRNA in Xenopus is maximal a 19° C., whereas rat steroid 5α-reductase expressed in Xenopus has a temperature optima of 37° C. After the 37° C. incubation, the oocytes were homogenized in the incubation medium and steroid was extracted with 10 ml of dichloromethane. The solvent was evaporated under air and the residue was dissolved in 0.1 ml of chloroform/methanol (2:1, v/v) and subjected to thin-layer chromatography using Siica Gel 60 thin-layer chromatography plates (E. merck, 5748-7, Darmstadt, West Germany). The chromatoplates were autoradiographed for 18 hours at −70° C. and the radioactive zones were cut out and subjected to liquid scintillation counting in Complete Counting Cocktail (Research Products International). The identities of the products were determined by comparison to the $R_f$ values of known standards.

cDNA Cloning. Total RNA from female rat liver was extracted by a guanidinium isothiocyanate/CsCl procedure (Maniatis et al., 1982). Poly(A$^+$) -enriched RNA was isolated and size-fractionated by density gradient centrifugation on 10–25% (w/v) sucrose gradients containing methylmercury hydroxide (Schweinfest et al., 1982). After centrifugation at 4° C. for 15 hours at 76,800× g, aliquots of RNA from each gradient fraction were assayed for steroid 5α-reductase mRNA by injection into Xenopus oocytes. Positive fraction from the sucrose gradients were combined and the RNA was concentrated by ethanol precipitation. First strand cDNA was synthesized using mRNA pretreated with 2.5 mM methylmercury hydroxide and AGCGGCCGC (T)$_{20}$ (SEQ ID NO: 29) as a primer. Second strand synthesis, EcoRI methylation, flushing of ends with bacteriophage T4 DNA polymerase, and addition of phosphorylated EcoRI linker were performed according to standard procedures (Maniatis et al., 1982). The resulting cDNA was digested with NotI and EcoRI and size-fractionated on a 1% (w/v) agarose gel. Complementary DNAs greater than 1.3 kb were inserted into the NotI and EcoRI sites of Bluescript (Stratagene, LA Jolla, Calif.). Recombinant plasmids were propagated in E. coli DH5αF'IQ (GIBCO). A rat ventral prostate cDNA library was constructed as described above except that random hexanucleotides were used as primers and total poly(A$^+$) RNA was used as template. Size-fractionated cDNAs deriver from prostate mRNA were inserted into the EcoRI site of λZapII (Stratagene). Recombinant bacteriophage were propagated in E. coli XL1-Blue. Bluescript plasmids were subsequently rescued from λZap recombinants by superinfection with helper F1 bacteriophage.

In the initial screening of the female rat liver cDNA library, plasmids minipreps were prepared from 20 pools containing 150–200 cDNA clones/pool. Plasmid DNA was linearized with NotI and RNA was transcribed in vitro using bacteriophage T7 RNA polymerase (Pharmacia LKB Biotechnology Inc.) as described by Julius et al., (1988). Xenopus oocyte injection was carried out as described above. Plasmid DNA from one positive pool was retransformed and 960 colonies were randomly picked into individual 0.3-ml cultures maintained in 96-well microtiter plates. Plasmid DNAs were subsequently prepared from pools of 100 μl aliquots from each well and assayed by microinjection. Sibling selection from the microtiter plate was carried out by matrix analysis.

Nucleic Acid Sequencing and Primer Extension. Overlapping fragments from both DNA strands were subcloned into bacteriophage M13 vectors and sequenced by automated methods (Smith et al., 1986) using an Applied Biosystems model 370A DNA sequencer. For primer extension analysis, an antisense oligonucleotide complimentary to nucleotides 70–109 of FIG. 4A was annealed at 68° C. to rat liver poly(A$^+$) RNA and extended with reverse transcriptase as described by Sudhof et al. (1987). Direct RNA sequencing of the steroid 5α-reductase mRNA was carried out as described by Geliebter et al. (1986).

In Vitro Translation of RNA. Approximately 100 ng of RNA was translated in vitro using [$^{35}$S]methionine (1100 Ci/mmol) and a rabbit reticulocyte lysate (Promega, Madison, Wis.) in the presence or absence of dog pancreas microsomes (Walter et al., 1981). After incubation for 1 hour at 30° C., the reactions were terminated by adding cycloheximide to a final concentration of 0.2 mM or RNase A to 2 mg/ml. Experiments with products translated in vitro in the presence of 50 µg/ml trypsin (GIBCO) were performed with or without 2% (w/v) Triton X-100 (Boehringer Mannheim) for 30 min at 22° C. The protease reactions were terminated by adding soybean trypsin inhibitor (Cappel, Malvern, Pa.) to a final concentration of 1 mg/ml.

Physiological Experiments. Studies were designed to allow comparison of mRNA levels in liver and prostate of normal rats, of 7-day castrated animals, of 10-day castrated animals, and of normal or 10-day castrated animals given testosterone on days 7–9 of the experiment. Sexually mature Sprague-Dawley male rats were castrated by standard surgical procedures on day 0. On day 7, experimental groups were subcutaneously injected for 3 consecutive days with 2 mg of testosterone acetate or testosterone propionate dissolved in 0.2 ml of sesame oil (Moore et al., 1973). Control animals were injected with sesame oil alone. On day 10 of the experiment, RNA was prepared from the livers and prostates of up to 15 animals in each experimental group, and analyzed by blotting as described in the legend to FIG. 6.

1B:Results.

Expression Cloning of the Rat Liver Steroid 5α-Reductase cDNA.

The strategy used to obtain a full length cDNA for the rat liver steroid 5α-reductase is outlined in FIG. 1. As a source of mRNA, female rat liver was used, which for physiologically unknown reasons expresses high levels of steroid 5α-reductase enzyme activity (Moore et al., 1972). Microinjection into Xenopus oocytes indicated that this mRNA could direct the synthesis of an enzyme that catalyzed the conversion of steroids into their 5α-reduced forms (see below). Sucrose gradient fractionation of rat liver mRNA indicated that this activity was encoded by an mRNA of about 2.5 kb (FIG. 1). Similar results have recently been reported by Farkash et al. (1988). The mRNA in this fraction was converted into cDNA, size-fractionated, and cloned into an RNA expression vector. To avoid problems with antisense inhibition, the cDNA library was constructed in an oriented manner (FIG. 1). Twenty pools, each containing 150-200 cDNA clones, were then used to synthesize mRNA that was in turn injected into oocytes to allow determination of steroid 5α-reductase activity by thin-layer chromatography analysis. From one active pool, a near full length cDNA encoding this enzyme was subsequently isolated by dilution cloning (FIG. 1).

Figure 2:
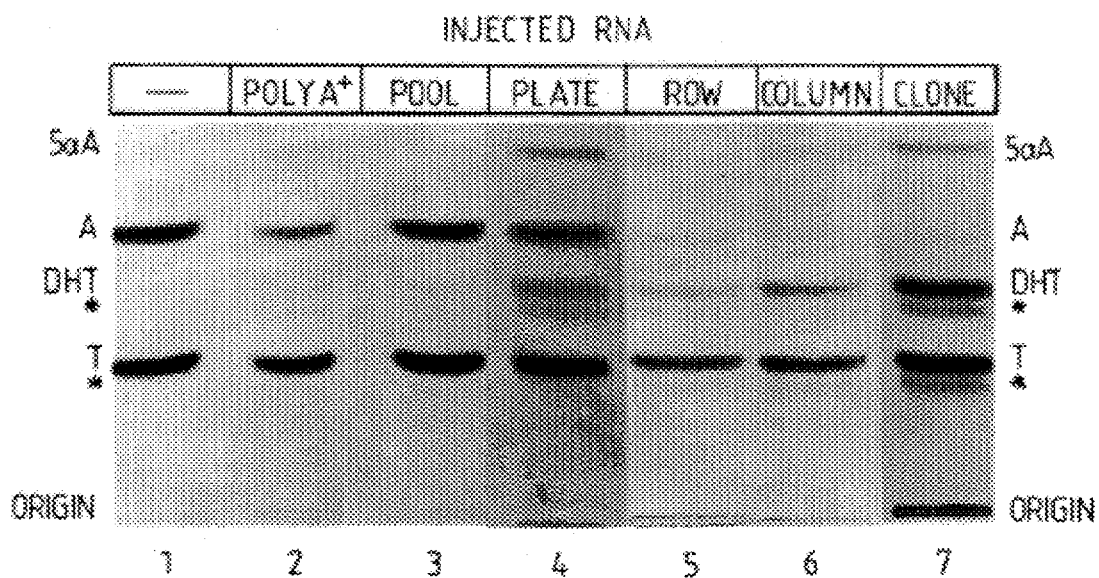
FIG. 2. Dilution cloning of a rat liver steroid α-reductase cDNA. Xenopus oocytes were injected with RNA from the indicated source and assayed for steroid 5α-reductase activity by thin-layer chromatography using [$^{14}$C]testosterone as a substrate as described in Example I. Lane 1, H$_2$O-injected; lane 2, RNA from female rat liver; lane 3, RNA synthesized in vitro from a pool of 150–200 cDNA clones; lane 4, RNA synthesized from cDNAs inoculated in a 96-well microtiter plate; lane 5, RNA synthesized from a pool of 12 clones corresponding to a row from the microtiter late; lane 6, RNA synthesized from eight clones corresponding to a column from this plate; and lane 7, RNA derived from a cDNA clone corresponding to the intersection of the row and column. Chromatograms from the various experiments were exposed to Kodak XAR-5 film for 16 hours. In the chromatographic system employed, hydrophobic steroids migrate further than hydrophilic steroids. The positions of authentic steroid standards are shown on the left of the autoradiograms. T, testosterone, A, androstanedione, DHT, 5α-dihydrotestosterone, 5αA, 5α-androstanedione. An endogenous Xenopus enzyme in the oocytes converts testosterone into androstenedione. Steroids marked with an asterisk are uncharacterized metabolites derived from the 5α-reduced compounds by endogenous Xenopus enzymes (see FIG. 3).

The results of thin-layer chromatography assays from the dilution cloning are illustrated in FIG. 2. Steroid 5α-reductase activity in injected oocytes was assayed for using a temperature-jump protocol, as detailed above. Microinjection of water into Xenopus oocytes revealed an endogenous activity capable of converting the testosterone substrate into androstenedione, and little or no ability to convert these steroids into their 5α-reduced forms (Figure, lane 1). In contrast, when female rat liver mRNA was injected, the oocytes expressed an activity that generated both dihydrotestosterone and 5α-androstanedione, as well as at least two other steroid metabolites (FIG. 2, lane 2). These latter unidentified steroids were derived from the 5α-reduced metabolites generated by the injected mRNA (see below).

When RNA was synthesized from one of the initial 20 cDNA plasmid pools that contained 150-200 independent clones, the spectrum of steroid metabolites observed was identical to that seen upon injection of liver mRNA (FIG. 2, lane 3), thus indicating that this pool must contain at least one steroid 5α-reductase cDNA. The cDNAs from this pool were retransformed into E. coli and individual colonies were picked into microtiter plates. Lane 4 shows the results obtained after microinjection of RNA prepared from plasmids isolated from a 96-well plate that contained a steroid 5αa-reductase cDNA from this transformation. Subsequent analysis of mRNA from pools of plasmids corresponding to the rows and columns of this microtiter plate identified a row (lane 5) and column (lane 6) containing a steroid 5α-reductase plasmid. The intersection of this row and column on the microtiter plate localized the positive cDNA (lane 7).

Substrate Specificity of the Cloned Rat Liver steroid 5α-Reductase.

Figure 3:
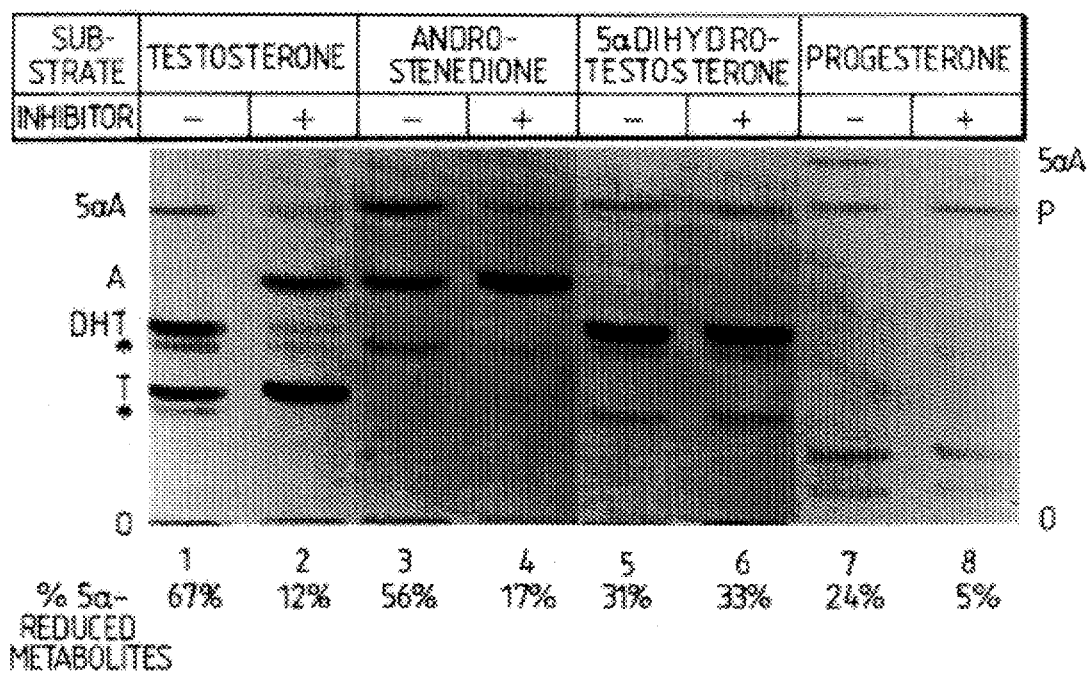
FIG. 3. Substrate Specificity of the cloned rat steroid 5α-reductase. Xenopus oocytes obtained from a single animal were injected with in vitro synthesized RNA derived from the steroid 5α-reductase cDNA clone and then assayed for enzyme activity using the indicated $^{14}$C-labeled steroid substrates (5 μM) in the absence (−) or presence (+) of the competitive inhibitor 4-MA (5 μM). The various steroids and metabolites are identified on the left and right of the autoradiograms: P, progesterone ; 5αP, 5α-dihydroprogesterone; others are as indicated in the legend to FIG. 2. The amount of 5α-reduced metabolites for each substrate is indicated at the bottom of the figure and was determined by liquid scintillation counting after cutting out appropriate zones from the chromatograms. In lane 5 and 6, all radioactive derivatives of dihydrotestosterone were counted. The pattern of metabolites obtained when dihydrotestosterone was employed as a substrate was identical in both $H_2O$-injected and steroid 5α-reductase RNA-injected oocytes.
Figure 4:
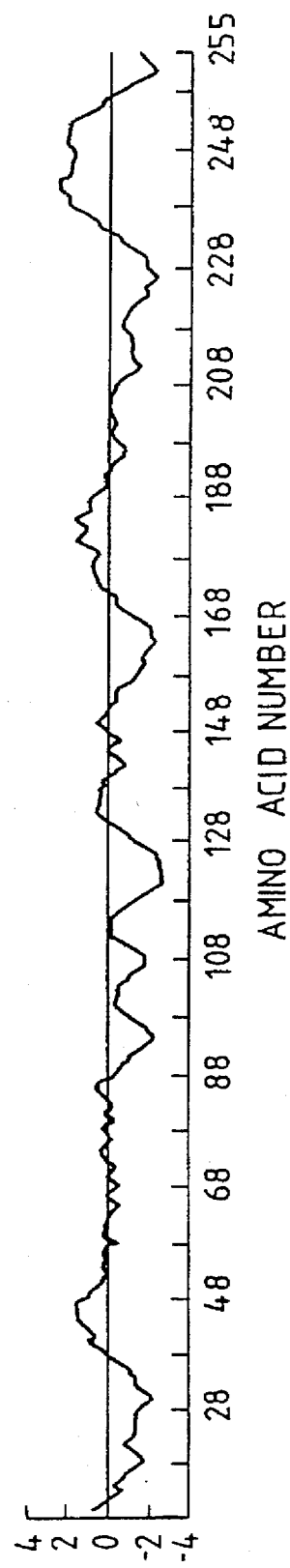
FIGS. 4A–4E. Nucleotide sequence of the cDNA corresponding to the rat steroid 5α-reductase mRNA. (SEQ ID NO: 1) predicted amino acid (SEQ ID NO: 2) sequence, and hydropathy profile of the protein. A, nucleotides are numbered on the right-hand side. The amino acids are numbered above the sequence with position 1 arbitrarily assigned to the first methionine codon in the nucleotide sequence. Two polyadenylation signals are overlined. B, the sequence of the steroid 5α-reductase protein was subjected to a hydropathy analysis using the algorithm of Kyte and Doolittle (1982). Sequences above the central dividing line are hydrophilic, and those below the line are hydrophobic.

RNA synthesized from the steroid 5α-reductase cDNA plasmid identified in FIG. 2 was microinjected into oocytes and allowed to express for a 24-hour period. The oocytes were then incubated with different radiolabeled steroids for an additional 24 hours and the products formed were analyzed by thin-layer chromatography (TLC). FIG. 3, lane 1, shows the typical pattern of 5α-reduced metabolites formed from testosterone. Lane 2 indicated that co-incubation of the injected eggs with equimolar amounts of testosterone and the competitive steroid 5α-reductase inhibitor 4-MA resulted in a substantial decrease in the formation of these products. As a control for nonspecific inhibition, the conversion of testosterone into androstenedione catalyzed by an endogenous Xenopus enzyme (presumably a 17β-hydroxysteroid dehydrogenase, Miller, 1988), was not inhibited by 4-MA in this experiment (lane 2). Both androstenedione and progesterone were substrates for the cloned enzyme (lanes 3 and 7). As with testosterone, 4-MA efficiently blocked the reduction of these steroids (lanes 4 and 8, respectively). When radiolabeled dihydrotestosterone was used as a substrate (lane 5), the inhibitor had no effect on the conversion of this compound into other 5α-reduced metabolites by endogenous Xenopus enzymes (lane 6).

Sequences of Rat Liver Steroid 5α-Reductase

The nucleotide sequence of the rat liver steroid 5α-reductase cDNA was determined and the amino acid sequence of the protein deduced (FIG. 4A) (SEQ ID NO: 2). The cDNA insert in the expressing clone was 2,465 base pairs in length and included a long 3'-untranslated region of 1,691 base pairs and an extended translation reading frame of 765 base pairs. A potential polyadenylation signal is present at position 2,446, upstream of a tract of A residues, suggesting that the 3' end of this cDNA is authentic. In the predicted amino acid sequence, there are three methionine residues in the first 19 amino acids. The context of the first ATG is identical in six out of nine nucleotides with the ideal Kozak consensus sequence (Kozak, 1986), suggesting that this codon may specify the amino-terminal methionine of steroid 5α-reductase. With this assumption, the open reading frame would encode a hydrophobic protein of 255 amino acids with a predicted $M_r$ of 29,343. Over 50% of the amino acids in the protein sequence have hydrophobic side chains. Consistent with this amino acid (SEQ ID NO: 2) composition, a hydropathy plot (FIG. 4B) suggests a protein with many hydrophobic regions. See FIG. 14 for an alignment of the rat and human steroid 5α-reductase sequences.

Characterization of Rat Steroid 5α-Reductase Protein and mRNA

Figure 5:
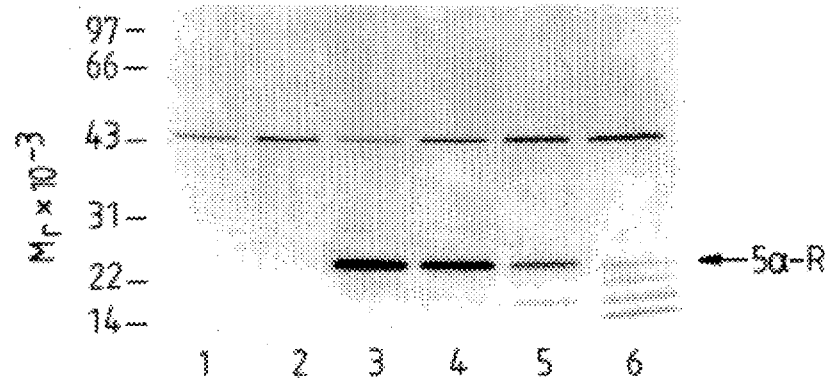
FIG. 5. In vitro translation analysis of rat steroid 5α-reductase RNA. In vitro synthesized steroid 5α-reductase RNA was translated in a reticulocyte lysate as described in Example 1. Additions to individual tubes are indicated above the autoradiogram. Approximately 8% of each translation reaction was analyzed by electrophoresis on 7–15% gradient polyacrylamide-sodium dodecyl sulfate (SDS/PAGE) gels. Size standards are indicated on the left. The band at $M_r$ 45,000 represents an endogenous methionine binding protein in the reticulocyte lysate. The band corresponding to steroid 5α-reductase is indicated on the right of the autoradiogram.

Several reports in the literature have identified a rat liver protein of $M_r$ 50,000 that either has steroid 5α-reductase activity or can be cross-linked to a photoactivatable derivative of 4-MA (Liang et al., 1985; Cheng, 1988). To ensure that the sequence shown in FIG. 4A (SEQ ID NO: 1) represented the complete coding region of steroid 5α-reductase, three kinds of studies were conducted. Firstly, in vitro translation in a rabbit reticulocyte lysate of RNA generated from the steroid 5α-reductase cDNA yielded a protein product with an apparent $M_r$ of 26,000 (FIG. 5, lane 3). When the translation reactions were carried out in the presence of dog pancreas microsomes, a protein product of identical size was observed (lane 4), suggesting the absence of a cleavable signal sequence in this protein. Results from protease protection experiments demonstarted that rat steroid 5α-reductase translated in vitro was incorporated into microsomes. If the vesicular structure of the microsomes was maintained, the translated product was largely resistant to digestion by trypsin (lane 5). However, if the microsomes were disrupted with the detergent Triton X-100 prior to protease treatment, then the steroid 5α-reductase protein was susceptible to digestion (lane 6).

The approximate location of the carboxyl terminus of the rat protein was next determined by analyzing the expression of RNA derived from a series of 3'-truncated derivatives of the cDNA. The steroid 5α-reductase cDNA plasmid was linearized by cleavage with four restriction enzymes that left intact or removed progressively large portions of the predicted 3'-untranslated region and/or carboxyl terminus of the protein. RNA was transcribed in vitro from these templates, microinjected into oocytes, and the oocytes were assayed for steroid 5α-reductase activity using testosterone as a substrate.

Figure 6A:
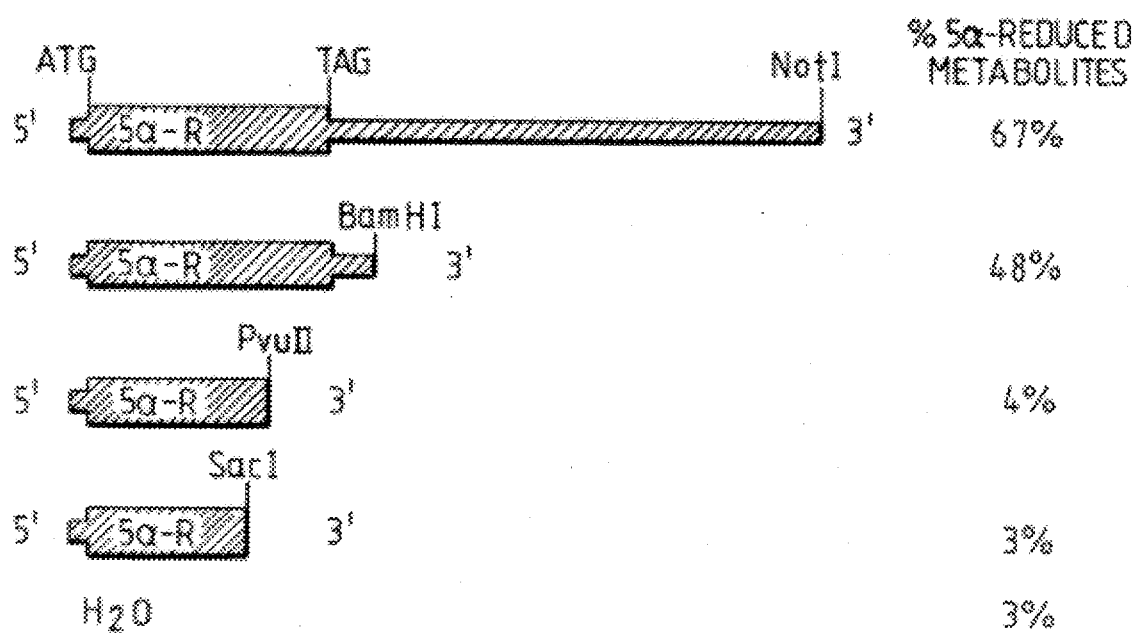
FIGS. 6A–6B. Characterization of the 5' and 3' ends of the rat steroid 5α-reductase cDNA and mRNA. A, expression of 3'-truncated RNAs in Xenopus oocytes. The steroid 5α-reductase cDNA plasmid was linearized with the indicated restriction enzyme and the resulting template was used to synthesize RNA in vitro. Oocytes were injected with the RNA and assayed for activity using testosterone as a substrate. The amount of 5α-reduced steroid metabolites was determined as described in the legend to FIG. 3. The values shown are the average of two or three separate experiments for each RNA. B, primer extension analysis of the 5' end of liver steroid 5α-reductase mRNA, long of poly($A^+$) mRNA from the indicted source was subjected to primer extension analysis as described in Example 1. Size standards (STDS) are indicated on the left of the autoradiogram. Exposure times at –70°C. with an intensifying screen were 13 hours for lanes 1, 3, and 4, and 1 hour for lane 2. nt, nucleotides.

The expression of intact rat steroid 5α-reductase RNA resulted in the reduction of 67% of the testosterone substrate (FIG. 6A). Removal of 1474 nucleotides from the 3'-untranslated region of the mRNA did not substantially affect expression of enzyme activity (BamHI-cleaved template, FIG. 6A). However, removal of 1830 nucleotides from the 3' end, which removes 47 amino acid residues from the predicted carboxyl terminus of the protein, eliminated steroid 5α-reductase activity (PvuII-cleaved template, FIG. 6A). Similar results were obtained with a truncated RNA that removed 57 residues from the carboxyl terminus of the protein (SacI-cleaved template, FIG. 6A). All of these mRNAs yielded a protein of the appropriate size after in vitro translation in a reticulocyte lysate.

Figure 6B:
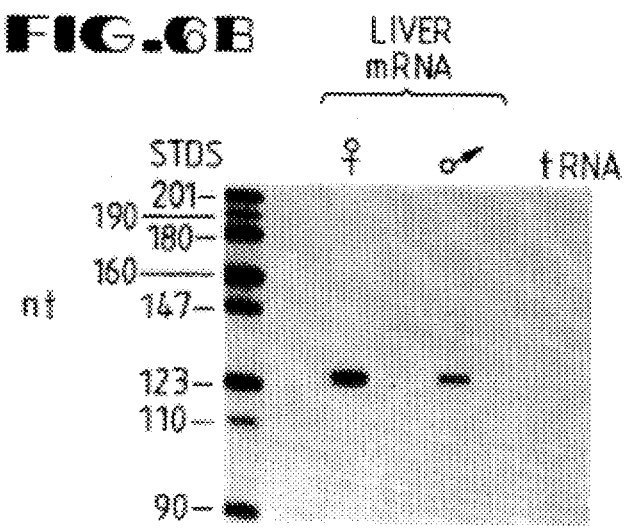

The amino-terminal region of steroid 5α-reductase was examined by carrying out primer extension experiments on liver mRNA. An oligonucleotide primer 40 bases in length and complementary to nucleotides 70–109 of FIG. 4A (SEQ ID NO: 1) was radiolabeled, annealed to mRNA from female and male rat liver, and extended with reverse transcriptase. As shown in FIG. 6B, a single product of 125 nucleotides was detected when RNA from female or male liver was used as a template. These results are consistent with a single 5' end for the steroid 5α-reductase mRNA in this tissue and suggests that the cDNA sequence shown in FIG. 4A (SEQ ID NO: 1) represents a near full length clone. Furthermore, results from direct sequencing in female rat liver using the above primer indicated that the mRNA extends only 17 nucleotides upstream of the 5' end of the cDNA sequence shown in FIG. 4A (SEQ ID NO: 1). There were no inframe translation stop codons in this 5' sequence.

The Liver and Ventral Prostate Forms of Rat Steroid 5α-Reductase Are Identical

To determine if the steroid 5α-reductase isolated from liver was also expressed in prostate, a randomly primed cDNA library derived from ventral prostate mRNA was screened with the insert derived from the liver cDNA clone. A single prostate cDNA was isolated after screening approximately 150,000 independent clones. DNA sequence analysis of the 5' and 3' ends of this clone indicated that it began at nucleotide 1 and terminated at nucleotide 1955 of the liver cDNA sequence shown in FIG. 4A (SEQ ID NO: 1). The sequences were identical between the two clones in these regions. The complete coding region of the prostate-derived cDNA was further subjected to DNA sequence analysis and comparison to that of the liver cDNA again revealed no differences. These results suggested that the isolated gene was expressed in both the liver and prostate of the rat.

Example 2

Cloning and Expression of SRD5A1 cDNA, encoding Human

Steroid 5α-Reductase 1

2A: Protocols Employed

Materials. Radiolabeled steroids were obtained from Du Pont-New England Nuclear and steroid standards were from Sigma and Steraloids, Inc. The 4-azasteroids, 4-MA (17α-N,N-diethylcarbamoyl-4-methyl-4-aza-5α-androtane-3-one) and MK-906 (17β-N-t-butylcarbamoyl-4-aza-5α-androst-1-en-3-one) were gifts of Merck Sharp and Dohme Research Laboratories. Inhibitors were subjected to chemical ionization-mass spectrometry to confirm their identity prior to use.

cDNA Cloning. Two cDNA libraries were constructed from human prostate mRNA. Firstly, cDNA provided by Dr. M. J. McPhaul of The University of Texas Southwestern Medical Center (Tilley et al., 1989) was ligated into the bacteriophage λgt10 vector as described in Example 1. Secondly, prostate tissue from a subject undergoing surgery for prostatic hyperplasia was obtained and used for the isolation of polyadenylated RNA (Sambrook et al., 1989). A size-fractionated cDNA library was subsequently prepared (see Example 1) in λgt10. Clones from these libraries were screened by using hybridization conditions of reduced stringency. DNA sequence analysis was carried out using automated methods on an Applied Biosystems (Foster City, Calif.) model 370A DNA Sequencer. RNA blotting was performed as described by Sambrook et al. (1989).

Expression Vector Construction. A rat steroid 5α-reductase cDNA corresponding to nucleotides 1-1962 (see Example 1) was ligated into the pCMV4 expression vector (Andersson et al., 1989b). A human cDNA corresponding to nucleotides 1 to 842 of FIG. 7 was initially ligated into pCMV4. To modify this poorly expressed human cDNA (see below), two oligonucleotides derived from the 5'-end of the cDNA (5'ATAGATCTACCATGGCAACGGCGA 3') (SEQ ID NO: 30), or from the 3'-untranslated region (5'AAAGTCCATAGAGAAGCGCCATTGG 3') (SEQ ID NO: 31) were employed in a polymerase chain reaction (Saiki et al., 1985) to alter the human cDNA as described below. After amplification, the product was ligated into pCMV4.

Expression of Steroid 5α-Reductase 1 cDNAs in COS Cells. Simian COS-M6 cells were transfected as described by Andersson et al. (1989b). The assay of steroid 5α-reductase activity in intact cells was carried out as described in Example 1 except that [$^{14}$C]-labeled steroid dissolved in ethanol were added to the transfected cell medium and subsequent organic extractions were carried out with dichloromethane. TLC and liquid scintillation counting were performed as described in Example 1. To determine $IC_{50}$ values for the 4-MA and MK-906 inhibitors, a mixture of [$^{14}$C]testosterone and inhibitor in ethanol was added to transfected cell medium, incubated at 37° C. for 2 hr, and treated as above.

To assay steroid 5α-reductase activity in vitro, cells were harvested 48 hours after transfection, washed once with phosphate buffered saline and either frozen in liquid $N_2$ or homogenized directly with a Polytron in 10 mM potassium phosphate (pH 7.4), 150 mM KCl and 1 mM EDTA, at a protein concentration of 2 mg/ml. A typical assay contained 10 to 50 µg of cell homogenate protein in 0.5 ml of 0.1M potassium phosphate buffer (pH 6.6, rat enzyme; pH 7.0, human enzyme). Steroids were added in 5 µl ethanol, and the reaction was initiated by the addition of NADPH to a final concentration of 2-5 mM. Incubations were carried out for 10 min at 37° C. and terminated by the addition of 5 ml dichloromethane. Organic excerations and thin-layer chromatography analysis were as described above. The formation of 5α-reduced steroid products was linear with respect to protein over a 10 to 50 µg range and with respect to incubation time over a 1 to 30 minute period.

2B:Results.

Identification and Analysis of Human Steroid 5α-reductase 1 cDNA.

To isolate clones encoding a human steroid 5α-reductase, cDNA libraries constructed from prostate mRNA were screened at reduced stringency with a radiolabeled fragment corresponding to the coding region of the rat cDNA. A total of five cDNA clones were isolated after screening $3\times10^6$ recombinants from two different cDNA libraries. Each of these cDNAs was subjected to restriction enzyme mapping and DNA sequencing and represented one species of mRNA.

The sequence of the longest cDNA insert, designated type 1, and the corresponding predicted amino acid sequence are shown in FIG. 7 (SEQ ID NO: 3). The DNA sequence predicts an mRNA of at least 2.1 kilobases having a 3'-untranslated region of approximately 1.3 kilobases. Within the 3'-untranslated sequence, a polyadenylation signal (AATAAA) is located 15 nucleotides 5' to a poly-adenine tract, suggesting that the 3' end of this cDNA is authentic. A 5'-untranslated region of 30 nucleotides preceded a translation reading frame of 780 nucleotides encoding this steroid 5α-reductase protein.

Structure of Human Steroid 5α-Reductase 1 and Comparison to the Rat Enzyme.

The amino acid sequence of human steroid 5α-reductase 1, encoded by the SRD5A1 gene, was deduced from the cDNA insert by comparison to that of the functional rat enzyme. Human 5α-reductase 1 is 259 residues long with a predicted molecular weight of 29,462. Over 40% of the amino acids are hydrophobic, and only 16% have positively- or negatively-charged side chains (FIG. 7). These observations are consistent with an intracellular membrane location for the enzyme.

Human steroid 5α-reductase 1 is four amino acids longer at the amino terminus than the rat enzyme, and the overall identity between these two proteins is 60% (FIG. 14). With the exception of the above four residue extension, maximum identity by alignment did not require the introduction of any gaps into the two sequences. The conservation is least in the amino terminal 130 residues, in which only 50% of the amino acids are identical, and most in the carboxyl-terminal half, which exhibits a conservation level of 75%. There is a single methionine residue in the first 89 amino acids of human steroid 5α-reductase 1, whereas there are three methionines in the first 19 residues of the rat protein.

The hydropathy plots of human steroid 5α-reductase 1 and the rat 5α-reductase, as calculated by the algorithm of Kyte & Doolittle (1982), are almost identical. Thus, even though only 60% of their amino acids are shared, the two proteins may have retained similar secondary structures. Interestingly, at the nucleic acid level the two cDNAs are 70% identical in their coding regions, a value that is commonly derived from comparison of other rat and human cDNA homologues (Gonzalez, 1989).

Expression of Rat and human Steroid 5α-Reductase 1 in COS Cells.

To determine if the observed sequence differences between the human and rat steroid 5α-reductase proteins affected their biochemical properties, the two cDNAs were expressed in simian COS cells. For the rat cDNA, a fragment corresponding to nucleotides 1 to 1975 was ligated into the pCMV4 expression vector. For the human SRD5A1 cDNA, a fragment corresponding to nucleotides 1 to 842 of FIG. 7 (SEQ ID NO: 3) was initially ligated into pCMV4. Subsequent transfection studies revealed that expression of this human cDNA yielded a ten-fold lower amount of steroid 5α-reductase enzyme activity than that obtained from the rat cDNA. Inspection of the sequence at the 5'-end of the human cDNA revealed an upstream ATG at position 5 (FIG. 7) (SEQ ID NO: 3) that could conceivably result in spurious translation initiation, leading to the observed reduction in expression. To test this hypothesis, the polymerase chain reaction was used to: 1) introduce an unique BglII restriction enzyme site in the 5'-untranslated region of the cDNA, 2) remove the upstream ATG sequence, and 3) recreate an optimal context for the ATG of steroid 5α-reductase. Transfection of this modified human cDNA into COS cells led to the expression of levels of steroid 5α-reductase enzyme activity that equalled those obtained with the rat cDNA construct.

COS cells were transiently transfected with expression vectors harboring the rat or human steroid 5α-reductase 1 cDNAs, or with the pCMV4 vector alone. Forty-eight hours after transfection, [$^{14}$C]-testosterone was added to the cell media at a final concentration of 2.5 µM, and conversion of this substrate into 5α-reduced steroid products was monitored at the indicated times by TLC. Cells transfected with 5α-reductase cDNAs converted half of the starting substrate into product in 1 hour. The background conversion in the vector-alone transfected cells was low, with only 0.5% conversion occurring after 1 h.

This high level of expression of the cDNAs made possible the assay of steroid 5α-reductase activity in vitro in homogenates derived from the transfected cells. Homogenates were prepared as described above and various biochemical parameters were first optimized to obtain maximum steroid 5α-reductase activity. In this system, both rat and human steroid 5α-reductase 1 enzymes demonstrated a broad pH optima centering around 7.0. The inclusion of NADPH in the COS cell homogenization buffer did not have an effect on the stability of either enzyme. The specific activities of the expressed enzymes were in the nmol/min/mg protein range and were thus equal to that reported for liver homogenates of female rats (Yates et al., 1958).

The apparent $K_m$ and $V_{max}$ values in this system were determined in vitro with five different steroid substrates (Table III). The kinetic constants were determined from a Lineweaver-Burk plot of steroid 5α-reductase activity in the presence of 0.6 to 20 µM substrate and the apparent $K_m$ and $V_{max}$ values were determined by linear regression analysis. Both enzymes demonstrated very low activities towards 11β-substituted steroids such as cortisol or corticosterone (Table III).

The apparent $K_i$ values were then determined for 4-azasteroid (4-MA and MK-906) inhibition of 5α-reductases expressed in COS cells. Studies were initially carried out in vitro following a protocol in which two concentrations of [$^{14}$C]testosterone substrate were employed in the presence of increasing concentrations of a given inhibitor. The data obtained were analyzed using Dixon plots to determine the type of inhibition and the apparent $K_i$ value (Dixon et al., 1979). The results for both inhibitors with the rat and human enzymes are summarized in Table III. The 4-MA compound was found to inhibit both the rat and human enzymes in a competitive fashion with an apparent $K_i$ in the low nanomolar range, an observation in accord with previously reported values. MK-906 was much less potent as an inhibitor of the human enzyme ($K_i$=340–620 nM), than it was of the rat enzyme ($K_i$=3–5 nM).

IC$_{50}$ values for MK-906 and 4-MA inhibition of 5α-reductases expressed in COS cells were also determined. Both compounds were equipotent in inhibiting the rat enzyme, however, 4-MA was approximately ten-fold more potent than MK-906 in inhibiting human steroid 5α-reductase 1. See Example 6 and FIG. 15, for further analysis of 4-aza-steroid inhibition.

described by Sambrook et al., 1989. Washed filters were exposed to X-ray film (Kodak XRP-1) for 1–10 min at room temperature.

Polymerase Chain Reactions. Amplification of individual or parts of exons was accomplished using exon-specific oligonucleotide pairs, e.g. as in Table IV and FIG. 8, (Saiki et al., 1988). In a typical reaction, 1 μg of genomic DNA was added to 100 μl of 10 mM Tris-Cl, pH 8.3, 50 mM KCl, 1.5 mM MgCl$_2$, 0.01% (w/v) gelatin, containing the four deoxynucleoside triphosphates (1.25 mM each) and 20 μM of each oligonucleotide primer. If the amplified DNA was to be sequenced by the chemical method (Maxam & Gilbert, 1980), one $^{32}$-P-end-labeled oligonucleotide was included per amplification reaction (Sambrook et al., 1989). The thermocycler conditions used in Example I were as follows: Exon 1, amplified in two halves, 5' or 3' halves=10 min/94° C., 35 cycles of 1 min/94° C. plus 3 min/68° C., 10 min/68° C.; Exons 2,3, and 4=10 min/94° C., 35 cycles of 1 min/94° C. plus 30 sec/55° C. plus 2 min/72° C., 10 min/72 ° C.; and Exon 5=10 min/94° C., 35 cycles of 1 min/95° C. plus 5 min/60°, 10 min 60° C. Amplified DNA was purified on a

TABLE III

Characterization in vitro of rat and human steroid 5α-reductases expressed in transfected COS cells.

| | RAT | | | HUMAN | | |
|---|---|---|---|---|---|---|
| SUBSTRATE | $K_m$ (μM) | $V_{max}$ (nmol/min/mg protein) | $K_i$ (nM) | $K_m$ (μM) | $V_{max}$ (nmol/min/mg protein) | $K_i$ (nM) |
| Testosterone | 2.5 | 1.4–2.5 | — | 3.6 | 0.7–3.6 | — |
| Androstenedione | 2.8 | 1.3–2.2 | — | 1.7 | 1.1–5.3 | — |
| Progesterone | 0.5 | 1.2–1.8 | — | 0.8 | 1.1–5.0 | — |
| Cortisol | — | <0.1 | — | — | <0.1 | — |
| Corticosterone | — | <0.1 | — | — | <0.1 | — |
| INHIBITOR | | | | | | |
| 4-MA | — | — | 5.0, 7.0 | — | — | 7.0, 8.0 |
| MK-906 | — | — | 3.0, 4.0, 5.0 | — | — | 340, 380, 620 |

COS cell transfection, cell homogonate preparation, and enzyme assay were carried out as described in Materials and Methods. Each $K_m$ value represents the average of at least two experiments carried out on different days using cell lysates prepared from different transfections. Although both enzymes were active against cortisol and corticosterone, the amounts of 5α-reduced products formed were too small to obtain accurate kinetic constants.

Example 3

Molecular genetic evidence for more than one human steroid 5α-reductase.

3A: Protocols Employed.

Materials. Enzymes for Southern blotting, RFLP analysis and DNA cloning and sequencing were obtained from New England Biolabs, Amersham and US Biochemicals. Nylon membranes were obtained from ICN Pharmaceuticals (Biotrans) and Bio-Rad (Zeta-Probe). Thermus aquaticus (Taq) DNA polymerase was obtained from Perkin Elmer-Cetus. [α-$^{32}$P]dCTP (3,000 Ci/mmol) was obtained from Du Pont-New England Nuclear and [γ-$^{32}$P]ATP (7,000 Ci/mmol) from ICN Radiochemicals. Oligonucleotides were synthesized on Applied Biosystems 380A and 380B DNA synthesizers. A thermocycler for use in polymerase chain reactions was obtained from Perkin Elmer-Cetus.

Southern Blotting. Fibroblasts from normal and steroid 5α-reductase deficient subjects were gown to confluency in 15 cm dishes and the genomic DNA isolated with an Applied Biosystems Model 340A Nucleic Acid Extractor.

$^{32}$P-radiolabeled probes were prepared by 5'-end labeling of oligonucleotides with [γ-$^{32}$P]ATP using bacteriophage T4 polynucleotide kinase (Sambrook et al., 1989). Hybridization in aqueous solution and washing were carried out as neutral 5% (w/v) polyacrylamide gel in a buffer containing 50 mM Tris-borate, pH 8.3 and 1 mM EDTA, electroeluted, extracted with phenol/chloroform (1:1) and chloroform, and precipitated in ethanol containing 0.8M ammonium acetate prior to DNA sequence analysis or subcloning.

RFLP Analysis. A HinfI polymorphism present in exon 1 of the steroid 5α-reductase gene was scored as follows. Genomic DNA (1 μg) corresponding to a portion of exon 1 containing the polymorphic site was amplified with oligonucleotides h5a35 and h5a36 (Table V) to yield a 210 bp fragment. The polymerase chain reaction was carried out in 10 mM Tris-HCl, pH 8.3, 50 mM KCl, 1.5 mM MgCl$_2$, 0.01% (w/v) gelatin for 35 cycles of 95° C. denaturation (1 min) and 68° C. annealing and extension (3 min) in an automated thermocycler (Perkin Elmer-Cetus). Initial denaturation was at 95° C. for 10 min and a final extension was at 68° C. for 10 min. After amplification, the DNA was digested with 10 units of HinfI for 3 hours at 37° C., fractionated on a 5% (w/v) neutral polyacrylamide gel in 50 mM Tris- borate, pH 8.3, 1 mM EDTA, transferred to Zeta-Probe membranes by electrophoresis at 30 volts for 3 hours in 0.5× electrophoresis buffer, and covalently linked to the filter by treatment with UV light (UV Stratalinker, Stratagene Corp., LaJolla, Calif.). These membranes were then subjected to Southern blotting using a radiolabeled h5a35 probe, as described above. In example I, the presence of the HinfI site led to cleavage of the 210 bp fragment into a 5' 138 bp fragment and a 3' 72 bp fragment.

An Nsp 7524 I (NspI) polymorphism in exon 2 of the steroid 5α-reductase gene was similarly detected by amplification of a 288 bp exon 2-containing fragment from genomic DNA using olignucleotides h5a14 and h5a8 (Table V) followed by digestion with NspI. The samples, in 10 mM Tris-HCl, pH 8.3, 50 mM KCl, 1.5 mM $MgCl_2$, 0.01% (w/v) gelatin, were initially denatured at 94° C. for 1 min, and then subjected to 35 cycles of annealing at 55° C. for 30 seconds and extension at 72° C. for 2 min. The amplified DNA was digested with 10 units of NspI for 3 hours at 37° C., fractionated by electrophoresis and subjected to Southern blotting and autoradiography as described above, using radiolabeled probes from oligonucleotides h5a14 and h5a8.

DNA Sequencing. DNA sequencing by the chemical method was performed, on both strands of the DNA, from at least two independent amplification reactions (Maxam & Gilbert, 1980). Dideoxy-mediated chain-termination DNA sequencing was carried out on exon-containing fragments subcloned into the bacteriophage M13 vectors mp18 and mp19 (Sanger et al., 1977; Messing, 1983). For each exon of the steroid 5α-reductase gene, 3 independent clones from each strand of the DNA were subjected to sequence analysis. DNA sequence data was analyzed on an IBM-PC AT computer using a MicroGenie program (Beckman, Corp.).

3B:Results.

The DNA from multiple individuals with steroid 5α-reductase deficiency was collected and analyzed. The subjects studied were of different ethnic origins and included probands from geographically isolated populations, consanguineous marriages, and a family with multiple affected progeny (Table IV). The levels of steroid 5α-reductase enzyme activity in fibroblasts biopsied from these individuals were found to vary from the low end of normal (1–100 pmol dihydrotestosterone formed/mg protein/hr) to below the level of detection. One subject (#71) expressed an unstable enzyme, while three subjects (#106, 490, and 667) expressed low levels of steroid 5α-reductase activity with altered $K_m$s for testosterone and/or NADPH. The mutations in these four individuals were predicted to be in the coding region of a steroid 5α-reductase gene. It was considered possible for the mutations giving rise to the apparent null alleles to map throughout the gene.

Genomic DNA from each of the affected individuals (Table IV) was digested with the restriction enzymes EcoRI, BamHI, HindIII, and BglII and subjected to Southern blotting analysis. Hybridization was carried out with radiolabeled probes derived from either the human steroid 5α-reductase cDNA, SRD5A1, or from multiple exons of the cloned gene. No rearrangements were detected that altered the structure of the gene, suggesting that if mutations were present, they would most likely be small rearrangements or point mutations.

Figure 8:
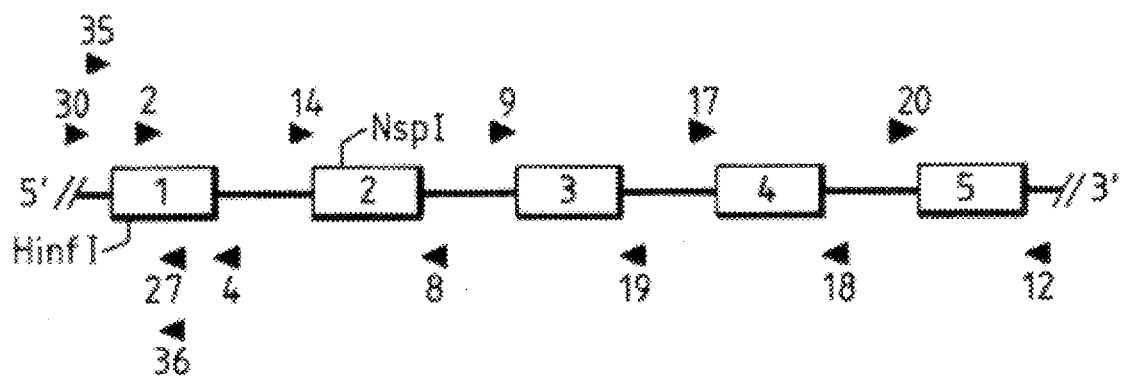
FIG. 8. Schematic of steroid 5α-reductase 1 gene (SRD5A1) and location of oligonucleotide primers. The five exons of the gene are shown as numbered boxes connected by thick lines representing introns or 5' and 3' flanking regions. The locations and orientations of oligonucleotide primers used in amplification reactions are shown above and below the gene. The locations of polymorphic HinfI and NspI sites are shown in exons 1 and 2, respectively. The gene schematic is not drawn to scale.

The structure of the gene at the nucleotide level was examined by synthesizing a series of oligodeoxynucleotide primers for use in the polymerase chain reaction. The sequence and locations of the multiple primers that were used to amplify the five exons of the gene are shown in Table V and FIG. 8. Exon 1 was amplified in two halves, whereas exons 2 through 5 were amplified as individual DNA fragments. The locations of the primers were such that mutations in the coding region or at the 5' or 3' splice junctions could be detected (FIG. 8).

All exons of the steroid 5α-reductase genes of five subjects were amplified and their DNA sequences determined by both direct chemical and enzymatic sequencing methods. Inasmuch as a history of consanguinity was denied in four of these individuals (#71,106,490, and 667, Table IV), it is possible that they were each compound heterozygotes possessing two mutant alleles at the steroid 5α-reductase locus. A fifth subject (#526) was the product of a consanguineous marriage, and presumably was a true homozygote, inheriting the same mutant allele from both parents.

No mutations were detected that altered the coding region or splice junctions of any of the exons of these five subjects. Given the altered biochemical phenotypes of the enzyme in four of the individuals (Table IV), this data suggests that mutations in the SRD5A1 gene were not responsible for steroid 5α-reductase deficiency.

Figures 9A, 9B:
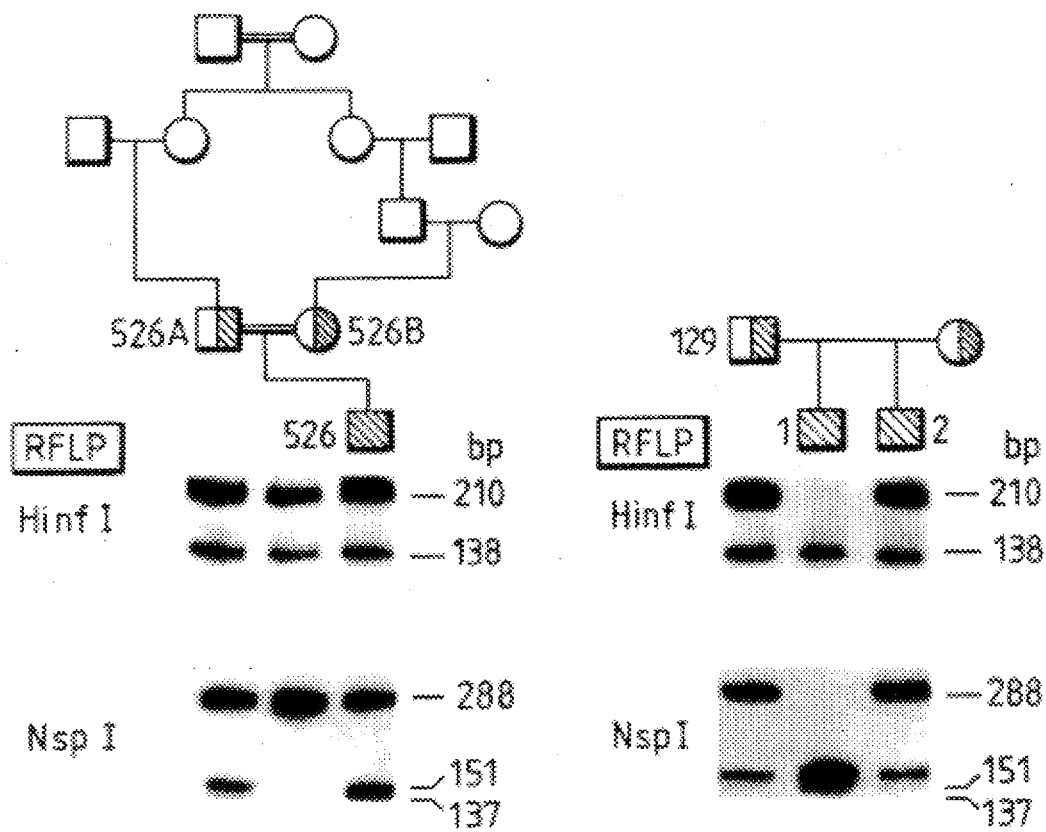
FIG. 9A–9B. Absence of homozygosity at steroid 5α-reductase 1 in consanguineous family and different genotypes in a family with two affected individuals. Upper left: pedigree of a family in which multiple consanguineous matings have taken place. DNA was isolated from the obligate heterozygous father (526A, Table I) and mother (526B), and the homozygous affected child (526), and scored for the presence of HinfI and NspI RFLPs in the steroid 5α-reductase 1gene. Lower left: autoradiogram of the results. The child is seen to be heterozygous for both RFLPs. Right: a similar analysis of a family with two affected members (subjects 1 and 2, Table I). DNA was available for analysis from only one parent (the father, 129, Table I) of this family. The two affected individuals are seen to have different genotypes with respect to the HinfI and NspI polymorphisms.

To obtain further genetic evidence to support this hypothesis, the affected individuals were genotyped with respect to HinfI and NspI RFLPs (Table IV). In a pedigree with multiple consanguineous matings, heterozygosity for both RFLPs was observed in the inbred affected offspring (subject 526, Table IV) of a marriage between first cousins once removed (FIG. 9, left panel). Similarly, subject 904 (Table IV), a product of a consanguineous marriage, was also found to be heterozygous for both markers. On analysis of a family with two affected individuals (subjects 1 and 2, of Table IV), the offspring were found to have different genotypes (FIG. 9, right panel). One was homozygous for the presence of both the HinfI and NspI sites, while the second was heterozygous for both markers.

TABLE IV

Clinical Information on Steroid 5α-Reductase Deficient Patients

| Fibroblast Strain | Initials | Origin | Consanguinity | DNA Sequence | RFLP Genotype HinfI | RFLP Genotype NspI | Enzyme Activity ± pmol/mg protein/hr | Reference |
|---|---|---|---|---|---|---|---|---|
| 71 | C.C. | U.S. Black | No | Yes | –, – | –, – | 3.0, abnormal $K_m$ for NADPH, unstable enzyme | 16 |
| 106 | M.U. | Sicily | No | Yes | +, – | +, – | 0.6, abnormal $K_m$ for NADPH and T | 17 |
| 490 | M.M. | Malta | No | Yes | +, + | +, + | 0.6, abnormal $K_m$ for NADPH and T | 18 |
| 667 | A.B. | Austria | No | Yes | +, – | –, – | 1.6, abnormal pH optima, abnormal $K_m$ for T | 19 |
| 526 | T.A. | Latvia | Yes | Yes | +, – | +, – | <0.2 | this study |
| 526A | J.A. | Latvia, father | Yes | No | +, – | +, – | N.D. | this study |

TABLE IV-continued

Clinical Information on Steroid 5α-Reductase Deficient Patients

| Fibroblast Strain | Initials | Origin | Consanguinity | DNA Sequence | RFLP Genotype HinfI | RFLP Genotype NspI | Enzyme Activity ± pmol/mg protein/hr | Reference |
|---|---|---|---|---|---|---|---|---|
| 526B | V.A. | Latvia, father | Yes | No | +, − | −, − | N.D. | this study |
| 1 | S.J. | U.S. Black | No | No | +, + | +, + | <0.2 | 14 |
| 2 | J.J. | U.S. Black | No | No | +, − | +, − | <0.2 | 14 |
| 129 | W.J. | U.S. Black, father | No | No | +, − | +, − | N.D. | 14 |
| 41 | M.C. | Dominican Republic | Yes | No | +, − | −, − | <0.2 | 15 |
| 339 | F.C. | Dominican Republic | Yes | No | −, − | −, − | <0.2 | this study |
| NG2 | Y.A. | New Guinea | Yes | No | +, − | +, − | <0.2 | 27 |
| NG3 | I.K. | New Guinea | Yes | No | +, − | +, − | <0.2 | 27 |
| NG4 | T.S. | New Guinea | Yes | No | +, − | +, − | <0.2 | 27 |
| 904 | M.K. | Pakistan | Yes | No | +, − | +, − | <0.2 | this study |

*(+) presence of indicated site; (−), absence of indicated site. The order of + and − symbols is arbitrary phase of the RFLPs on chromosome 5 was not determined.
*Determined as described in reference 14, T = Testosterone.

The RFLPs of affected individuals from two geographically isolated populations were analysed, including two individuals (Subjects 41 and 338, Table IV) from Dominican Republic village in which isolation and extensive consanguinity had been well documented (Peterson et al., 1977). Subject 41 was heterozygous for the presence of the HinfI site, while subject 338 was homozygous for the absence of the site. Both individuals were homozygous for the absence of the NspI site. Three affected individuals (NG2, NG3, and NG4, Table IV) from an isolated tribe in the highlands of New Guinea (Imperato-McGinley et al., 1991) were similarly found to have different genotypes. Subjects NG2 and NG4 were heterozygous for both RFLPs, while subject NG3 was homozygous for the presence of the HinfI site and heterozygous for the NspI site. Taken together, the results of FIG. 9 and the RFLP analyses, provided convincing genetic evidence that mutations in the SRD5A1 gene did not underlie steroid 5α-reductase deficiency. This exclusion also eliminated possibilities such as differential splicing (Padgett et al., 1986), RNA editing (Weiner & Maizels, 1990), alternate translational reading frames (Shaw et al., 1983) and ribosome frameshifting (Atkins et al., 1990) as explanations for the absence of mutations in the subjects whose genes were sequenced. As, if these posttranscriptional events had occurred, the disease would still have segregated with the cloned gene. This data therefore most strongly supported the existence of more than one steroid 5α-reductase enzyme in human tissues.

TABLE V

Sequence and location of oligonucleotides used for polymerase chain reactions

| Oligonucleotide | Location | Amplification Target | Sequence 5' →3' |
|---|---|---|---|
| h5a30 | Exon 1 | 5' half Exon 1 | GGCCTCTGGGCCATGGAGCACGCTGCCCAGCCCTC |
| h5a27 | Exon 1 | 5' half Exon 1 | GGCACTCGGAGCCTGTGGCTGGGCA |
| h5a2 | Exon 1 | 3' half Exon 1 | GGAATCGTCAGACGAACTCAGTGTA |
| h5a4 | Intron 1 | 3' half Exon 1 | GTCGGAGAGGACGCCGGGCCGGGAG |
| h5a14 | Intron 1 | Exon 2 | CCCAAATCATTTAAGATAGGATTAC |
| h5a8 | Intron 2 | Exon 2 | ATGATGTGAACHAGGCGGAGTTCAC |
| h5a9 | Intron 2 | Exon 3 | TGAAATTTTACGGTTTATTAGCCATAAT |
| h5a19 | Intron 1 | Exon 3 | AGCAACTTTCACACAAATTCTTCAC |
| h5a17 | Intron 1 | Exon 4 | CCGTATTTCATTTTGTAGTAAATGG |
| h5a18 | Intron 4 | Exon 4 | TAGTCAAAGAACAAATTACAAATGG |
| h5a20 | Intron 4 | Exon 5 | CATTGGTTAAATGTCTAAGCGACAG |
| h5a12 | Exon 5 | Exon 5 | AAAGTCCATAGAGHAGCGCCATTGG |
| h5a35 | Exon 1 | HinfI RFLP Exon 1 | CAGGATCCGAGGCCTCTGGGGCATGGAGCACGCTGCCCAGCCCTG |
| h5a36 | Exon 1 | HinfI RFLP Exon 1 | CGAAGCTTCAGGCACTCGGAGCCTGTGGCTGGGCA |

Sequence of oligonucleotide h5a30 is position 811–846 of SEQ ID NO: 7; h5a27 is position 990–975 of SEQ ID NO: 7; is position 936–961 of SEQ ID NO: 7; h5a4 is position 30–55 of SEQ ID NO: 9; h5a14 is position 20–45 of SEQ ID NO: 10; h5a8 is position 17–38 of SEQ ID NO: 13; h5a9 is position 50–77 of SEQ ID NO: 14; h5a19 is position 13–38 of SEQ ID NO: 17; h5a17 is position 48–72 of SEQ ID NO: 18; h5a18 is position 21–43 of SEQ ID NO: 21; h5a20 is position 43–67 of SEQ ID NO: 22; h5a12 is SEQ ID NO: 35; h5a35 is SEQ ID NO: 36; h5a36 is SEQ ID NO: 37.

Example 4

Characterization of the SRD5A1 gene.

To isolate genomic DNA sequences homologous to SRD5A1, three human genomic DNA libraries, (#s 946204 and #943202, Stratagene Corp.; #HL1067J, Clontech Corp.), in bacteriophage γ vectors were screened at high stringency with [$^{32}$P]-labeled probes derived from the SRD5A1 cDNA (Sambrook et al., 1989). Thirty-two hybridization-positive clones were identified among 2×10$^6$ plaques, each of which was initially divided into one of several classes based on their abilities to hybridize with 5' and 3' radiolabeled cDNA fragments. Further characterization of these clones by restriction mapping, Southern blotting and DNA sequence analysis, revealed the existence of two non-identical genes.

The partial sequence and organization of these genes was determined. Firstly, SRD5A1, spanned over 35 kilobases (kb) and contained 5 exons separated by 4 introns (FIG. 10) SEQ ID NOS: 7, 9–11, 13–15, 17–19, and 21–23, respectively. With the exception of polymorphisms (see below), the DNA sequence of the five exons exactly matched the sequence of the cDNA for steroid 5α-reductase 1. The lengths of the exons varied from 0.102 to 1.359 kb, while those of the introns varied from 4.1 to over 14 kb. The 5'-flanking region of the gene contained a TATA sequence and several consensus sequences for the Sp1 transcription factor (Kadonaga et al., 1986). The near identical location of the TATA sequences of the rat and human genes suggested that the 5' end of the cDNA (FIG. 10) (SEQ ID NO: 23) represented the cap site of the gene. The sequences at the intron-exon boundaries of the gene matched those of the consensus mammalian splice donor and acceptor sites (Padgett et al., 1986), and the sizes of the five exons agreed well with those predicted by the exonscanning model of splicing (Robberson et al., 1990).

Figure 11:
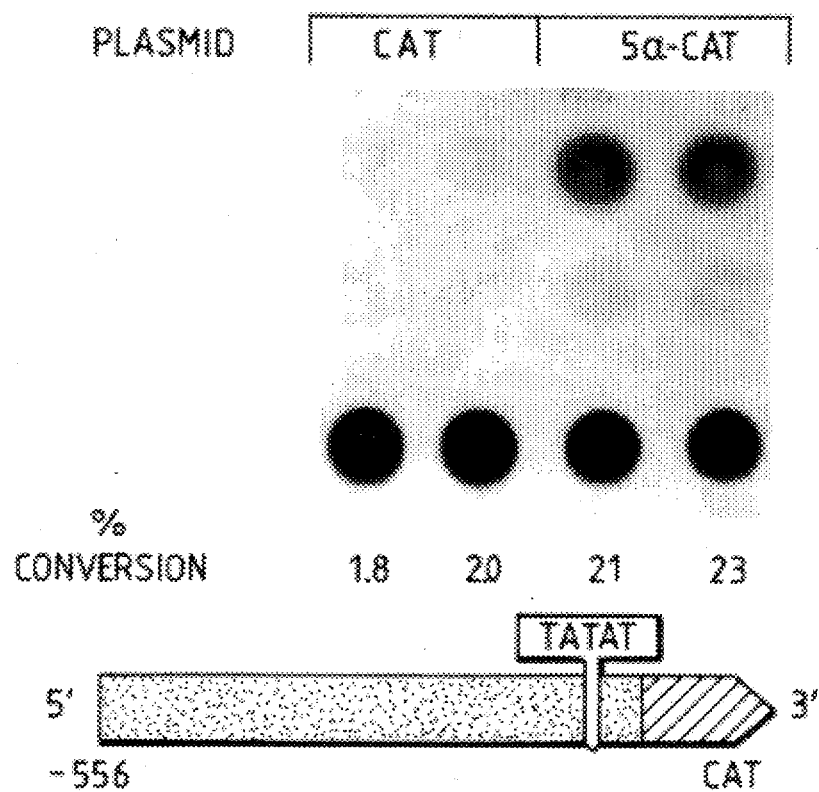
FIG. 11. Transfection of steroid 5α-reductase-CAT chimeric gene into cultured mammalian cells. Human HepG2 cells were transfected with a plasmid containing the bacterial CAT gene alone (CAT) or a fragment of the steroid 5α-reductase gene linked to the CAT gene (5α-CAT). Forty-eight hours after transfection, cells were harvested and cell extracts corresponding to 25 β-galactosidase units (Herbomel et al., 1984) were assayed in duplicate for 2 hr at 37° C., prior to determining CAT enzyme activity by thin layer chromatography. An autoradiogram is shown of the results. The percentage of the starting [$^{14}C$]chloramphenicol substrate converted into acetylated product was determined by scintillation counting of the appropriate zones from the chromatogram. A schematic of the steroid 5α-reductase-CAT gene is shown at the bottom of the figure.

The 5'-flanking region of the SRD5A1 gene was assayed for its ability to drive transcription of a marker gene. A 0.528 kb fragment (nucleotides −556 to −28, FIG. 10) (position 293–818 of SEQ ID NO: 7) from the 5'-end of the gene was fused to the bacterial chloramphenicol acyltransferase (CAT) gene. The resulting chimeric construct was transfected, at sub-confluency using a calcium phosphate protocol (Sambrook et al., 1989), into cultured human hepatoma cells (HepG2) grown in monolayer in Dulbecco's minimal essential medium containing 10% fetal calf serum. Two plasmids were introduced simultaneously into the cells, a test plasmid containing a bacterial chloramphenicol acyltransferase gene (pBLCAT3, Luckow and Schutz, 1987), and a normalization plasmid containing a bacterial β-galactosidase gene linked to the Simian virus 40 early region promoter and enhancer (pCH110, Searle et al., 1985). 48 to 72 hours after transfection, cells were lysed by freeze-thawing and assayed for the presence of β-galactosidase activity (Sambrook et al., 1989). Aliquots of cell lysates containing equal amounts of β-galactosidase activity were then assayed for CAT enzyme activity (Sambrook et al., 1989). Results were expressed as percent conversion of starting [$^{14}$C]chloramphenicol substrate into acylated products. The inclusion of the 0.528 kb fragment from the 5'-end of the SRD5A1 gene in the CAT plasmid resulted in the transient expression of CAT enzyme activity (FIG. 11).

DNA sequence analysis of the exons of the human SRD5A1 gene revealed two discrepancies between the sequence of the cDNA and those of exons 1 and 2. Both alterations occurred in the third position of a codon and would not result in a change of the amino acid sequence of the enzyme (FIG. 10, circled nucleotides). However, each nucleotide change had the potential to disrupt the recognition sequence of a restriction enzyme. The G to C change in exon 1 was present in the first position of a HinfI site (GANTC), whilst the A to G change in exon 2 was present in the third position of an NspI site (A/GCATGC/T).

To determine if the observed changes represented potentially useful RFLPs, DNA corresponding to exons 1 or 2 was amplified from genomic DNA using the polymerase chain reaction (PCR) and assayed for HinfI or NspI sites (Example 3, methods). When DNA from a small family was analyzed, the HinfI site was found to be polymorphic and segregated as a co-dominant marker in the offspring (FIG. 12, left panel). Analysis of 52 chromosomes from 26 unrelated individuals indicated that the allele containing the site was present at a frequency of 0.58, whilst the allele lacking the site was present at a frequency of 0.42. Similar results were obtained for the NspI site in exon 2. In a four member family, the presence or absence of the site was seen to segregate in a co-dominant fashion (FIG. 12, right panel). Analysis of 56 chromosomes indicated that the frequency of the allele containing the site was 0.45 and was 0.55 for the allele lacking the site.

Example 5

Identification and characterization of cDNA encoded by SRD5A2, the gene encoding the major functional steroid 5α-reductase isozyme in human genital tissue.

The evidence described above most strongly suggested the existence of other cDNAs encoding additional active steroid 5α-reductases. However, as screening genomic libraries with homologous DNA sequences did not result in the isolation of the major isozyme in genital tissue, a different strategy, that of expression cloning, was employed. The method, as described below, has the advantage that identified proteins will have at least some steroid 5α-reductase activity.

A size-fractionated and oriented cDNA library was constructed from human prostate poly A$^+$ mRNA in a pCMV expression vector using a kit purchased from GIBCO-BRL (Andersson et al,, 1989a, 1989t), Serial dilution transfection experiments, using an expression vector containing the 5α-reductase 1 cDNA and an irrelevant cDNA library, were employed to determine the size of cDNA pools that were to be screened for expression of 5α-reductase in cultured human embryonic kidney 293 cells. Enzyme activity in transfected cells was detected over background (3-fold) when the 5α-reductase 1 cDNA was diluted 10$^4$-fold. Based on this information, the cDNA was electroporated into *E. coli* HB101 cells, and pools of approximately 104 independent cDNAs were grown overnight in 10 ml cultures of superbroth media (Sambrook et al., 1989). Plasmid DNA was prepared using Quiagen-tip 100 columns, 5 μg aliquots were transfected via a calcium phosphate procedure (Gorman et al., 1990) into 60 mm dishes of human embryonic kidney 293 cells (ATCC #CRL 1573). To enhance expression, 0.5 μg of a plasmid (pVA1) containing the adenovirus VAI gene was cotransfected with the pooled cDNAs (Gorman et al., 1990). On day 2 of the transfection experiments, [$^{14}$C]testosterone (120 dpm/pmol) was added to the medium at a final concentration of 1 μM, and conversion into dihydrotestosterone was determined 18 hours later (Andersson et al, 1989; Andersson & Russell, 1990), A pool expressing 5α-reductase enzyme activity was also screened with a probe generated by a PCR in which two oligonucleotides, GA(A/G)TGGTG(T/C)T(T/A)(T/C)GCN (C/T)TNGC (SEQ ID NO: 32) and TTIGG(A/G)TAITC(T/C)TC(A/G)AA(T/C)TT (SEQ ID NO: 33), encoding amino acids 205 to 211 and 243 to 249 of the human and rat 5α-reductase 1 proteins respectively, were used to amplify random-primed cDNA synthesized from 0.4 μg of total human prostate RNA. The reaction conditions were those of Strathmann et al., 1989, except that 30 second incubations at 94° C., 40° C., and 72° C. were used in place of those described. A 91 best pair product whose DNA sequence was 57% identical to the corresponding region of the human 5α-reductase 1 cDNA was generated. Hybridization positives were obtained at a frequency of approximately 1 in $10^4$ when this product was used to screen an expressing pool of prostate cDNAs. This result, combined with DNA sequence analysis of a hybridization-positive clone (see below), indicated that both approaches had identified the same cDNA.

The coding and 3'-untranslated regions of the 2.437 kb cDNA insert in the expression plasmid was determined (FIG. 13) (SEQ ID NO: 5). The protein encoded by this cDNA was predicted to be a hydrophobic polypeptide of 254 amino acids. The sequence of this protein, termed steroid 5α-reductase 2, was determined to be 50% identical to that of human 5α-reductase 1 and 46% identical to the rat 5α-reductase enzyme (FIG. 14) (SEQ ID NO: 2, 4, and 6, respectively). All three proteins shared almost identical hydropathy plots, despite their relatively low sequence identity.

A search of the data bases indicated that residues 10 to 85 of human 5α-reductase 2 shared a 38% sequence identity with residues 231 to 305 of the tobacco chloroplast NADH-ubiquinone oxidoreductase chain 5 protein (Shinozaki et al., 1986), and that residues 9 to 72 shared a 39% identity with residues 222 to 281 of the pol polyprotein of the Cas-Br-E murine leukemia virus (Rassart et al., 1986). The entire 5α-reductase 2 protein was found to be 28% identical to residues 264 to 462 of the Epstein-Barr virus terminal proteins (Laux et al., 1988), which suggested that the latter proteins may bind steroids or NADPH.

Example 6

Biochemical and pharmacological characterization of human steroid 5α-reductase isozymes.

Steroid 5α-Reductase Assay. Steroid 5α-reductase activity was assayed by measuring the conversion of testosterone into dihydrotestosterone (DHT). Assays were conducted in 0.5 ml of 0.1M Tris-Cl and 0.1M sodium citrate, in the presence of 1, 2, 4 or 10 μM [$^{14}$C]testosterone (50–60 mCi/mmol, Du Pont-New England Nuclear) and 10 mM NADPH, for 20 or 30 minutes at 37° C. The precise conditions and pH for each experiment are indicated in the figure legends. Termination, organic extraction and TLC were performed as described in Example 1, using a chloroform-ethyl acetate (3:1, v/v) mobile phase in the TLC.

Prostate tissue was obtained from subjects undergoing surgical treatment for benign prostatic hyperplasia from Dr. J. McConnell (University of Texas Southwestern Medical Center, Dallas, Tex.), immediately frozen in liquid nitrogen and stored at −70° C. until preparation of extracts. Briefly, a 5 g sample of frozen tissue was pulverized in liquid nitrogen and then homogenized in 3 volumes (~15 ml) of 20 mM potassium phosphate, pH 6.5, 0.32M sucrose, 1 mM EDTA with a polytron followed by a glass-teflon Potter-Elvhem homogenizer. The resulting homogenate was filtered through cheese cloth to remove fibrous particulate matter and then centrifuged for 1 hr at 4° C. at 100,000 xg. The membrane pellets were resuspended in ~15 ml of the above buffer using a glass-teflon homogenizer and again collected by centrifugation. The final membrane pellets were resuspended at a protein concentration of 5–10 mg/ml in 20 mM potassium phosphate, pH 7.0, 20% (v/v) glycerol using the glass-teflon homogenizer, and stored at −70° C. in small aliquots.

Cultured simian COS-M6 cells were transfected with a steroid 5α-reductase expression vector (Andersson at al., 1989b) and the steroid 5α-reductase activity was determined 48 hours subsequent to transfection. Cells were harvested, washed once with phosphate-buffered saline and either frozen in liquid $N_2$ or adjusted to a protein concentration of 2 mg/ml in 10 mM potassium phosphate, pH 7.4, 150 mM KCl, 1 mM EDTA and homogenised directly using a polytron. A typical assay contained 10–50 μg of cell homogenate protein in 0.5 ml 100 mM potassium phosphate, steroids were added in 5 μl ethanol and the reaction initiated by the addition of NADPH to a final concentration of 2–5 mM. Termination, organic extraction and TLC were performed as described above.

4B:Results.

The major steroid 5α-reductase enzyme expressed in human genital skin fibroblasts and prostate has been reported to have a pH optimum of approximately 5.0 (Moore et al., 1975; Liang et al., 1985). This value was confirmed using prostate extract, which also served to establish the suitability of the assay technique used herein.

Initially, steroid 5α-reductase 1 cDNA was expressed in Simian kidney COS cells prior to preparation and assay of cell lysates. Steroid 5α-reductase 1 was found to be maximally active over the broad pH range, 6.0 to 8.5. On mixing 5α-reductase 1 and prostate extract, two distinct peaks of activity were detected, with optima of pH 5.0 and 7.0–8.0. These results indicated that the presence of inhibitors or modifiers in either of the two extracts did not explain the differing pH optima.

Figure 15B:
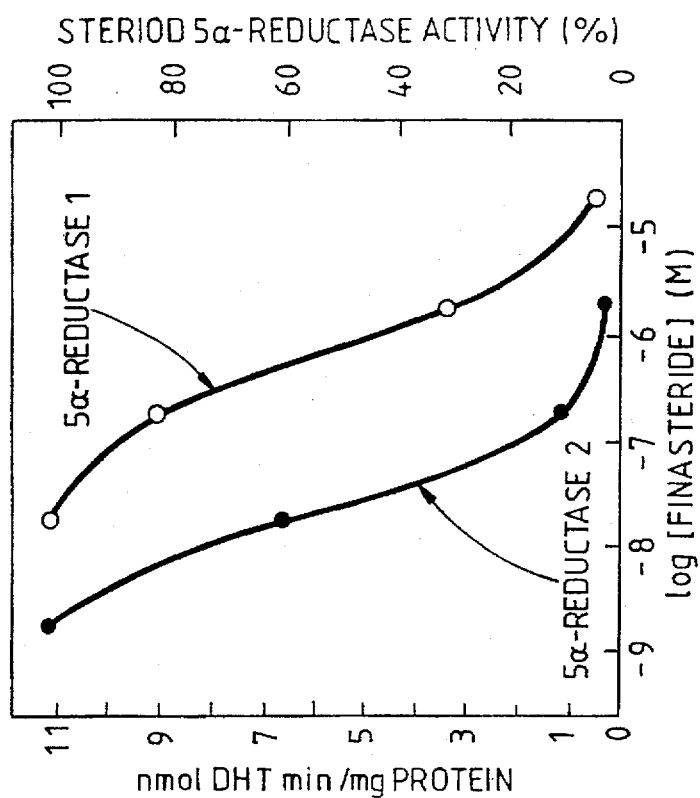
FIGS. 15A–15B. Characterization of expressed human 5α-reductase isozymes with regard to pH optima and finasteride inhibition. Expression plasmids containing the 5α-reductase 1 or 2 cDNAs (FIGS. 7 and 13, respectively) were transfected into human embryonic kidney 293 cells. Panel A: 48 hours after transfection, long of cell protein was assayed for 5α-reductase enzyme activity in 0.1M Tris-citrate buffers at the indicated pH with 10 μM [$^{14}$C] testosterone (120 dpm/pmol) as substrate and 10 mM NADPH as cofactor. Non-transfected cells express negligible levels of enzyme activity. Panel B: 5 μg of transfected cell protein were assayed in duplicate for 5α-reductase activity in the presence of the indicated concentration of finasteride (MK-906) (17β-(N-t-butyl)carbamoyl-4-aza-5α-androst-1-en-3-one), 4 μM [$^{14}$C]testosterone (120 dpm/pmol) and 10 mM NADPH. Reductase enzyme activity obtained in extracts of transfected human embryonic kidney 293 cells in the absence of inhibitor was defined as 100%. In both panels, conversion into dihydrotestosterone was determined, after 10 minute incubations, by thin layer chromatography. Protein concentrations in cell extracts were measured as in Lowry, 1951.
Figure 15A:
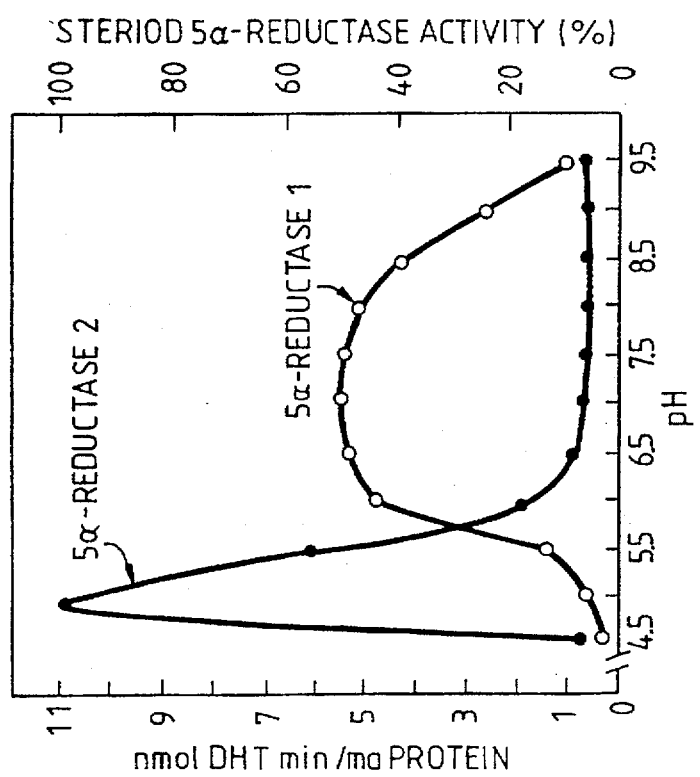

Secondly, cDNAs encoding either the steroid 5α-reductase 1 or 2 isozymes was expressed in human embryonic kidney 293 cells, which allowed the properties of the resultant enzymes to be compared directly. A broad and basic pH optimum was confirmed for steroid 5α-reductase 1 (FIG. 15A). However, steroid 5α-reductase 2 was found to have a narrow and acidic pH optimum, centred around pH 5.0 (FIG. 15A), which is in close agreement with previously published data for the genital form of the enzyme (Moore et al., 1975; Liang et al., 1985).

The effect of finasteride (MK-906), a known competitive inhibitor of the major human prostate 5α-reductase enzyme (Liang et al., 1985), on the steroid 5α-reductase isozymes was investigated. Firstly, the apparent $K_i$ values for finasteride inhibition of prostate extracts and steroid 5α-reductase 1, expressed in COS cells, were determined. These assays were conducted at the respective pH optima of 5.0 and 7.0. In this system, the enzyme in the prostate extract was inhibited by finasteride with an apparent $K_i$ of ~3 nM, but the corresponding value for steroid 5α-reductase 1 was ~300 nM. The $IC_{50}$ values of the prostate extract and the steroid 5α-reductase 1 expressed in COS cells, were also vastly different, being 10 nM and 10 μM, respectively. On mixing aliquots of the two extracts that contained equivalent 5α-reductase activity, the resulting inhibition curve was biphasic, which confirmed the presence of two distinct enzymes.

The properties of the two human steroid 5α-reductase isozymes were also compared directly, following expression in human embryonic kidney 293 cells. The 5α-reductase 1 cDNA was again poorly inhibited by finasteride ($IC_{50}$ ~900 nM, $K_i$ ~230 nM), however 5α-reductase 2, inkeeping with the known properties of the genital isoform, was markedly inhibited, $IC_{50}$ ~30 nM, $K_i$ ~5 nM (FIG. 15B).

Example 7

Mutations in the human steroid 5α-reductase 2 isozyme are present in patients with pseudohermaphroditism.

The possibility of steroid 5α-reductase 2 gene mutations existing in subjects with 5α-reductase deficiency was investigated by screening the DNA from multiple affected individuals for gene rearrangements. Genomic DNA was isolated from peripheral blood samples and 20 μg aliquots were digested with HindIII and Southern blotted at high. stringency using three single stranded [$^{32}$P]-labelled probes which spanned the coding region of the 5α-reductase 2 cDNA (Feinberg & Vogelstein, 1983; Church and Gilbert, 1983). After autoradiography for 5 days at −70° C., the filter was stripped (Sambrook et al., 1989) and reprobed with a random hexanucleotide [$^{32}$P]-labelled probe corresponding to the full-length 5α-reductase 1 cDNA. As a control, the same DNAs were screened with a probe from the 5α-reductase 1 cDNA.

Figure 16A:
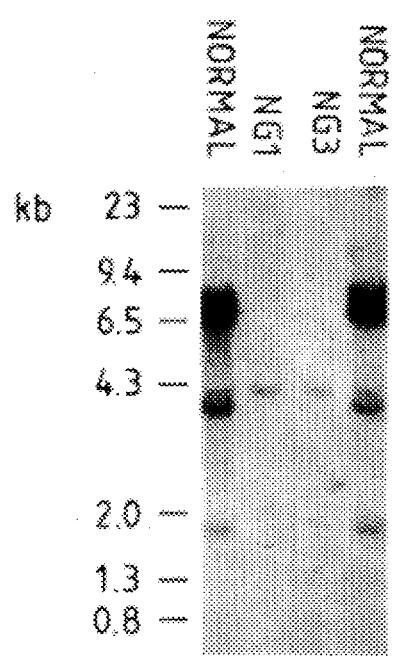
FIGS. 16A–16B. Deletion of 5α-reductase 2 gene in subjects with 5α-reductase deficiency. DNA isolated from two normal individuals and two related 5α-reductase deficiency subjects from a geographically isolated tribe in the Highlands of Papua New Guinea was screened by Southern blotting using the indicated 5α-reductase cDNA probes. Normal DNA was isolated from an individual from the same New Guinea tribe as the NG1 and NG3 subjects and a Caucasian American (left and right lanes, respectively). The filter was screened with the 5α-reductase 2 cDNA probe, then stripped and reprobed with the 5α-reductase 1 cDNA probe. A deletion of all but a weakly hybridizing fragment of approximately 4.5 kilobases in the DNA of the affected NG1 and NG3 individuals is apparent from the autoradiogram obtained with the 5α-reductase 2 probe. All individuals have a normal 5α-reductase 1 gene.
Figure 16B:
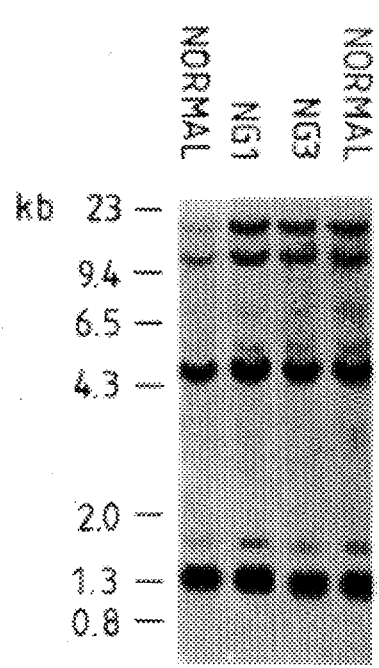

A deletion in the 5α-reductase 2 gene was found in two related pseudohermaphrodites from the Simbari Anga linguistic group in the Highlands of Papua New Guinea (Imperato-McGinley et al., 1991) but was not present in the DNA of a normal individual from this tribe (FIG. 16). The deletion had removed a majority of the 5α-reductase 2 gene from the affected individuals, as only a single weakly hybridizing fragment was visible on the autoradiogram (FIG. 16). No gross rearrangements in the 5α-reductase 2 gene were detected in affected individuals derived from nineteen different pedigrees from throughout the world. This indicated that, as with many other genetic diseases (Hobbs et al., 1990), a majority of the mutations cannot be detected by Southern blotting.

This was the final piece of evidence that confirmed that the steroid 5α-reductase 2 protein, encoded by the SRD5A2 gene, was the major isozyme in genital tissue.

Example 8

Identification and characterization of a steroid 5α-related pseudogene.

In screening human genomic libraries, two hybridizing sequences with different structures were identified, one of which proved to be a functional gene SRD5A1 (see above, Example 4). The second of these sequences was analysed, as described immediately below, and determined to be a pseudogene, SRD5AP1.

The SRD5AP1 pseudogene was found to be 95% identical to the type 1 cDNA in the coding region (FIG. 17) (SEQ ID NOS: 25 and 27, respectively), but did not contain introns. The predicted protein sequence encoded by SRD5AP1 was two amino acids longer than the cDNA-encoded steroid 5α-reductase as a consequence of a duplication of 6 base pairs (GCGACG) encoding an Ala-Thr pair at the amino terminus. SRD5AP1 contained a termination codon in place of that specifying amino acid 147 of steroid 5α-reductase 1 (FIG. 17). The presence of the stop codon was independently confirmed in the genomes of 6 unrelated individuals by amplifying and sequencing this region of DNA, suggesting that this alteration did not represent a cloning artefact.

The 5'- and 3'-ends of SRD5AP1 were found to have unusual structures. The 5'-boundary was homologous to SRD5A1 to a point that was just upstream of the TATA sequence, whereupon a sequence corresponding to the 3'-end of a human long interspersed nucleotide element (LINE sequence) was encountered (FIG. 17) (SEQ ID NOS: 25 and 27, respectively). The 3'-end was homologous to SRD5A1 up to a point corresponding to nucleotide 1990 in the 3'-untranslated region of the cDNA (Andersson and Russell, 1990). After which, SRD5AP1 terminated in 8 adenine residues (FIG. 17) (SEQ ID NOS: 25 and 27, respectively). 12 bp perfect direct repeats (GATTCAGATCAC) were located at the 5'- and 3'-boundaries of SRD5AP1. These features of SRD5AP1 are consistent with it being a non-functional processed pseudogene (Vanin, 1984).

By analysing the sequences according to Li et al., (1981), it was estimated that the event leading to the formation of the pseudogene occurred approximately 10 million years ago (Pilbeam, 1984), Accordingly, members of the primate superfamily Hominoidea that diverged from man less than 10 million years ago, such as the gorilla and chimpanzee, should contain the pseudogene, whereas those that diverged prior to this event, such as the orangutan and gibbon, should not. The apparent absence of a second hybridizing sequence in mouse (see below) was consistent with the estimated time of pseudogene formation.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Adelman et al. (1983), *DNA*, 2:183.
Agarwal, A. K., Monder, C., Echstein, B., and White, P. C. 1989. *J. Biol. Chem.* 264: 18939–18943.
Andersson, S., R. W. Bishop, and D. W. Russell. 1989a. *J. Biol. Chem.* 264:16249–16255.
Andersson, S., Davis, D., Dahlbäck, Jörnvall, H., and Russell, D. W. 1989b *J. biol. Chem.* 264, 8222–8229.
Andersson, S., and D. W. Russell. 1990. *Proc. Natl. Acad. Sci. USA* 87:3640–3644.
Atkins, J. F., R. B. Weiss, and R. F. Gesteland. 1990. *Cell* 62:413423.
Bolivar et al. (1977), *Gene*, 2:95.
Brooks, J. R., et al. 1981 *Endocrinol.* 109, 830–836.
Bruchovsky, N., P. S. Rennie, F. H. Batzold, S. L. Goldenberg, T. Fletcher, and M. G. McLoughlin. 1988. *J. Clin. Endorinol. Metab.* 67:806–816.
Cheng, K. C. (1988), *FASEB J.*, 2:355 (Abstr.).
Church, G. M. & Gilbert, W. 1983. *Proc. Natl. Acad. Sci. USA* 81: 1991–1995.
Crea et al. (1978), *Proc. Natl. Adad. Sci. U.S.A.*, 75:5765.
Cunha, G. R., et al. 1987. *Endocr. Rev.*, 8:338–362.
Davisson, M. T., Lallay, P. A., Peters, J., Doolittle, D. P., Hillyard, A. L., Searle, A. G. 1990. *Cytogenet. Cell. Genet.* 55: 434–456.
DeMartinville, B., Kunkel, L. M., Bruns, G., Morle, F., Koenig, M., Mandel, J. L., Horwich, A., Latt, S. A., Gusella, J. F., Houseman, D., Franks, U., 1985. *Am. J. Hum. Genet.* 37: 235–249.

Dixon, J., et al. (1979), *Enzymes* (Academic press, New York, N.Y.).

Elliott, R. W., Daniel, W. L., Taylor, B. A., and Novak, E. K. 1985. *J. Hered*, 76: 243–246.

Farkash, Y., et al. (1988), *Proc. Natl. Acad. Sci.. U.S.A.*, 85:5824–5828.

Feinberg, A., and Vogelstein, B. 1983. *Anal. Biochem.* 132: 6–13.

Fiers et al. (1978), *Nature*, 273:113.

Fisher, L. K., et al. (1978), *J. Clin. End. Metab.*, 47:653–664.

Francke, U., Yang-Feng, T. L., Brissenden, J. E., and Ullrich, A. 1986. *Cold Spring Harbor Symposia On Quantitative Biology* 51: 855–866.

Frankel, W. N., Stoye, J. P., Taylor, B. A., AND Coffin, J. M. 1989. *J. Virol.* 63: 1763–1774.

Frederiksen, D. W., et al. (1971), *J. Biol. Chem.*, 246:2584–2593.

Geliebter, J., et al. (1986), *Proc. Natl. Acad. Sci. U.S.A.*, 83:3371–3375.

Gonzalez, F. J. (1989), *Pharm. Rev.*, 40:243–288.

Gorman, C. M., Gies, D. R., and McCray, G. 1990 *DNA ptn. Eng. Tech.* 2, 3–10.

Griffin, J. E. & Wilson, J. D. in *The Metabolic Basis of Inherited Disease* (eds Scriver, C. R., Beaudet, A. L., Sly, W. S., & Valle, D) 1919–1944 (New York: McGraw-Hill 1989).

Hediger, M. A., et al. (1987), *Nature*, 330:379–381.

Hess et al. (1968), *J. Adv. Enzyme Reg.*, 7:149.

Hitzeman et al. (1980), *J. Biol. Chem.*, 255:2073.

Hobbs, H. H., Russell, D. W., Brown, M. S., and Goldstein, J. L. 1990 *Annu. rev. Genet.* 24, 133–170.

Holland et al. (1978), *Biochemistry*, 17:4900.

Hsieh, C.-L., Vogel, U. S., Dixon, R. A. F., and Francke, U. 1989 *Somat. Cell Mol. Genet.* 15 579–590.

Hsieh, C.- L., Sturm, R., Herrr, W., and Francke, U. 1990 *Genomics* 6: 666–672.

Imperato-McGinley, J., and T. Gautier. 1986. *Trends In Gen.* 2:130–133.

Imperato-McGinley, J., M. Miller, J. D. Wilson, R. E. Peterson, C. Shackleton, and D. C. Gajdusek. 1991. *Clinical Endocrinol.* 34:293–298.

Itami, S., S. Kurata, T. Sonoda, and S. Takayasu. 1991. *J. Invest. Dermat.* 96:57–60.

Jobling et al. (1987), *Nature*, 325:622–625; Browning et al. (1988), *JBC*, 263:9630–9634.

Jones (1977), *Genetics*, 85:12.

Julius, D., et al. (1988), *Science*, 84:4332–4336.

Kadonga, J. T., Jones, K. A., and Tjian, R. 1986. *Trends in Biochemical Science* 11: 20–23.

Kingsman et al. (1979), *Gene*, 7:141.

Kozak, M. (1986), *Cell*, 44:283–292.

Kruse and Peterson, editors, *Tissue Culture*, Academic Press, (1973).

Kyte, J., et al. (1982), *J. Mol. Biol.*, 157:105–132.

Laux, G., Perricaudet, M., and Farrell, P. J. 1988 *EMBO J.* 7, 769–774.

Lehrman, M. A., W. J. Schneider, T. C. Südhof, M. S. Brown, J. L. Goldstein, and D. W. Russell. 1985. *Science* 227:140–146.

Li, W-H., Gojobori, T., and Nei, M. 1981. *Nature* 292: 237–239.

Liang, T., M. A. Cascieri, A. H. Cheung, G. F. Reynolds, and G. H. Rasmusson. 1985. *Endocrinology* 117:571–579.

Lippman, M. E. (1981), *William's Textbook of Endocrinology*, (Wilson et al., eds.) pp. 1309–1326, 7th Ed., W. B. Saunders Company, Philadelphia.

Lowry, O. H., Rosebrough, N. J., Farr, A. L., and Randall, R. J. 1951 *J. biol. Chem.* 193, 265–275.

Lubbert, H., et al. (1987), *Proc. Natl. Acad. Sci. U.S.A.*, 84:4332–4336.

Luckow, B., and Schutz, G. 1987 *Nucl. Acids Res.* 15: 5490.

Lyon, M. F., Kirby, M. C. 1990 *Mouse Genome* 87: 28–54.

Masu, Y., et al. (1987), *Nature*, 329:836–838.

Maxam, A. M., and W. Gilbert. 1980. *Methods Enzymol.* 65:499–560.

McGuire, J. S., Jr. and G. M. Tomkins. 1960. *J. Biol. Chem.* 235:1634–1638.

Metcalf, B. W., et al. (1989), *Trends in Pharmaceutical Science*, 10:491–495.

Messing, J. 1983. *Methods Enzymol.* 101:20–78.

Miller, W. L. (1988), *Endocr. Rev.*, 2:295–318.

Mooradian, A. D., et al. 1987. *Endocr. Rev.*, 8:1–28.

Moore, R. J., and J. D. Wilson. 1972. *J. Biol. Chem.* 247:958–967.

Moore, R. J., et al. (1973), *Endocrinology*, 93:581–592.

Moore, R. J., J. E. Griffin, and J. D. Wilson. 1975. *J. Biol. Chem.* 251:7168–7172.

Moore, R. J., and J. D. Wilson. 1976. *J. Biol. Chem.* 251:5895–5900.

Munke, M., Harbers, K., Jaenisch, R., AND Francke, U. 1986 *Cytogenet. Cell Genet.* 43: 140–149.

Noma, Y., et al. (1986), *Nature*, 319:640–646.

Okayama et al. (1983), *MCB*, 3:280–289.

Padgett, R. A., P. J. Grabowski, M. M. Konarska, S. Seiler, and Sharp, P. A. 1986 *Ann. Rev. Biochem.* 55:1119–1150.

Peacock, S. L., et al. (1988), *J. Biol. Chem.*, 263:7838–7845.

Peterson, R. E., J. Imperato-McGinley, T. Gautier, and E. Sturla. 1977. *Am. J. Med.* 62:170–191.

Pilbeam, D. 1984. *Scientific Am.* 250: 84–96.

Rassart, E., Nelbach, L., and Jolicoeur, P. 1986 *J. Virol.* 60, 910–919.

Robberson, B. L., Cote, G. J., and Berget, S. M. 1990. *Mol. and Cell. Biol.* 10: 84–94.

Saiki, R. K., D. H. Gelfand, S. Stoffel, S. J. Scharf, R. Higuchi G. T. Horn, K. B. Mullis, and H. A. Erlich. 1988. *Science* 239:487–491.

Sambrook, J., E. F. Fritsch, T. Maniatis. 1989. *Molecular Cloning: A Laboratory Manual*, Cold Spring Harbor Laboratory, Cold Spring Harbor, N.Y. 1–18.8.

Sanger, F., S. Nicklen, and A. R. Coulson. 1977. *Proc. Natl. Acad. Sci. USA* 74:5463–5467.

Schneider, J. J. 1952. *J. Biol. Chem.* 199:235–244.

Schweinfest, C. W., et al. (1982), *Proc. Natl. Acad. Sci. U.S.A.*, 79:4997–5000.

Searle, P. F., Stuart, G. W. and Pelmiter, R. D. 1985 *Mol. Cell. Biol.* 5:1480–1485.

Seeburg (1982), *DNA*, 1:239–249.

Sharp. 1986. *Annu. Rev. Biochem.* 55:1119–1150.

Shaw, M. W., P. W. Choppin, and R. A. Lamb. 1983. *Proc. Natl. Acad. Sci. USA* 80:4879–4883.

Shinozaki, K., et al. 1986 *EMBO J.* 5, 2043–2049.

Siebwenlist et al. (1980), *Cell*, 20:269.

Smith, L. M., Sanders, J. Z., Kaiser, R. J., Hughes, P., Dodd, C., Connel, C. R., Heiner, C., Kent, S. B. H., and Hood, L. E. 1986. *Nature* 321: 674–679.

Stinchcomb et al. (1979), *Nature*, 282:39.

Strathmann, M., Wilkie, T. M., and Simon, M. I. 1989 *Proc. Natl. Acad. Sci. U.S.A.* 85, 7407–7409.

Sufhof, T. C., et al. (1987), *Cell*, 48:1061–1069.

Thomsen et al. (1984), *PNAS*, 81:659–663. See also Boshart et al. (1985), *Cell*, 41:521–530.

Tilley, W. D., et al. (1989), *Proc. Natl. Acad. Sci. U.S.A.*, 86:327–331.

Tschemper et al. (1980), *Gene*, 10:157.

Vanin, E. F. 1984. *Biochim. Biophys. Acta* 782: 231–241.
Vermeulen, A., Giagulli, V. A., DeSchepper, P., Buntinx, A., and Stoner, E. 1989 *Prostate* 14, 45–53.
Walter, P., et al. (1981), *J. Cell Biol.*, 91:545–550.
Wieacker, P., Davies, K. E., Cooke, H. J., Pearson, P. L., Williamson, R., Bhattacharya, S., Zimmer, J., Ropers, H-H. 1984 *Amer. J. Hum. Genet.* 36: 265–276.
Weiner, A. M., and N. Maizels. 1990. *Cell* 61:917–920.

Wilson, J. D. 1975. *Handb. Physiol.* 5:491–508.
Wilson, J. D. 1978. *Ann. Rev. Physiol.*, 40:279–306.
Wilson, J. D. 1980. *Am. J. Med.* 68:745–756.
Wilson, J. D. 1985 *Harvey lecture Series* 79, 145–172.
Yang-Feng, T. L., Degennaro, L. J. and Francke, U. 1986 *proc. Natl. Acad. Sci.* 83:8679–8683.
Yates, F. E., et al. (1958), *Endocrinology*, 63:887–902.

---

What is claimed is:

1. A method for the production of a steroid 5α-reductase comprising the steps of:
   (a) preparing a recombinant host cell comprising a DNA segment encoding a steroid 5α-reductase; and
   (b) culturing the recombinant host under conditions effective to allow the production of said steroid 5α-reductase by the host.

2. The method of claim 1, wherein said steroid 5α-reductase is a human steroid 5α-reductase.

3. The method of claim 1, wherein said steroid 5α-reductase is a rat steroid 5α-reductase.

4. The method of claim 2, wherein said steroid 5α-reductase is a human genital tissue steroid 5α-reductase.

5. A method for determining the ability of a candidate substance to affect the enzymatic activity of a steroid 5α-reductase, comprising the steps of:
   (a) preparing a steroid 5α-reductase in accordance with claim 1; and
   (b) testing said steroid 5α-reductase so produced with a candidate substance to determine the ability of the substance to affect an enzymatic function of said steroid 5α-reductase.

6. The method of claim 5, wherein said steroid 5α-reductase is tested to determine whether it is inhibited by said candidate substance.

7. The method of claim 5, wherein said steroid 5α-reductase is human steroid 5α-reductase.

8. The method of claim 7, wherein said steroid 5α-reductase is a human genital tissue steroid 5α-reductase.

9. The method of claim 2, wherein said human steroid 5α-reductase has the sequence of SEQ ID NO: 4.

10. The method of claim 3, wherein said rat steroid 5α-reductase has the sequence of SEQ ID NO: 2.

11. The method of claim 4, wherein said human genital tissue steroid 5α-reductase has the sequence of SEQ ID NO: 6.

12. The method of claim 7, wherein said human steroid 5α-reductase has the sequence of SEQ ID NO: 4.

13. The method of claim 7, wherein said human genital tissue steroid 5α-reductase has the sequence of SEQ ID NO: 6.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 2470 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 10..774

( x i ) SEQUENCE DESCRIPTION: SEQ ID NO:1:

```
ACCTCAGCT ATG GAG TTG GAT GAG CTG TGC CTG CTC GAC ATG CTG GTC        48
          Met Glu Leu Asp Glu Leu Cys Leu Leu Asp Met Leu Val
           1               5                      10

TAC TTG GAA GGT TTC ATG GCC TTC GTG TCC ATT GTG GGG CTC CGG TCG      96
Tyr Leu Glu Gly Phe Met Ala Phe Val Ser Ile Val Gly Leu Arg Ser
     15              20                  25

GTT GGC TCT CCG TAC GGC CGC TAC TCG CCG CAG TGG CCC GGC ATC CGA     144
Val Gly Ser Pro Tyr Gly Arg Tyr Ser Pro Gln Trp Pro Gly Ile Arg
 30              35                  40                      45

GTG CCC GCG CGA CCT GCC TGG TTC ATA CAG GAG CTG CCC TCG ATG GCC     192
Val Pro Ala Arg Pro Ala Trp Phe Ile Gln Glu Leu Pro Ser Met Ala
             50                  55                  60

TGG CCG CTG TAC GAG TAC ATT CGT CCT GCA GCC GCG CGA CTG GGC AAC     240
Trp Pro Leu Tyr Glu Tyr Ile Arg Pro Ala Ala Ala Arg Leu Gly Asn
             65                  70                  75

CTG CCT AAC CGC GTC CTG CTG GCT ATG TTT CTG ATC CAC TAC GTG CAA     288
Leu Pro Asn Arg Val Leu Leu Ala Met Phe Leu Ile His Tyr Val Gln
         80                  85                  90

AGG ACG CTG GTT TTC CCG GTT CTG ATC AGG GGA GGG AAG CCC ACC CTC     336
Arg Thr Leu Val Phe Pro Val Leu Ile Arg Gly Gly Lys Pro Thr Leu
     95                 100                 105

CTG GTC ACC TTT GTC TTG GCC TTC CTG TTC TGC ACC TTC AAC GGC TAT     384
Leu Val Thr Phe Val Leu Ala Phe Leu Phe Cys Thr Phe Asn Gly Tyr
110             115                 120                     125

GTA CAG AGC AGA TAC TTG AGC CAG TTT GCG GTT TAT GCT GAA GAC TGG     432
Val Gln Ser Arg Tyr Leu Ser Gln Phe Ala Val Tyr Ala Glu Asp Trp
             130                 135                 140

GTG ACC CAT CCC TGT TTC CTG ACA GGC TTT GCC CTG TGG TTA GTG GGC     480
Val Thr His Pro Cys Phe Leu Thr Gly Phe Ala Leu Trp Leu Val Gly
             145                 150                 155

ATG GTG ATA AAT ATC CAC TCA GAC CAC ATC CTG AGG AAT CTG AGA AAA     528
Met Val Ile Asn Ile His Ser Asp His Ile Leu Arg Asn Leu Arg Lys
             160                 165                 170

CCA GGG GAA ACT GGA TAC AAG ATA CCC AGG GGA GGC CTG TTT GAA TAC     576
```

```
                Pro Gly Glu Thr Gly Tyr Lys Ile Pro Arg Gly Gly Leu Phe Glu Tyr
                    175                 180                 185

GTA TCT GCA GCC AAC TAT TTT GGG GAG CTC GTG GAG TGG TGT GGC TTT       624
Val Ser Ala Ala Asn Tyr Phe Gly Glu Leu Val Glu Trp Cys Gly Phe
190                 195                 200                 205

GCA CTG GCC AGC TGG TCC CTC CAG GGT GTA GTG TTT GCA CTG TTC ACA       672
Ala Leu Ala Ser Trp Ser Leu Gln Gly Val Val Phe Ala Leu Phe Thr
                210                 215                 220

CTC AGC ACA CTG CTC ACC AGA GCG AAG CAG CAC CAT CAG TGG TAC CAT       720
Leu Ser Thr Leu Leu Thr Arg Ala Lys Gln His His Gln Trp Tyr His
            225                 230                 235

GAG AAG TTT GAA GAT TAC CCC AAG TCA AGA AAA ATA CTG ATT CCA TTT       768
Glu Lys Phe Glu Asp Tyr Pro Lys Ser Arg Lys Ile Leu Ile Pro Phe
        240                 245                 250

GTG CTT TAGTGCTCTG TTAGCGCTGT TGCCTCCCAT GAGCTGAGTC TGTCTGTCTC        824
Val Leu
    255

CCTGGTGACT TTGCTCTGAG CACTTACGAA TGAATTGTTT TCCTTAATTC CCTGCAGCC       884
CCTTTCTCAG GAAAGGCTGG GGGTGGGGGG GTGTCGTCCC CTGGTAAAGG ACAAAGCCAA       944
TGATAAACTA ATCCACCACA TGCAGTTAGG GGCTACACTG CCTGCTGGAT CCGAAGCAGG      1004
TAGCCCTGAG TCATTATGGG GCTCTCTGAC TTCAGCAATC AGCAGCCCTT ACAATCCTGC      1064
AAGATTCCAC CCAAGTCAGC AGCAGTCACG GGCCTCCTTC ACTGATGTGT GTTCTGCCTG      1124
CTCAGCCCCT GCCACAGAGG CCTGGAGGTG TGGGAGTGTG GCCTAAGCAC AGTCTGCCAT      1184
CCTTGACCGC AGACCTCTTG GACCCACCCC CACTCCCTCC AGACACTGGT AAGAGAAGCC      1244
TTCCTGCAAC ATGTCCTGTC CTCAGGAGGT GAGACAGCAG AGTGCTTCCA TTCACTCGAT      1304
GACCCCATTT TTGCTCTTCC TTTGGGCTAG AATTCATTAA GGTCCTTAAA AACAAAACAA      1364
AACTTTTTCT TAATAGTACA AAACAAAATA TCAAAACAAA ATTTGTTATT TTGAATGCAC      1424
CCAAGGACCA ATCATGTCAC ACAAAGAAAG CTCAGGGCTA GCCTGGGCTG TGTAGGGAGA      1484
CCCTGTTTGG GAAAAAAAA ATGAAGATAA CAACCAGCTA ACTGTCCAAA GAAGTGACCG      1544
CAGTAATAAA AGACGCCGCC CACACAGGCA CCAGCTTGGG AGAAAGATGT GCGCCTGGGA      1604
TTGTAAACCC ACTGTTGCTC TGGGCAGGCT GAGGCCCACT GGTGAAGAGC CATTCCCACC      1664
GGACCCATGC ACACTGCCTC GGGGCAGCGT CTGCACTCAC CTCTCACCCG CTGCCACCAC      1724
AGCTAAAGAA CAGAACGGAT AGAACTGTGT GCTCTGAACC CAGTGAAGAT GCTGCATGAA      1784
GACCTGCAGG CACACCTGAT GGCGTGCACG GTGCCCACCA CTCGCCTGAC TCGGACCATC      1844
TCTGTGTGCC CGCTGCCACC TCTGTGTGCC CTTTCCAGCT GGCTTTCCCA TCAGGGCTTC      1904
CTCAGCTCTT CTGCTCTCAG ACAGAAACTA TTCTCTGTTC CTCTGGTTCG CAGAATGTCT      1964
AGATTTGACC CAGAAAACTT CATGACACAG CTACTTCATT TTAACAAAGA GCAGTGTTTA      2024
ATGGGGAACT ACCCTTCAAT CCTTTACCCT CCCCTTTTCT GGCCAAGTAA CTGCTTGAAA      2084
ACCTAAAGCA CTAAACATTG TAGGTCTCCT CTCAAAACCT CAGGCCTGTC TGGTGTGTTC      2144
TGAAACGTTT GTGTGGAAGG AGATATTCAG CTGAGACCCT GGGAATGTTT GCTGTGAACT      2204
TGACCTCCCT TGGAGGGCAT GGTGCTAGAT AAACTTGGAA CCTAGGACTC CAGGTTGCTA      2264
GGCGGATGCC CTGACACTAA GCCACATCAC ACATTAGCTC TGTGATGCCT CTTTCTTTAT      2324
GAAGGACCAA GCTGCCCACA TACTAAGTGA GATTAATTTA AGAGGAATCC TGTCCTAACA      2384
CTGTATACTT CATTCCCTAC AACTCAACTT ACTTGTATGA ACCATGATTG TTAAGGAAAT      2444
TAATAAACTA CATTTATAAG TAAAAA                                          2470
```

( 2 ) INFORMATION FOR SEQ ID NO:2:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Leu Asp Glu Leu Cys Leu Leu Asp Met Leu Val Tyr Leu Glu
 1               5                  10                  15
Gly Phe Met Ala Phe Val Ser Ile Val Gly Leu Arg Ser Val Gly Ser
                20                  25                  30
Pro Tyr Gly Arg Tyr Ser Pro Gln Trp Pro Gly Ile Arg Val Pro Ala
            35                  40                  45
Arg Pro Ala Trp Phe Ile Gln Glu Leu Pro Ser Met Ala Trp Pro Leu
        50                  55                  60
Tyr Glu Tyr Ile Arg Pro Ala Ala Ala Arg Leu Gly Asn Leu Pro Asn
 65                 70                  75                  80
Arg Val Leu Leu Ala Met Phe Leu Ile His Tyr Val Gln Arg Thr Leu
                85                  90                  95
Val Phe Pro Val Leu Ile Arg Gly Gly Lys Pro Thr Leu Leu Val Thr
            100                 105                 110
Phe Val Leu Ala Phe Leu Phe Cys Thr Phe Asn Gly Tyr Val Gln Ser
        115                 120                 125
Arg Tyr Leu Ser Gln Phe Ala Val Tyr Ala Glu Asp Trp Val Thr His
    130                 135                 140
Pro Cys Phe Leu Thr Gly Phe Ala Leu Trp Leu Val Gly Met Val Ile
145                 150                 155                 160
Asn Ile His Ser Asp His Ile Leu Arg Asn Leu Arg Lys Pro Gly Glu
                165                 170                 175
Thr Gly Tyr Lys Ile Pro Arg Gly Gly Leu Phe Glu Tyr Val Ser Ala
            180                 185                 190
Ala Asn Tyr Phe Gly Glu Leu Val Glu Trp Cys Gly Phe Ala Leu Ala
        195                 200                 205
Ser Trp Ser Leu Gln Gly Val Val Phe Ala Leu Phe Thr Leu Ser Thr
    210                 215                 220
Leu Leu Thr Arg Ala Lys Gln His His Gln Trp Tyr His Glu Lys Phe
225                 230                 235                 240
Glu Asp Tyr Pro Lys Ser Arg Lys Ile Leu Ile Pro Phe Val Leu
                245                 250                 255
```

( 2 ) INFORMATION FOR SEQ ID NO:3:

( i ) SEQUENCE CHARACTERISTICS:
        ( A ) LENGTH: 2107 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 31..807

( x i ) SEQUENCE DESCRIPTION: SEQ ID NO:3:

```
GGGCATGGAG CACGCTGCCC AGCCCTGGCG ATG GCA ACG GCG ACG GGG GTG GCG      54
                                 Met Ala Thr Ala Thr Gly Val Ala
                                  1               5
```

| | | | | | | | | | | | | | | | |
|---|---|---|---|---|---|---|---|---|---|---|---|---|---|---|---|
| GAG | GAG | CGC | CTG | CTG | GCC | GCG | CTC | GCC | TAC | CTG | CAG | TGC | GCC | GTG | GGC | 102
| Glu | Glu | Arg | Leu | Leu | Ala | Ala | Leu | Ala | Tyr | Leu | Gln | Cys | Ala | Val | Gly |
| | 10 | | | | 15 | | | | | 20 | | | | | |
| TGC | GCG | GTC | TTC | GCG | CGG | AAT | CGT | CAG | ACG | AAC | TCA | GTG | TAC | GGC | CGC | 150
| Cys | Ala | Val | Phe | Ala | Arg | Asn | Arg | Gln | Thr | Asn | Ser | Val | Tyr | Gly | Arg |
| 25 | | | | | 30 | | | | | 35 | | | | | 40 |
| CAC | GCG | CTG | CCC | AGC | CAC | AGG | CTC | CGA | GTG | CCG | GCG | CGG | GCC | GCC | TGG | 198
| His | Ala | Leu | Pro | Ser | His | Arg | Leu | Arg | Val | Pro | Ala | Arg | Ala | Ala | Trp |
| | | | | 45 | | | | | 50 | | | | | 55 | |
| GTG | GTG | CAG | GAG | CTG | CCC | TCG | CTG | GCC | CTG | CCG | CTC | TAC | CAG | TAC | GCC | 246
| Val | Val | Gln | Glu | Leu | Pro | Ser | Leu | Ala | Leu | Pro | Leu | Tyr | Gln | Tyr | Ala |
| | | | 60 | | | | | 65 | | | | | 70 | | |
| AGC | GAG | TCC | GCC | CCG | CGT | CTC | CGC | AGC | GCG | CCC | AAC | TGC | ATC | CTC | CTG | 294
| Ser | Glu | Ser | Ala | Pro | Arg | Leu | Arg | Ser | Ala | Pro | Asn | Cys | Ile | Leu | Leu |
| | | 75 | | | | | 80 | | | | | 85 | | | |
| GCC | ATG | TTC | CTC | GTC | CAC | TAC | GGG | CAT | CGG | TGC | TTA | ATT | TAC | CCG | TTT | 342
| Ala | Met | Phe | Leu | Val | His | Tyr | Gly | His | Arg | Cys | Leu | Ile | Tyr | Pro | Phe |
| | 90 | | | | | 95 | | | | | 100 | | | | |
| CTG | ATG | CGA | GGA | GGA | AAG | CCT | ATG | CCA | CTG | TTG | GCA | TGT | ACA | ATG | GCG | 390
| Leu | Met | Arg | Gly | Gly | Lys | Pro | Met | Pro | Leu | Leu | Ala | Cys | Thr | Met | Ala |
| 105 | | | | | 110 | | | | | 115 | | | | | 120 |
| ATT | ATG | TTC | TGT | ACC | TGT | AAC | GGC | TAT | TTG | CAA | AGC | AGA | TAC | TTG | AGC | 438
| Ile | Met | Phe | Cys | Thr | Cys | Asn | Gly | Tyr | Leu | Gln | Ser | Arg | Tyr | Leu | Ser |
| | | | | 125 | | | | | 130 | | | | | 135 | |
| CAT | TGT | GCA | GTG | TAT | GCT | GAT | GAC | TGG | GTA | ACA | GAT | CCC | CGT | TTT | CTA | 486
| His | Cys | Ala | Val | Tyr | Ala | Asp | Asp | Trp | Val | Thr | Asp | Pro | Arg | Phe | Leu |
| | | | 140 | | | | | 145 | | | | | 150 | | |
| ATA | GGT | TTT | GGC | TTG | TGG | TTA | ACA | GGC | ATG | TTG | ATA | AAC | ATC | CAT | TCA | 534
| Ile | Gly | Phe | Gly | Leu | Trp | Leu | Thr | Gly | Met | Leu | Ile | Asn | Ile | His | Ser |
| | | 155 | | | | | 160 | | | | | 165 | | | |
| GAT | CAT | ATC | CTA | AGG | AAT | CTC | AGA | AAA | CCA | GGA | GAT | ACT | GGA | TAC | AAA | 582
| Asp | His | Ile | Leu | Arg | Asn | Leu | Arg | Lys | Pro | Gly | Asp | Thr | Gly | Tyr | Lys |
| | 170 | | | | | 175 | | | | | 180 | | | | |
| ATA | CCA | AGG | GGA | GGC | TTA | TTT | GAA | TAC | GTA | ACT | GCA | GCC | AAC | TAT | TTT | 630
| Ile | Pro | Arg | Gly | Gly | Leu | Phe | Glu | Tyr | Val | Thr | Ala | Ala | Asn | Tyr | Phe |
| 185 | | | | | 190 | | | | | 195 | | | | | 200 |
| GGA | GAA | ATC | ATG | GAG | TGG | TGT | GGC | TAT | GCC | CTG | GCC | AGC | TGG | TCT | GTC | 678
| Gly | Glu | Ile | Met | Glu | Trp | Cys | Gly | Tyr | Ala | Leu | Ala | Ser | Trp | Ser | Val |
| | | | | 205 | | | | | 210 | | | | | 215 | |
| CAA | GGC | GCG | GCT | TTT | GCT | TTC | TTC | ACG | TTT | TGT | TTT | TTA | TCT | GGT | AGA | 726
| Gln | Gly | Ala | Ala | Phe | Ala | Phe | Phe | Thr | Phe | Cys | Phe | Leu | Ser | Gly | Arg |
| | | | 220 | | | | | 225 | | | | | 230 | | |
| GCA | AAA | GAG | CAT | CAT | GAG | TGG | TAC | CTC | CGG | AAA | TTT | GAA | GAG | TAT | CCA | 774
| Ala | Lys | Glu | His | His | Glu | Trp | Tyr | Leu | Arg | Lys | Phe | Glu | Glu | Tyr | Pro |
| | | 235 | | | | | 240 | | | | | 245 | | | |
| AAG | TTC | AGA | AAA | ATT | ATA | ATT | CCA | TTT | TTG | TTT | TAAGTGCGTT | TTTCATGAAA | | | | 827
| Lys | Phe | Arg | Lys | Ile | Ile | Ile | Pro | Phe | Leu | Phe | | | | | |
| | 250 | | | | | 255 | | | | | | | | | |

| | | | | |
|---|---|---|---|---|
| TTATCTTCAA | CTTGAAGCTT | TCCAATGGCG | CTTCTCTATG | GACTTTGTAA | ATAAGTTATA | 887
| TCTTTGTAAT | TTTCCTGCTA | CTTTATCATT | TTCAAGATGT | CCTCTAGGAA | TTTTTTTTCT | 947
| AGTAATTTTG | CAATCTACCT | AATAAGTACC | TAAATACGCT | GAAATGGAGG | TTGAATATCC | 1007
| TACTGTGTAA | CAGGTCAGAA | TTTCAAGCTC | TGGGTAATAA | CTGCTGATAT | TTTTCTAAT | 1067
| TTCAAATTTA | CCTCTTTTGG | CTATGTCTTG | CCAAGTGTGT | ATGAGACTAG | ACTTTACAAC | 1127
| TGTCTTTGAT | GGCATTTTCA | GAACAATAAA | TGTCACAATC | CCTTCTATAG | CCCCCTACAG | 1187
| TGATCTCTTC | AAGGTCAACT | GCAGTGTTGC | TTCCCTCCCC | CTATAGGGCT | GGAATCTGTC | 1247
| TAGGAGCCCT | CTCTCGGAGG | CCACAGAGGC | TGGGGGTAGC | CATTGTGCAG | TCATGGCCCG | 1307

```
GGGGAAACTT  GCCAACCTTC  GTGTCAGGTG  CTGTGTGTAA  GTGGAGAACT  TGGGGATAGA    1367

GGAGGAAGCT  CCTCGTGGCC  CTTCCAAGGT  GAGGCAAAGG  CATCTGGACT  TGTTCCAGCC    1427

CAGCCCACCG  GGTGACATCA  CCGGGCAGGG  AGGGGTGCTG  GTGGTGGTTC  ATACGGAGTA    1487

AGCTGCTCTG  CCTGTGTGAG  TGGCTCCTGG  GCCCTAAACA  GGCACCTTTA  GGCCATGGGT    1547

CACTCACCGT  GAGCCATCAA  TGTGCTCTGG  TCTGACATGG  TTTCTCTCTG  TCTTCTAGTC    1607

TAGACCTAGT  TTTTTGTTC   TGTTCCCCAC  GTATGGATAT  AGTAGAGATT  GTTGTCTGTG    1667

AAATTTCTCT  TTTGTAGATT  TGAGTTTTC   CCTTGTAGTG  TAAAGAATGA  TCACTTTCTG    1727

TAACAATAAC  AAGACCACTT  TTTAAGATTT  ATCCTGTTTG  TTCTTTGTTG  ATTGAAACAT    1787

AATAATTGTT  AAAATTCTCT  ACAGCCTTCT  TTTTCTTCCA  TAGCTAATCT  TCCTTCTAAT    1847

AGTTTTTGCT  TTCTGTTTTG  CTGTTGTTGC  TTTGCAAAGC  TTTCCCCTCA  TAGCCTGTAC    1907

CTGTTATCAA  TATAAAATAA  TCTTCCTGTT  GAATGCTTCA  TGACTTGAAT  TCTACTTTGA    1967

TAAAAACATT  GCCATACTGC  TTTTTATCTT  GATGAATTCA  TCTGGCATTG  CTTTGCCTTA    2027

TCATCTCATC  TGGAGTTTTT  AAATGCCATT  TGTTTCAGTT  GTCTTAACA   ACATAATAAA    2087

TAGACTTTGC  CATTTAAAAA                                                    2107
```

( 2 ) INFORMATION FOR SEQ ID NO:4:

( i ) SEQUENCE CHARACTERISTICS:
        ( A ) LENGTH: 259 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Thr  Ala  Thr  Gly  Val  Ala  Glu  Glu  Arg  Leu  Leu  Ala  Ala  Leu
 1                  5                        10                       15

Ala  Tyr  Leu  Gln  Cys  Ala  Val  Gly  Cys  Ala  Val  Phe  Ala  Arg  Asn  Arg
            20                       25                       30

Gln  Thr  Asn  Ser  Val  Tyr  Gly  Arg  His  Ala  Leu  Pro  Ser  His  Arg  Leu
         35                       40                       45

Arg  Val  Pro  Ala  Arg  Ala  Ala  Trp  Val  Val  Gln  Glu  Leu  Pro  Ser  Leu
      50                       55                       60

Ala  Leu  Pro  Leu  Tyr  Gln  Tyr  Ala  Ser  Glu  Ser  Ala  Pro  Arg  Leu  Arg
 65                       70                       75                       80

Ser  Ala  Pro  Asn  Cys  Ile  Leu  Leu  Ala  Met  Phe  Leu  Val  His  Tyr  Gly
                 85                       90                       95

His  Arg  Cys  Leu  Ile  Tyr  Pro  Phe  Leu  Met  Arg  Gly  Gly  Lys  Pro  Met
              100                      105                      110

Pro  Leu  Leu  Ala  Cys  Thr  Met  Ala  Ile  Met  Phe  Cys  Thr  Cys  Asn  Gly
           115                      120                      125

Tyr  Leu  Gln  Ser  Arg  Tyr  Leu  Ser  His  Cys  Ala  Val  Tyr  Ala  Asp  Asp
      130                      135                      140

Trp  Val  Thr  Asp  Pro  Arg  Phe  Leu  Ile  Gly  Phe  Gly  Leu  Trp  Leu  Thr
145                      150                      155                      160

Gly  Met  Leu  Ile  Asn  Ile  His  Ser  Asp  His  Ile  Leu  Arg  Asn  Leu  Arg
                 165                      170                      175

Lys  Pro  Gly  Asp  Thr  Gly  Tyr  Lys  Ile  Pro  Arg  Gly  Gly  Leu  Phe  Glu
              180                      185                      190

Tyr  Val  Thr  Ala  Ala  Asn  Tyr  Phe  Gly  Glu  Ile  Met  Glu  Trp  Cys  Gly
           195                      200                      205

Tyr  Ala  Leu  Ala  Ser  Trp  Ser  Val  Gln  Gly  Ala  Ala  Phe  Ala  Phe  Phe
```

210                      215                              220
Thr Phe Cys Phe Leu Ser Gly Arg Ala Lys Glu His His Glu Trp Tyr
225                     230                     235                     240

Leu Arg Lys Phe Glu Glu Tyr Pro Lys Phe Arg Lys Ile Ile Ile Pro
                    245                     250                     255

Phe Leu Phe ( 2 ) INFORMATION FOR SEQ ID NO:5:

( i ) SEQUENCE CHARACTERISTICS:
        ( A ) LENGTH: 2437 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 28..789

( x i ) SEQUENCE DESCRIPTION: SEQ ID NO:5:

```
GCGGCCACCG GCGAGGAACA CGGCGCG ATG CAG GTT CAG TGC CAG CAG AGC        51
                             Met Gln Val Gln Cys Gln Gln Ser
                              1               5

CCA GTG CTG GCA GGC AGC GCC ACT TTG GTC GCC CTT GGG GCA CTG GCC      99
Pro Val Leu Ala Gly Ser Ala Thr Leu Val Ala Leu Gly Ala Leu Ala
         10                  15                  20

TTG TAC GTC GCG AAG CCC TCC GGC TAC GGG AAG CAC ACG GAG AGC CTG     147
Leu Tyr Val Ala Lys Pro Ser Gly Tyr Gly Lys His Thr Glu Ser Leu
 25                  30                  35                  40

AAG CCG GCG GCT ACC CGC CTG CCA GCC CGC GCC GCC TGG TTC CTG CAG     195
Lys Pro Ala Ala Thr Arg Leu Pro Ala Arg Ala Ala Trp Phe Leu Gln
                 45                  50                  55

GAG CTG CCT TCC TTC GCG GTG CCC GCG GGG ATC CTC GCC CGG CAG CCC     243
Glu Leu Pro Ser Phe Ala Val Pro Ala Gly Ile Leu Ala Arg Gln Pro
             60                  65                  70

CTC TCC CTC TTC GGG CCA CCT GGG ACG GTA CTT CTG GGC CTC TTC TGC     291
Leu Ser Leu Phe Gly Pro Pro Gly Thr Val Leu Leu Gly Leu Phe Cys
         75                  80                  85

GTA CAT TAC TTC CAC AGG ACA TTT GTG TAC TCA CTG CTC AAT CGA GGG     339
Val His Tyr Phe His Arg Thr Phe Val Tyr Ser Leu Leu Asn Arg Gly
 90                  95                 100

AGG CCT TAT CCA GCT ATA CTC ATT CTC AGA GGC ACT GCC TTC TGC ACT     387
Arg Pro Tyr Pro Ala Ile Leu Ile Leu Arg Gly Thr Ala Phe Cys Thr
105                 110                 115                 120

GGA AAT GGA GTC CTT CAA GGC TAC TAT CTG ATT TAC TGT GCT GAA TAC     435
Gly Asn Gly Val Leu Gln Gly Tyr Tyr Leu Ile Tyr Cys Ala Glu Tyr
                125                 130                 135

CCT GAT GGG TGG TAC ACA GAC ATA CGG TTT AGC TTG GGT GTC TTC TTA     483
Pro Asp Gly Trp Tyr Thr Asp Ile Arg Phe Ser Leu Gly Val Phe Leu
            140                 145                 150

TTT ATT TTG GGA ATG GGA ATA AAC ATT CAT AGT GAC TAT ATA TTG CGC     531
Phe Ile Leu Gly Met Gly Ile Asn Ile His Ser Asp Tyr Ile Leu Arg
        155                 160                 165

CAG CTC AGG AAG CCT GGA GAA ATC AGC TAC AGG ATT CCA CAA GGT GGC     579
Gln Leu Arg Lys Pro Gly Glu Ile Ser Tyr Arg Ile Pro Gln Gly Gly
170                 175                 180

TTG TTT ACG TAT GTT TCT GGA GCC AAT TTC CTC GGT GAG ATC ATT GAA     627
Leu Phe Thr Tyr Val Ser Gly Ala Asn Phe Leu Gly Glu Ile Ile Glu
185                 190                 195                 200

TGG ATC GGC TAT GCC CTG GCC ACT TGG TCC CTC CCA GCA CTT GCA TTT     675
```

|  |  |  |  |  |  |  |  |  |  |  |  |  |  |  |
|---|---|---|---|---|---|---|---|---|---|---|---|---|---|---|
| Trp | Ile | Gly | Tyr | Ala | Leu | Ala | Thr | Trp | Ser | Leu | Pro | Ala | Leu | Ala | Phe |
|  |  |  |  | 205 |  |  |  | 210 |  |  |  |  | 215 |  |

```
GCA TTT TTC TCA CTT TGT TTC CTT GGG CTG CGA GCT TTT CAC CAC CAT     723
Ala Phe Phe Ser Leu Cys Phe Leu Gly Leu Arg Ala Phe His His His
            220             225                         230

AGG TTC TAC CTC AAG ATG TTT GAG GAC TAC CCC AAA TCT CGG AAA GCC     771
Arg Phe Tyr Leu Lys Met Phe Glu Asp Tyr Pro Lys Ser Arg Lys Ala
        235             240                     245

CTT ATT CCA TTC ATC TTT TAAAGGAACC AAATTAAAAA GGAGCAGAGC            819
Leu Ile Pro Phe Ile Phe
        250

TCCCACAATG CTGATGAAAA CTGTCAAGCT GCTGAAACTG TAATTTTCAT GATATAATAG   879
TCATATATAT ATATATATAT ATATATATAT ATATATATAT GTATATATGT AATAGTAGGT   939
CTCCTGGCGT TCTGCCAGCT GGCCTGGGGA TTCTGAGTGG TGTCTGCTTA GAGTTACTC    999
CTACCCTTCC AGGGACCCCT ATCCTGATCC CCAACTGAAG CTTCAAAAG CCACTTTCC    1059
AAATGGCGAC AGTTGCTTCT TAGCTATTGC TCTGAGAAAG TACAAACTTC TCCTATGTCT  1119
TTCACCGGGC AATCCAAGTA CATGTGGCTT CATACCACT CCCTGTCAAT GCAGGACAAC  1179
TCTGTAATCA AGAATTTTTT GACTTGAAGG CAGTACTTAT AGACCTTATT AAAGGTATGC  1239
ATTTTATACA TGTAACAGAG TAGCAGAAAT TTAAACTCTG AAGCCACAAA GACCCAGAGC  1299
AAACCCACTC CCAAATGAAA ACCCCAGTCA TGGCTTCCTT TTTCTTGGTT AATTAGGAAA  1359
GATGAGAAAT TATTAGGTAG ACCTTAATA CAGGAGCCCT CTCCTCATAG TGCTGAAAAG  1419
ATACTGATGC ATTGACCTCA TTTCAAATTT GTGCAGTGTC TTAGTTGATG AGTGCCTCTG  1479
TTTTCCAGAA GATTTCACAA TCCCCGGAAA ACTGGTATGG CTATTCTTGA AGGCCAGGTT  1539
TTAATAACCA CAAACAAAAA GGCATGAACC TGGGTGGCTT ATGAGAGAGT AGAGAACAAC  1599
ATGACCCTGG ATGGCTACTA AGAGGATAGA GAACAGTTTT ACAATAGACA TTGCAAACTC  1659
TCATGTTTTT GGAAACTGGT GGCAATATCC AAATAATGAG TAGTGTAAAA CAAAGAGAAT  1719
TAATGATGAG GTTACATGCT GCTTGCCTCC ACCAGATGTC CACAACAATA TGAAGTACAG  1779
CAGAAGCCCC AAGCAACTTT CCTTTCCTGG AGCTTCTTCC TTGTAGTTCT CAGGACCTGT  1839
TCAAGAAGGT GTCTCCTAGG GGCAGCCTGA ATGCCTCCCT CAAAGGACCT GCAGGCAGAG  1899
ACTGAAAATT GCAGACAGAG GGGCACGTCT GGGCAGAAAA CCTGTTTTGT TTGGCTCAGA  1959
CATATAGTTT TTTTTTTTTT ACAAAGTTTC AAAAACTTAA AAATCAGGAG ATTCCTTCAT  2019
AAAACTCTAG CATTCTAGTT TCATTTAAAA AGTTGGAGGA TCTGAACATA CAGAGCCCAC  2079
ATTTCCACAC CAGAACTGGA ACTACGTAGC TAGTAAGCAT TTGAGTTTGC AAACTCTTGT  2139
GAAGGGGTCA CCCCAGCATG AGTGCTGAGA TATGGACTCT CTAAGGAAGG GGCCGAACGC  2199
TTGTAATTGG AATACATGGA AATATTTGTC TTCTCAGGCC TATGTTTGCG GAATGCATTG  2259
TCAATATTTA GCAAACTGTT TTGACAAATG AGCACCAGTG GTACTAAGCA CAGAAACTCA  2319
CTATATAAGT CACATAGGAA ACTTGAAAGG TCTGAGGATG ATGTAGATTA CTGAAAAATA  2379
CAAATTGCAA TCATATAAAT AAGTGTTTTT GTTGTTCATT AAATACCTTT AAATCATG    2437
```

( 2 ) INFORMATION FOR SEQ ID NO:6:

( i ) SEQUENCE CHARACTERISTICS:
        ( A ) LENGTH: 254 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met<br>1 | Gln | Val | Gln | Cys<br>5 | Gln | Gln | Ser | Pro | Val<br>10 | Leu | Ala | Gly | Ser | Ala Thr<br>15 |
| Leu | Val | Ala | Leu<br>20 | Gly | Ala | Leu | Ala | Leu<br>25 | Tyr | Val | Ala | Lys | Pro<br>30 | Ser Gly |
| Tyr | Gly | Lys<br>35 | His | Thr | Glu | Ser | Leu<br>40 | Lys | Pro | Ala | Ala | Thr<br>45 | Arg | Leu Pro |
| Ala | Arg<br>50 | Ala | Ala | Trp | Phe<br>55 | Leu | Gln | Glu | Leu | Pro<br>60 | Ser | Phe | Ala | Val Pro |
| Ala<br>65 | Gly | Ile | Leu | Ala | Arg<br>70 | Gln | Pro | Leu | Ser | Leu<br>75 | Phe | Gly | Pro | Pro Gly<br>80 |
| Thr | Val | Leu | Leu | Gly<br>85 | Leu | Phe | Cys | Val | His<br>90 | Tyr | Phe | His | Arg | Thr Phe<br>95 |
| Val | Tyr | Ser | Leu<br>100 | Leu | Asn | Arg | Gly | Arg<br>105 | Pro | Tyr | Pro | Ala | Ile<br>110 | Leu Ile |
| Leu | Arg | Gly<br>115 | Thr | Ala | Phe | Cys | Thr<br>120 | Gly | Asn | Gly | Val | Leu<br>125 | Gln | Gly Tyr |
| Tyr | Leu<br>130 | Ile | Tyr | Cys | Ala | Glu<br>135 | Tyr | Pro | Asp | Gly | Trp<br>140 | Tyr | Thr | Asp Ile |
| Arg<br>145 | Phe | Ser | Leu | Gly | Val<br>150 | Phe | Leu | Phe | Ile | Leu<br>155 | Gly | Met | Gly | Ile Asn<br>160 |
| Ile | His | Ser | Asp | Tyr<br>165 | Ile | Leu | Arg | Gln | Leu<br>170 | Arg | Lys | Pro | Gly | Glu Ile<br>175 |
| Ser | Tyr | Arg | Ile<br>180 | Pro | Gln | Gly | Gly | Leu<br>185 | Phe | Thr | Tyr | Val | Ser<br>190 | Gly Ala |
| Asn | Phe | Leu<br>195 | Gly | Glu | Ile | Ile | Glu<br>200 | Trp | Ile | Gly | Tyr | Ala<br>205 | Leu | Ala Thr |
| Trp | Ser<br>210 | Leu | Pro | Ala | Leu | Ala<br>215 | Phe | Ala | Phe | Phe | Ser<br>220 | Leu | Cys | Phe Leu |
| Gly<br>225 | Leu | Arg | Ala | Phe | His<br>230 | His | His | Arg | Phe | Tyr<br>235 | Leu | Lys | Met | Phe Glu<br>240 |
| Asp | Tyr | Pro | Lys | Ser<br>245 | Arg | Lys | Ala | Leu | Ile<br>250 | Pro | Phe | Ile | Phe | |

( 2 ) INFORMATION FOR SEQ ID NO:7:

( i ) SEQUENCE CHARACTERISTICS:
        ( A ) LENGTH: 1141 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 849..1141

( x i ) SEQUENCE DESCRIPTION: SEQ ID NO:7:

```
GATCTCGGGG TAGCCTCCTT CCCAGCCCTG AGGAAGGAAA GAGACGTCTA CCCCGAGGCC         60
CAAGGAACCG CCCCCTCGCC GCCGCCTCGC AGGCCTCGGT GTCCGGGAAG CCCAGGAGGA        120
GCCCCTGGCC CGCCCGCCGG GGTCCCGGCT CCTACCGCCT CGCCGCGCTT CCACCACCC         180
TCGGCGCCAT CCTCCGCGTC CTCCGGCCGC TGCTGTTGCT GGAGCCGCCG ACCCCGCGAC        240
CGCCGCCCCA TAGCCCACGC GGCCGCGCAC GCAGCACGCA GAAACCGGCC CGCCACGGCC        300
AGAACTCTAG CCCTACACCT CCCGGGACTT CCGGCCGGAA ACCAAGGCCC ACGTGTCCG         360
GGCCTGGTCC TTTCGGGGAC CTTTGGGGAC CGTCCAGGAA TAAGCCCAAA GCGCACAACC        420
```

-continued

```
CGTCTTTCAG AAAAGCGGCG TGACAGGGAA AACAGCGAAC AGCTCTAAGG GGAAAAAAAT       480

GCTCCAGGAA GCAGCCACAA AGGCGTCTCC GCGCGAAGCG CCCAGGTTTC CCACGCGGGC       540

TCAAGGAGCT CCGCGGACAG CCTGAAGCCG CGCGTGCGCA GAGCGGCGCG GGGTTACTGC       600

GGCCCCGGCG TGGGTGGGGC GCTTGCAGGT CCCTCCCCGC GCAAGTGCTC GCCCCGCCCC       660

CGGGGCCGCA CCCACAGCCC CGGCTACCCC GGAGAAGCCT GACTTGAGAA CCCTTTCTGC       720

AGAGTCCCGG CAGTGCGGGA CTCCGGTAGC CGCCCCTCCG GTAGCCGCCC CTCCTGCCCC       780

CGCCGCCGCCG CCCTATATGT TGCCCGCCGC GGCCTCTGGG GCATGGAGCA CGCTGCCCAG      840
```

```
CCCTGGCG ATG GCA ACG GCG ACG GGG GTG GCG GAG GAG CGC CTG CTG GCC       890
         Met Ala Thr Ala Thr Gly Val Ala Glu Glu Arg Leu Leu Ala
          1               5                  10

GCG CTC GCC TAC CTG CAG TGC GCC GTG GGC TGC GCG GTC TTC GCG CGG        938
Ala Leu Ala Tyr Leu Gln Cys Ala Val Gly Cys Ala Val Phe Ala Arg
 15              20                  25                  30

AAT CGT CAG ACG AAC TCA GTG TAC GGC CGC CAC GCG CTG CCC AGC CAC        986
Asn Arg Gln Thr Asn Ser Val Tyr Gly Arg His Ala Leu Pro Ser His
             35                  40                  45

AGG CTC CGA GTG CCG GCG CGG GCC GCC TGG GTG GTG CAG GAG CTG CCC       1034
Arg Leu Arg Val Pro Ala Arg Ala Ala Trp Val Val Gln Glu Leu Pro
         50                  55                  60

TCG CTG GCC CTG CCG CTC TAC CAG TAC GCC AGC GAG TCC GCC CCG CGT       1082
Ser Leu Ala Leu Pro Leu Tyr Gln Tyr Ala Ser Glu Ser Ala Pro Arg
         65                  70                  75

CTC CGC AGC GCG CCC AAC TGC ATC CTC CTG GCC ATG TTC CTC GTC CAC       1130
Leu Arg Ser Ala Pro Asn Cys Ile Leu Leu Ala Met Phe Leu Val His
         80                  85                  90

TAC GGG CAT CG                                                         1141
Tyr Gly His Arg
 95
```

( 2 ) INFORMATION FOR SEQ ID NO:8:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Thr Ala Thr Gly Val Ala Glu Glu Arg Leu Leu Ala Ala Leu
 1               5                  10                  15

Ala Tyr Leu Gln Cys Ala Val Gly Cys Ala Val Phe Ala Arg Asn Arg
             20                  25                  30

Gln Thr Asn Ser Val Tyr Gly Arg His Ala Leu Pro Ser His Arg Leu
         35                  40                  45

Arg Val Pro Ala Arg Ala Ala Trp Val Val Gln Glu Leu Pro Ser Leu
     50                  55                  60

Ala Leu Pro Leu Tyr Gln Tyr Ala Ser Glu Ser Ala Pro Arg Leu Arg
 65                  70                  75                  80

Ser Ala Pro Asn Cys Ile Leu Leu Ala Met Phe Leu Val His Tyr Gly
                 85                  90                  95

His Arg
```

( 2 ) INFORMATION FOR SEQ ID NO:9:

( i ) SEQUENCE CHARACTERISTICS:
        ( A ) LENGTH: 100 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:9:

| GTAACGTCCC | CGGCCCCGC | CCCTACCCTA | CTCCCGGCCC | GGCGTCCTCT | CCGACCCTCC | 60 |
| CCTCACTGCC | CGGTGCCCTC | TCCCCGAAGC | CTCCCCCACC | | | 100 |

(2) INFORMATION FOR SEQ ID NO:10:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

| CAAGAAAGTA | AGATTTAAAA | CCCAAATCAT | TTAAGATAGG | ATTACAGAAA | TGATTATCTT | 60 |
| TAATTTTTA | AAAAATTGTG | CCTGTTTCTT | GTTTCCTAAG | | | 100 |

(2) INFORMATION FOR SEQ ID NO:11:

(i) SEQUENCE CHARACTERISTICS:
        (A) LENGTH: 167 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 2..167

(x i) SEQUENCE DESCRIPTION: SEQ ID NO:11:

```
G TGC TTA ATT TAC CCG TTT CTG ATG CGA GGA GGA AAG CCT ATG CCA CTG         49
  Cys Leu Ile Tyr Pro Phe Leu Met Arg Gly Gly Lys Pro Met Pro Leu
  1               5                   10                  15

TTG GCA TGT ACA ATG GCG ATT ATG TTC TGT ACC TGT AAC GGC TAT TTG           97
Leu Ala Cys Thr Met Ala Ile Met Phe Cys Thr Cys Asn Gly Tyr Leu
            20                  25                  30

CAA AGC AGA TAC TTG AGC CAT TGT GCA GTG TAT GCT GAT GAC TGG GTA          145
Gln Ser Arg Tyr Leu Ser His Cys Ala Val Tyr Ala Asp Asp Trp Val
        35                  40                  45

ACA GAT CCC CGT TTT CTA ATA G                                            167
Thr Asp Pro Arg Phe Leu Ile Gly
        50                  55
```

(2) INFORMATION FOR SEQ ID NO:12:

(i) SEQUENCE CHARACTERISTICS:
        (A) LENGTH: 56 amino acids
        (B) TYPE: amino acid
        (D) TOPOLOGY: linear (i i) MOLECULE TYPE: protein (x i) SEQUENCE DESCRIPTION: SEQ ID NO:12:

```
Cys Leu Ile Tyr Pro Phe Leu Met Arg Gly Gly Lys Pro Met Pro Leu
1               5                   10                  15

Leu Ala Cys Thr Met Ala Ile Met Phe Cys Thr Cys Asn Gly Tyr Leu
            20                  25                  30

Gln Ser Arg Tyr Leu Ser His Cys Ala Val Tyr Ala Asp Asp Trp Val
```

```
                35                        40                         45
Thr Asp Pro Arg Phe Leu Ile Gly
        50                   55
```

( 2 ) INFORMATION FOR SEQ ID NO:13:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GTGAGTGTCC  ACAGCAGTGA  ACTCCGCCTT  GTTCACATCA  TTGCTTTTAT  ATTGATGTCC     60
CAGTGGTT                                                                    68
```

( 2 ) INFORMATION FOR SEQ ID NO:14:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
AATCTGAAGG  GTTGCAATAA  TACTAGTTCA  GTCAGGCTGG  GGCTCGTAGT  GAAATTTTAC     60
GGTTTATTAG  CCATAATCAT  CTTGCAATTT  TTTTCCTTTA  G                         101
```

( 2 ) INFORMATION FOR SEQ ID NO:15:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..101

( x i ) SEQUENCE DESCRIPTION: SEQ ID NO:15:

```
G TTT GGC TTG TGG TTA ACA GGC ATG TTG ATA AAC ATC CAT TCA GAT CAT    49
  Phe Gly Leu Trp Leu Thr Gly Met Leu Ile Asn Ile His Ser Asp His
   1               5                  10                  15

ATC CTA AGG AAT CTC AGA AAA CCA GGA GAT ACT GGA TAC AAA ATA CCA       97
Ile Leu Arg Asn Leu Arg Lys Pro Gly Asp Thr Gly Tyr Lys Ile Pro
            20                  25                  30

AGG G                                                                101
Arg Gly
```

( 2 ) INFORMATION FOR SEQ ID NO:16:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Phe Gly Leu Trp Leu Thr Gly Met Leu Ile Asn Ile His Ser Asp His
```

```
                1                    5                       10                      15
         Ile Leu Arg Asn Leu Arg Lys Pro Gly Asp Thr Gly Tyr Lys Ile Pro
                              20                      25                      30
         Arg Gly
```

( 2 ) INFORMATION FOR SEQ ID NO:17:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
GTACGTACAG  AAAGTGAAGA  ATTTCTGTGA  AAGTTGCTTG  CCATGGTTCC  TGGCTATTTT    60
GTGTTGCCAG  CTCTAAGAAG  TAGTAGCGTA  GTAGTTATTA                            100
```

( 2 ) INFORMATION FOR SEQ ID NO:18:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
TCTTGAATTT  ATGTCTCCAG  GTAAGTATTC  ACTAGCATCT  CTGAAGTCCG  TATTTCATTT    60
TGTAGTAAAT  GCACTACTTT  GGTCTGTGTT  TTCTTCTAG                             99
```

( 2 ) INFORMATION FOR SEQ ID NO:19:

( i ) SEQUENCE CHARACTERISTICS:
        ( A ) LENGTH: 151 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 3..151

( x i ) SEQUENCE DESCRIPTION: SEQ ID NO:19:

```
GA  GGC TTA TTT GAA TAC GTA ACT GCA GCC AAC TAT TTT GGA GAA ATC ATG       50
    Gly Leu Phe Glu Tyr Val Thr Ala Ala Asn Tyr Phe Gly Glu Ile Met
     1               5                  10                  15

GAG TGG TGT GGC TAT GCC CTG GCC AGC TGG TCT GTC CAA GGC GCG GCT           98
Glu Trp Cys Gly Tyr Ala Leu Ala Ser Trp Ser Val Gln Gly Ala Ala
             20                  25                  30

TTT GCT TTC TTC ACG TTT TGT TTT TTA TCT GGT AGA GCA AAA GAG CAT          146
Phe Ala Phe Phe Thr Phe Cys Phe Leu Ser Gly Arg Ala Lys Glu His
         35                  40                  45

CAT GA                                                                   151
His Glu
 50
```

( 2 ) INFORMATION FOR SEQ ID NO:20:

( i ) SEQUENCE CHARACTERISTICS:
        ( A ) LENGTH: 50 amino acids
        ( B ) TYPE: amino acid ( D ) TOPOLOGY: linear ( i i ) MOLECULE TYPE: protein ( x i ) SEQUENCE DESCRIPTION: SEQ ID NO:20:

```
Gly Leu Phe Glu Tyr Val Thr Ala Ala Asn Tyr Phe Gly Glu Ile Met
 1           5                  10                  15

Glu Trp Cys Gly Tyr Ala Leu Ala Ser Trp Ser Val Gln Gly Ala Ala
            20                  25                  30

Phe Ala Phe Phe Thr Phe Cys Phe Leu Ser Gly Arg Ala Lys Glu His
            35                  40                  45

His Glu
    50
```

( 2 ) INFORMATION FOR SEQ ID NO:21:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
GTAAGTTTTA AAACACTTTT ACCATTTGTA ATTTGTTCTT TGACTATATT ATTACCATTT    60

TTCAGGCTAG ATTTTGAAG TGTTAATTTA AATCGCTGAA                          100
```

( 2 ) INFORMATION FOR SEQ ID NO:22:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
ACTGAGTACT CTTTTGTAAT GAAAATATG TCATTTTGTT AGCATTGGTT AAATGTCTAA    60

GCGACAGAAT TATTTCCTTT TTTAATTTTT TTTCTTAG                            99
```

( 2 ) INFORMATION FOR SEQ ID NO:23:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..64

( x i ) SEQUENCE DESCRIPTION: SEQ ID NO:23:

```
G TGG TAC CTC CGG AAA TTT GAA GAG TAT CCA AAG TTC AGA AAA ATT ATA      49
  Trp Tyr Leu Arg Lys Phe Glu Glu Tyr Pro Lys Phe Arg Lys Ile Ile
   1           5                  10                  15

ATT CCA TTT TTG TTT TAAGTGCGTT TTTCATGAAA TTATCTTCAA CTTGAAGCTT T    105
Ile Pro Phe Leu Phe
            20
```

( 2 ) INFORMATION FOR SEQ ID NO:24:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: protein ( x i ) SEQUENCE DESCRIPTION: SEQ ID NO:24:

```
Trp Tyr Leu Arg Lys Phe Glu Glu Tyr Pro Lys Phe Arg Lys Ile Ile
 1               5                  10                  15
Ile Pro Phe Leu Phe
                20
```

( 2 ) INFORMATION FOR SEQ ID NO:25:

( i ) SEQUENCE CHARACTERISTICS:
        ( A ) LENGTH: 1523 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 701..1138

( x i ) SEQUENCE DESCRIPTION: SEQ ID NO:25:

```
TCTAGAACTG GAAATACCAT TTGACCCAGC CATCCCATTA CTGGGTATAT ACCCAAAGGA      60

CTATAAATCA TGCTGCTATA AAGACACATG CACACGTATG TTTATTGTGG CACTATTCAC     120

AATAGCAAAG ACTTGGAAAC AACCCAAATG TCCAACAATG ATAGACTGGA TTAAGAAAAT     180

GTGGCACATA TACACCATGG AATACTATGC AGTCATAAAA AATGATGAGT TCATGTCCTT     240

TGTAGGGACA TGGATGAAAT TGGAAATCAT CATTCTCAGC AAACTATCAC AAGGACAAAA     300

AAACCAAACA CCGCATGTTC TCACTCATAG ATGGGAACTG AACAATGAGA ACACATGGAC     360

ACAGGAAGGG AACATCACA CTCTGGGGAC TGTTGTGGGG TGGGGGAGG GGGAGGGTT      420

AGCATTAGGA GATATACCTA ATGCTAAATG ACGAGTTAAT GGGTGCAGCA CACCAGCATG     480

GCACATGTAT ACATATATAA CTAACCTGCA CATTGTGCAC ATGTACCCTA AAACTTAAAG     540

TATAATAATA ATTAAAAAAA GAAAAAAAAA GAATAAAGAA TATCTCTACA TACTGCCAAA     600

AAAAAAAAAA AAAAGATTCA GATCACTCCC CTCCCGCCCC CGCCCTATAT GTTGCCTGCC     660

TCGGCCTCTG GGGCATGGAG CACGCGGCCC AGCCCTGGCG ATG GCG ACG GCG ACG     715
                                              Met Ala Thr Ala Thr
                                               1               5

GCG ACG GCG GTG GTG GAG GAG CGC CTG CTG GCT GCG TTC GCC TAC CTT     763
Ala Thr Ala Val Val Glu Glu Arg Leu Leu Ala Ala Phe Ala Tyr Leu
                10                  15                  20

CAG TGC GCC GTG GGC TGC GCG GTC TTC GCT CGG AAT CGT CAG ACG AAC     811
Gln Cys Ala Val Gly Cys Ala Val Phe Ala Arg Asn Arg Gln Thr Asn
            25                  30                  35

TCA GTG TAC AGC CGC CAC GCG CCA CCC AGC CGC AGG CTC CGA GTG CCG     859
Ser Val Tyr Ser Arg His Ala Pro Pro Ser Arg Arg Leu Arg Val Pro
        40                  45                  50

GCG CGG GCC ACC CGG GTG GTG CAG AAG CTG CCC TCA CTG GCC CTG CCG     907
Ala Arg Ala Thr Arg Val Val Gln Lys Leu Pro Ser Leu Ala Leu Pro
    55                  60                  65

CTC TAC CAG TAC ACC AGT GAG TCC ACC CCG CGC CTC CGC AGC GCG CCC     955
Leu Tyr Gln Tyr Thr Ser Glu Ser Thr Pro Arg Leu Arg Ser Ala Pro
70                  75                  80                  85

AGC TGC ATC CTC CTG GCC ATG TTC CTC GTC CAC TAC TGG CAT CGG TGC    1003
Ser Cys Ile Leu Leu Ala Met Phe Leu Val His Tyr Trp His Arg Cys
```

|  |  |  |  |  |  |  |  |  |  |  |  |  |  |  |  |
|---|---|---|---|---|---|---|---|---|---|---|---|---|---|---|---|
|  |  |  | 90 |  |  |  |  | 95 |  |  |  |  | 100 |  |  |
| TTA | ATT | TAC | CCA | TTT | CTG | ATG | CGA | GGA | GGA | AAG | CCT | GTG | CCA | CTG | TTG | 1051 |
| Leu | Ile | Tyr | Pro | Phe | Leu | Met | Arg | Gly | Gly | Lys | Pro | Val | Pro | Leu | Leu |
|  |  | 105 |  |  |  | 110 |  |  |  |  | 115 |
| GCG | TGC | ACA | ATG | GCG | ATT | ATG | TTC | TGT | ACC | TGT | AAT | GGC | TAT | TTG | CAA | 1099 |
| Ala | Cys | Thr | Met | Ala | Ile | Met | Phe | Cys | Thr | Cys | Asn | Gly | Tyr | Leu | Gln |
|  |  | 120 |  |  |  | 125 |  |  |  |  | 130 |
| AGC | AGA | TAC | TTG | AGC | CAT | TGT | GCA | GTG | TAT | GCT | GAT | GAC | TGAGTAAAAG |  |  | 1148 |
| Ser | Arg | Tyr | Leu | Ser | His | Cys | Ala | Val | Tyr | Ala | Asp | Asp |
|  | 135 |  |  |  |  | 140 |  |  |  |  | 145 |

ATCCCGTTT TCTAATAAAT TTGGCTTGT GGTTAACGGG CATGTTGATA AACATCCATT    1208

CAGATCATAT CCTAAGGAAT CTCAGAAAAG CAGGAGATAC TGGATACAAA ATACCAAGGG    1268

GAGGCTTATT TGAATACATA ACTGCAGGCA ACTATTTGG AGAAATCATG GAGTGGCGTG    1328

GCTATGCCCT GGCCAGCTGG TCTGTCCAAG GCGCGACTTT TGCTTTCTTC ACATTTGTT    1388

TTTTATCTGG TAGAGCAAAA GAGCATCATG AGCGGTACCT CCGGAAATTT GAAGAGTATC    1448

CAAAGTTCAG AAAAATTATA ATTCCATTTT TGTTTAAGT GCATTTTCA CGAAATTACC    1508

TTCAACTTGA AGCTT    1523

( 2 ) INFORMATION FOR SEQ ID NO:26:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| Met | Ala | Thr | Ala | Thr | Ala | Thr | Ala | Val | Val | Glu | Glu | Arg | Leu | Leu | Ala |
|---|---|---|---|---|---|---|---|---|---|---|---|---|---|---|---|
| 1 |  |  |  | 5 |  |  |  |  | 10 |  |  |  |  | 15 |  |
| Ala | Phe | Ala | Tyr | Leu | Gln | Cys | Ala | Val | Gly | Cys | Ala | Val | Phe | Ala | Arg |
|  |  |  | 20 |  |  |  | 25 |  |  |  |  | 30 |
| Asn | Arg | Gln | Thr | Asn | Ser | Val | Tyr | Ser | Arg | His | Ala | Pro | Pro | Ser | Arg |
|  |  | 35 |  |  |  |  | 40 |  |  |  |  | 45 |
| Arg | Leu | Arg | Val | Pro | Ala | Arg | Ala | Thr | Arg | Val | Val | Gln | Lys | Leu | Pro |
|  | 50 |  |  |  |  | 55 |  |  |  |  | 60 |
| Ser | Leu | Ala | Leu | Pro | Leu | Tyr | Gln | Tyr | Thr | Ser | Glu | Ser | Thr | Pro | Arg |
| 65 |  |  |  |  | 70 |  |  |  | 75 |  |  |  |  |  | 80 |
| Leu | Arg | Ser | Ala | Pro | Ser | Cys | Ile | Leu | Leu | Ala | Met | Phe | Leu | Val | His |
|  |  |  |  | 85 |  |  |  |  | 90 |  |  |  |  | 95 |
| Tyr | Trp | His | Arg | Cys | Leu | Ile | Tyr | Pro | Phe | Leu | Met | Arg | Gly | Gly | Lys |
|  |  |  | 100 |  |  |  |  | 105 |  |  |  |  | 110 |
| Pro | Val | Pro | Leu | Leu | Ala | Cys | Thr | Met | Ala | Ile | Met | Phe | Cys | Thr | Cys |
|  |  | 115 |  |  |  |  | 120 |  |  |  |  | 125 |
| Asn | Gly | Tyr | Leu | Gln | Ser | Arg | Tyr | Leu | Ser | His | Cys | Ala | Val | Tyr | Ala |
|  | 130 |  |  |  |  | 135 |  |  |  |  | 140 |
| Asp | Asp |
| 145 |

( 2 ) INFORMATION FOR SEQ ID NO:27:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
TGCTTTAAAA AAAAGATTCA GATCACAGCT TCTTTCTTCA TTGGGAGAAC GGGCACTCAG      60
TCTGCTCTGC ATGGAAACCA ACGTCTTTGC TCATTCACAT GTGCATTCTT GGGCATCTTT     120
```

( 2 ) INFORMATION FOR SEQ ID NO:28:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Val Lys Asp Pro Arg Phe Leu Ile Asn Phe Gly Leu Trp Leu Thr Gly
 1               5                  10                  15
Met Leu Ile Asn Ile His Ser Asp His Ile Leu Arg Asn Leu Arg Lys
             20                  25                  30
Ala Gly Asp Thr Gly Tyr Lys Ile Pro Arg Gly Gly Leu Phe Glu Tyr
             35                  40                  45
Ile Thr Ala Gly Asn Tyr Phe Gly Glu Ile Met Glu Trp Arg Gly Tyr
         50                  55                  60
Ala Leu Ala Ser Trp Ser Val Gln Gly Ala Thr Phe Ala Phe Phe Thr
65                  70                  75                  80
Phe Cys Phe Leu Ser Gly Arg Ala Lys Glu His His Glu Arg Tyr Leu
                 85                  90                  95
Arg Lys Phe Glu Glu Tyr Pro Lys Phe Arg Lys Ile Ile Ile Pro Phe
                100                 105                 110
Leu Phe
```

( 2 ) INFORMATION FOR SEQ ID NO:29:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
AGCGGCCGCT                                                            10
```

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
ATAGATCTAC CATGGCAACG GCGA                                            24
```

( 2 ) INFORMATION FOR SEQ ID NO:31:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

AAAGTCCATA GAGAAGCGCC ATTGG 25

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

GARTGGTGYT WYGCNYTNGC 20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TTNGGRTANT CYTCRAAYTT 20

( 2 ) INFORMATION FOR SEQ ID NO:34:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GATTCAGATC AC 12

( 2 ) INFORMATION FOR SEQ ID NO:35:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:35:

AAAGTCCATA GAGAAGCGCC ATTGG 25

( 2 ) INFORMATION FOR SEQ ID NO:36:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:36:

CAGGATCCGA GGCCTCTGGG GCATGGAGCA CGCTGCCCAG CCCTG 45

( 2 ) INFORMATION FOR SEQ ID NO:37:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:37:

CGAAGCTTCA GGGACTCGGA GCCTGTGTCT GGGCA 35